(12) United States Patent
Kirshenbaum et al.

(10) Patent No.: US 9,938,321 B2
(45) Date of Patent: Apr. 10, 2018

(54) CYCLIC PEPTOID OLIGOMERS, PHARMACEUTICAL COMPOSITIONS AND METHODS OF USING THE SAME

(71) Applicants: Kent Kirshenbaum, New York, NY (US); Mia L. Huang, San Diego, CA (US)

(72) Inventors: Kent Kirshenbaum, New York, NY (US); Mia L. Huang, San Diego, CA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/208,235

(22) Filed: Mar. 13, 2014

(65) Prior Publication Data

US 2014/0274916 A1 Sep. 18, 2014

Related U.S. Application Data

(60) Provisional application No. 61/778,573, filed on Mar. 13, 2013.

(51) Int. Cl.
*A61K 38/12* (2006.01)
*C07K 7/64* (2006.01)

(52) U.S. Cl.
CPC ............... *C07K 7/64* (2013.01); *A61K 38/12* (2013.01)

(58) Field of Classification Search
CPC .......... A61K 38/08; A61K 38/12; C07K 7/06; C07K 7/64
See application file for complete search history.

(56) References Cited

U.S. PATENT DOCUMENTS

| | | | |
|---|---|---|---|
| 8,524,663 B2 | 9/2013 | Kirshenbaum et al. | |
| 8,828,413 B2 | 9/2014 | Kirshenbaum et al. | |
| 2010/0222255 A1* | 9/2010 | Kirshenbaum et al. | 514/9 |
| 2012/0015883 A1 | 1/2012 | Sadowski et al. | |
| 2014/0100354 A1 | 4/2014 | Kirshenbaum et al. | |
| 2014/0113862 A1 | 4/2014 | Kirshenbaum et al. | |
| 2015/0011465 A1 | 1/2015 | Kirshenbaum et al. | |
| 2015/0044189 A1 | 2/2015 | Kirshenbaum et al. | |

FOREIGN PATENT DOCUMENTS

| | | |
|---|---|---|
| WO | 2009139922 | 11/2009 |
| WO | 2010098843 | 9/2010 |
| WO | 2013158600 | 10/2013 |

OTHER PUBLICATIONS

Patch et al., "Helical peptoid mimics of magainin-2 amide", J. Am. Chem. Soc., 2003; 125:12092-12093.
Chongsiriwatana et al., "Peptoids that mimic the structure, function, and mechanism of helical antimicrobial peptides", Proc. Natl. Acad. Sci. U.S.A., 2008; 105: 2794-2799.
Fowler et al., "Structure-function relationships in peptoids: recent advances toward deciphering the structural requirements for biological function", Organic & Biomolecular Chemistry, 2009, 7:1508-1524.
Pokorski et al., "Introduction of a triazole amino acid into a peptoid oligomer induces turn formation in aqueous solution", Organic Letters, 2007, 9:2381-2383.
Wu et al., "Peptoid oligomers with alpha-chiral, aromatic side chains: sequence requirements for the formation of stable peptoid helices", Journal of the American Chemical Society, 2001, 123:6778-6784.
Burkoth et al., "Incorporation of unprotected heterocyclic side chains into peptoid oligomers via solid-phase submonomer synthesis", Journal of the American Chemical Society, 2003, 125:8841-8845.
Zasloff, "Magainins, a class of antimicrobial peptides from Xenopus skin: isolation, characterization of two active forms, and partial cDNA sequence of a precursor", Proc. Natl. Acad. Sci. U.S.A.. 1987; 84: 5449-5453.
Comegna et al., "Design, synthesis and antimicrobial properties of non-hemolytic cationic alpha-cyclopeptoids", Bioorganic & Medicinal Chemistry, 2010; 18: 2010-2018.
Huang et al., "A comparison of linear and cyclic peptoid oligomers as potent antimicrobial agents", Chem Med Chem, 2012, 7:114-122.
Kapoor et al., "Antimicrobial peptoids are effective against Pseudomonas aeruginosa biofilms", Antimicrob Agents Ch, 2011; 55: 3054-3057.
Kapoor et al., "Efficacy of antimicrobial peptoids against *Mycobacterium tuberculosis*", Antimicrob Agents Ch, 2011; 55: 3058-3062.
Chongsiriwatana et al, "Short alkylated peptoid mimics of antimicrobial lipopeptides", Antimicrob Agents Ch, 2011; 55: 417-420.
Mowery et al., "Mimicry of antimicrobial host-defense peptides by random copolymers", J. Am. Chem. Soc., 2007; 129: 15474-15476.
Fernandez-Lopez et al., "Antibacterial agents based on the cyclic D,L-alpha-peptide architecture", Nature, 2001; 412: 452-455.

(Continued)

*Primary Examiner* — Jeffrey E. Russel
(74) *Attorney, Agent, or Firm* — Klauber & Jackson LLC

(57) ABSTRACT

Novel peptoid oligomers are disclosed that have a formula represented by the following formula I:

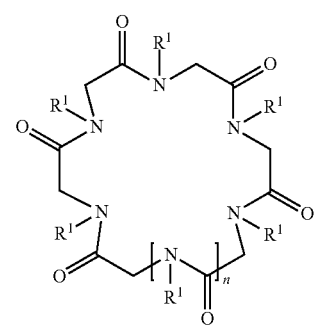

wherein $R^1$ and n are as described herein. The peptoids demonstrate antimicrobial and antimalarial activity and may be prepared as pharmaceutical compositions and used for the prevention or treatment of a variety of conditions in mammals including humans where microbial or malarial infection is involved. The present cyclic peptoids are particularly valuable as their effect is rapid, broad in spectrum and mostly indifferent to resistance provoked by standard antibiotics.

12 Claims, 15 Drawing Sheets

(56) References Cited

OTHER PUBLICATIONS

Vallon-Eberhard et al., "Efficient clearance of Aspergillus fumigatus in murine lungs by an ultrashort antimicrobial lipopeptide, palmitoyl-Lys-Ala-DAla-Lys", Antimicrob Agents Ch, 2008; 52: 3118-3126.

Zuckermann et al., "Peptoids as potential therapeutics", Curr Opin Mol Ther., 2009, 11: 299-307.

Smilkstein et al., "Simple and inexpensive fluorescence-based technique for high-throughput antimalarial drug screening", Antimicrobial Agents and Chemotherapy, 2004; 48: 1803-1806.

Chongsiriwatana et al., "Functional synergy between antimicrobial peptoids and peptides against gram-negative bacteria", Antimicrob Agents Ch, 2011, 55:5399-5402.

Choi et al., "De novo design and in vivo activity of conformationally restrained antimicrobial arylamide foldamers", Proc Natl Acad Sci, 2009, 106: 6968-6973.

Huang et al., "Amphiphilic cyclic peptides that exhibit antimicrobial activity by disrupting *Staphylococcus aureus* membranes", Eur J Org Chem, 2013, 3560-3566.

DeCola et al., "Gadolinium-binding cyclic hexapeptoids: synthesis and relaxometric properties", Organic & Biomolecular Chemistry, 2014, 12:424-431.

Izzo et al, "Structural effects of proline substitution and metal binding on hexameric cyclic peptoids", Organic Letters, 2013, 15:598-601.

Della Sala et al., "Cyclopeptoids: a novel class of phase-transfer catalysts", Organic and Biomolecular Chemistry, 2013, 11:726-731.

Levine et al., "Multivalent peptidomimetic conjugates: a versatile platform for modulating androgen receptor activity", J. Am Chem Soc, 2012, 134:6912-6915.

Paul et al., "N-naphthyl peptoid foldamers exhibiting atropisomerism", Organic Letters, 2012, 14:926-929.

Butterfoss et al., "A preliminary survey of the peptoid folding landscape", J. Am. Chem Soc., 2009, 131:16798-16807.

Comegna et al., "An efficient modular approach for the assembly of s-linked glycopeptoids", Organic Letters, 2009, 11:3898-3901.

DeCola et al., "Size-dependent cation transport by cyclic alpha-peptoid ion carriers", Organic & Biomolecular Chemistry, 2009, 7:2851-2854.

Shin et al., "Cyclic peptoids", J Am Chem Soc, 2007, 129:3218-3225.

McGeary et al., "Peptidostarands: valence tautomers of cyclic peptides", Tetrahedron Letters, 1999, 40:3041-3044.

Sugihara et al., "Studies on cyclic peptides. IV. Conformation of cyclo(sar-sar-gly)2, cyclo(sar)6, and cyclo(sar-gly-gly)2, and their conformational change induced by alkali thiocyanates", Biopolymers, 1976, 15:1529-1542.

Yang et al., "Peptide-water association in peptide crystals", Int J Peptide Protein Res, 1979, 14:12-20.

Shah et al., "Oligo(N-aryl glycines): a new twist on structured peptoids", J Am Chem Soc, 2008, 130:16622-16632.

Maulucci et al., "Synthesis, structures, and properties of nine-, twelve-, and eighteen-membered N-benzyloxyethyl cyclic alpha-peptoids", Chem Commun, 2008, 33:3927-3929.

Kolaskar, "The nonplanar peptide unit. IV. geometry and nonplanar distortions of the cis-peptide unit", Biopolymers, 1980, 19:1345-1355.

Thomaides et al., "Electron-rich hexasubstituted benzene derivatives and their oxidized cation radicals, dications with potential triplet ground states and polycations", J Am Chem Soc, 1988, 110:3970-3979.

Miller et al., "Hexaazaotadecahydrocoronene. Structural and physical properties of [HOC]n (n=0, 1+, 2+,3+, 4+)", Journal of the American Chemical Society, 1990, 112:381-398.

\* cited by examiner

Fig. 11

| R | Scaffold | Compound | MIC [μg mL⁻¹] | R | Scaffold | Compound | MIC [μg mL⁻¹] |
|---|---|---|---|---|---|---|---|
| diphenylmethyl | A | C3 | 3.9 | phenyl | A | C115 | >500 |
|  | B | C101 | 250 |  | B | C116 | >500 |
|  | C | C102 | 3.9 |  |  |  |  |
| diphenylpropyl | A | C103 | 3.9 | 4-fluorophenyl | A | C117 | 31.3 |
| diphenylmethyl | A | C104 | 3.9 | α-methylbenzyl | A | C118 | 250 |
|  |  |  |  |  | B | C119 | >500 |
| biphenyl | A | C105 | 3.9 | α-methylbenzyl | A | C120 | 250 |
| fluorenyl | A | C106 | 3.9 | α-methyl-4-fluorobenzyl | A | C121 | 31.3 |
|  | B | C107 | >500 |  |  |  |  |
| 9-fluorenyl | A | C108 | 62.5 | 4-methylbenzyl | A | C122 | 15.6 |
| naphthyl | A | C109 | 3.9 | 4-CF₃-benzyl | A | C123 | 3.9 |
|  | B | C110 | >500 |  |  |  |  |
| indolyl | A | C111 | 62.5 | 3,5-dimethylbenzyl | A | C124 | 3.9 |
|  | B | C112 | >500 |  |  |  |  |
|  | C | C113 | 62.5 |  |  |  |  |
| benzodioxolyl | A | C114 | 250 | 3,5-bis(CF₃)benzyl | A | C125 | 3.9 |

CYCLIC PEPTOID OLIGOMERS, PHARMACEUTICAL COMPOSITIONS AND METHODS OF USING THE SAME

CROSS REFERENCE TO RELATED APPLICATIONS

This application claims priority under 35 USC § 119(e) from U.S. Provisional Application Ser. No. 61/778,573, filed Mar. 13, 2013, which application is herein specifically incorporated by reference in its entirety.

GOVERNMENTAL SUPPORT

The research leading to the present invention was supported, at least in part, by National Science Foundation Award CHE-1152317. Accordingly, the Government has certain rights in the invention.

FIELD OF THE INVENTION

This invention relates to novel compositions containing active benzyl substituted cyclic peptoids, and particularly, such benzyl substituted cyclic peptoids as demonstrate antimicrobial, antifungal, and/or antiviral activity. The invention also relates to methods for the preparation of the benzyl substituted cyclic peptoids and compositions thereof, and their use in preventing and/or treating conditions resulting from the unwanted presence of microbial, fungal, or viral activity. This invention also relates to use of benzyl substituted cyclic peptoids and compositions thereof in preventing and/or treating conditions resulting from gram positive and gram negative bacterial strains. The invention generally relates to use of benzyl substituted cyclic peptoids and compositions thereof in pharmaceutical, healthcare, medical device, industrial, food, agricultural, and personal care applications.

BACKGROUND OF THE INVENTION

Antimicrobial agents play a crucial role in the treatment of disease. Since the advent of modern antibiotics, it has become apparent that pathogens are capable of developing resistance to antibiotic drug therapy. Increasingly, pathogens that manifest resistance to multiple classes of antibiotics are becoming prevalent, setting the stage for a crisis in global public health. New pharmacological options are urgently needed, preferably including strategies that are likely to remain effective over a sustained course of time.

The incidence of bacterial infections such as methicillin-resistant *Staphylococcus aureus* (MRSA) causes tens of thousands of deaths annually, and leads to more than $2 billion in health care costs. The discovery of new anti-infective agents has been disappointingly slow. One promising strategy is to develop therapeutic compounds that exert their activity on cellular membranes. Microbial species may be incapable of significantly altering the characteristics of their membrane lipid components. This suggests that compounds capable of selectively disrupting microbial membrane function will yield improved drugs that can deter the emergence of antibiotic resistance.

In the field of peptidomimetics research, extensive efforts have been made to recapitulate the structural features present in naturally occurring bioactive peptides (Ripka et al. Curr. Opin. in Chem. Bio. 1998, 2, 441-452; Steer et al. Curr. Med. Chem. 2002, 9, 811-822; Patch et al. Curr. Opin. In Chem. Biol. 2002, 6, 872-877). Many functional peptidomimetics such as magainin mimics (Liu et al. J. Am. Chem. Soc. 2001, 123, 7553-7559; Wieprecht et al. Biochemistry 1996, 35, 10844-10853; Porter et al. J. Am. Chem. Soc. 2005, 127, 11516-11529; Numao et al. Biol. Pharm. Bull. 1997, 20, 800-804; Rennie et al. J. Ind. Microbiol. Biotechnol. 2005, 32, 296-300), integrin mimics (Pasqualini et al. J. Cell Biol. 1995, 130, 1189-1196; Scarborough et al. Curr. Med. Chem. 1999, 6, 971-981) and somatostatin mimics (Gademann et al. J. Med. Chem. 2001, 44, 2460-2468; Gademann et al. Helv. Chim. Acta 2000, 83, 16-33) highlight the significance of structural mimicry for their function. More recently, efforts have been made to enhance the conformational ordering of peptidomimetic oligomers (Fink et al. J. Am. Chem. Soc. 1998, 120, 4334-4344; Phillips et al. J. Am. Chem. Soc. 2002, 124, 58-66; Abell et al. Lett. Pept. Sci. 2001, 8, 267-272; Clark et al. J. Am. Chem. Soc. 1995, 117, 12364-12365; Dimartino et al. Org. Lett. 2005, 7, 2389-2392). Stabilizing or rigidifying polymer conformations may lead to enhanced binding affinities (Sewald et al., *Peptides: Chemistry and Biology*. Wiley-VCH: Weinheim, Germany: 2002; Wipf. Chem. Rev. 1995, 95, 2115-2134). To this end, several methods have been developed to enhance the conformational ordering of non-natural polymers (Sewald et al., *Peptides: Chemistry and Biology*. Wiley-VCH: Weinheim, Germany: 2002; Wipf. Chem. Rev. 1995, 95, 2115-2134; Holub et al. Org. Lett. 2007, 9, 3275-3278). These methods include the introduction of both covalent and non-covalent intramolecular interactions. Some examples of covalent constraints include site-specific macrocyclization via Huisgen 1,3-dipolar cycloaddition (Holub et al. Org. Lett. 2007, 9, 3275-3278), head-to-tail macrocyclization (Gademann et al. Angew. Chem., Int 1999, 38, 1223-1226; Robinson et al. Bioorg. Med. Chem. 2005, 13, 2055-2064; Wels et al. Bioorg. Med. Chem. Lett. 2005, 15, 287-290; Shankaramma et al. Chem. Commun. 2003, 1842-1843; Locardi et al. J. Am. Chem. Soc. 2001, 123, 8189-8196; Chakraborty et al. J. Org. Chem. 2003, 68, 6257-6263; Angell et al. J. Org. Chem. 2005, 70, 9595-9598; Norgren et al. J. Org. Chem. 2006, 71, 6814-6821; Clark et al. J. Am. Chem. Soc. 1998, 120, 651-656; Yuan et al. J. Am. Chem. Soc. 2004, 126, 11120-11121; Nnanabu et al. Org. Lett. 2006, 8, 1259-62; Jiang et al. Org. Lett. 2004, 6, 2985-2988; Mann et al. Org. Lett. 2003, 5, 4567-4570; Wels et al. Org. Lett. 2002, 4, 2173-2176; Bru et al. Tetrahedron Lett. 2005, 46, 7781-7785; Vaz et al. Org. Lett. 2006, 8, 4199-4202; Buttner et al. Chem. Eur. J. 2005, 11, 6145-6158; Royo et al. Tetrahedron Lett. 2002, 43, 2029-2032) and generation of hydrogen bond surrogates via metathesis reactions (Dimartino et al. Org. Lett. 2005, 7, 2389-2392).

Peptoids, for example, are a class of peptidomimetics that comprise N-substituted glycine monomer units (Figliozzi et al, Synthesis of N-substituted glycine peptoid libraries. In *Methods Enzymol.*, Academic Press: 1996; Vol. 267, pp 437-447; Bartlett et al., Proc. Natl. Acad. Sci. U.S.A. 1992, 89, 9367-9371). Peptoids are an important class of sequence-specific peptidomimetics shown to generate diverse biological activities (Patch et al. In *Pseudo-peptides in Drug Development*; Nielson, P. E., Ed.; Wiley-VCH: Weinheim, Germany, 2004; pp 1-35; Miller et al. Drug Dev. Res. 1995, 35, 20-32; Murphy et al. Proc. Natl. Acad. Sci. U.S.A. 1998, 95, 1517-1522; Nguyen et al. Science 1998, 282, 2088-2092; Ng et al. Bioorg. Med. Chem. 1999, 7, 1781-1785; Patch et al. J. Am. Chem. Soc. 2003, 125, 12092-12093; Wender et al. Proc. Natl. Acad. Sci. U.S.A. 2000, 97, 13003-13008; Wu et al. Chem. Biol. 2003, 10, 1057-1063; Chongsiriwatana et al. Proc. Natl. Acad. Sci. U.S.S. 2008, 105, 2794-2799). Oligopeptoids can be designed to display chemical moieties analogous to the bioactive peptide side chains while their abiotic backbones provide protection from proteolytic degradation.

Peptoid sequences comprised of bulky chiral side chains have the capacity to adopt a stable helical secondary structure, although some conformational heterogeneity is evident in solution (Armand et al. *Proc. Natl. Acad. Sci. U.S.A.* 1998, 95, 4309-4314; Kirshenbaum et al. *Proc. Natl. Acad. Sci. U.S.A.* 1998, 95, 4303-4308; Wu et al. *J. Am. Chem. Soc.* 2003, 125, 13525-13530). The crystal structure of a linear peptoid homopentamer composed of bulky chiral side chains exhibits a helical conformation resembling that of a polyproline type I helix (Armand et al. *Proc. Natl. Acad. Sci. U.S.A.* 1998, 95, 4309-4314; Kirshenbaum et al. *Proc. Natl. Acad. Sci. U.S.A.* 1998, 95, 4303-4308; Wu et al. *J. Am. Chem. Soc.* 2003, 125, 13525-13530). Oligopeptoid sequences incorporating repeating units of two bulky chiral side chains and a cationic side chain can form facially amphiphilic helical structures. Recent studies describe antimicrobial activities generated from facially amphiphilic helical peptoids (Patch et al. *J. Am. Chem. Soc.* 2003, 125, 12092-12093; Chongsiriwatana et al. *Proc. Natl. Acad. Sci. U.S.S.* 2008, 105, 2794-2799). These peptoid oligomers are reported to be good functional mimics of maganin-2 amide, a peptide antimicrobial agent from *Xenopus* skin (Patch et al. *J. Am. Chem. Soc.* 2003, 125, 12092-12093; Zasloff. *Proc. Natl. Acad. Sci. USA* 1987, 84, 5449-5453).

Antimicrobials can have a 'specific mode of action or a 'non-specific mode of action'. Antimicrobials that undergo a 'specific mode of action' inhibit bacterial metabolism and antimicrobials that undergo a 'non-specific mode of action' disrupt bacterial membranes (Brogden. *Nat. Tev. Microbiol.* 2005, 3, 238-250). An example of a peptide antimicrobial that undergoes a 'specific mode of action' is penicillin, which inhibits DD-transpeptidase, a bacterial enzyme responsible for cross-linking the peptidoglycan chains that form rigid bacterial cell walls (Waxman et al. *Ann. Rev. Biochem.* 1983, 52, 825-869; Jenssen et al. *Clin. Microbiol. Rev.* 2006, 19, 491-511; Findlay et al. *Antimicrobiol Agents Chemother.,* 2010, 54, 4049-4058). Some examples of peptide antimicrobials that undergo a 'non-specific mode of action' include maganin 2, protegrin-1, melittin, and alamethicin, all of which disrupt bacterial cell membranes (Waxman et al. *Ann. Rev. Biochem.* 1983, 52, 825-869; Jenssen et al. *Clin. Microbiol. Rev.* 2006, 19, 491-511; Findlay et al. *Antimicrobiol Agents Chemother.,* 2010, 54, 4049-4058). Amphiphilicity is a common structural feature found in peptide antimicrobials, especially the ones that exhibit helical secondary structure (Tossi et al. *Biopolymers* 2000, 55, 4-30). There are three widely accepted mechanisms for helical peptide antimicrobials. These antimicrobials are believed to undergo 'barrel-stave', 'carpet', or 'toroidal-pore' mechanisms (Waxman et al. *Ann. Rev. Biochem.* 1983, 52, 825-869; Jenssen et al. *Clin. Microbiol. Rev.* 2006, 19, 491-511; Findlay et al. *Antimicrobiol Agents Chemother.,* 2010, 54, 4049-4058). In all three mechanisms, amphiphilic structure plays a key role in disrupting bacterial membranes.

SUMMARY OF THE INVENTION

In an effort to discover peptoid sequences with enhanced antimicrobial activity, a library of benzyl substituted cyclic peptoid oligomers was synthesized. The side chain moieties included in the library contain both direct mimics of peptide side chains and also non-proteinogenic side chains. The inventors demonstrate that the benzyl substituted cyclic peptoid oligomers of the present invention are potent and selective antimicrobials. The optimized peptoid sequences are non-toxic to human red blood cells and show potent antimicrobial activities against both gram positive and gram negative bacterial strains, such as *E. coli, S. aureus*, and *B. subtilis*.

Accordingly, the present inventors have determined that antibiotic benzyl substituted cyclic peptoid oligomers may be prepared that exhibit enhanced stability, due, at least in part, to resistance to enzymatic digestion.

As demonstrated herein, peptoid oligomers of the present invention exhibit antibiotic activity, with minimal host cell toxicity. These findings lead to novel peptoid oligomers that are promising candidates for therapeutic use. It also leads to pharmaceutical compositions comprising the benzyl substituted cyclic peptoids of the present invention as active ingredients and to their use to treat, prevent or ameliorate a range of conditions in mammals of various genesis or etiology, and primarily those caused by bacteria, viruses, or fungi.

Also shown herein, peptoid oligomers of the present invention exhibit anti-malarial activity and, more specifically, can inhibit the growth of *Plasmodium falciparum* (*P. falciparum*), one of the species of *Plasmodium* that causes malaria in humans. *P. falciparum* is a protozoan parasite which is transmitted by female *Anopheles* mosquitoes. Malaria is a disease of epidemic proportions in many parts of the world wherein it is endemic. Malaria caused by *P. falciparum* is the most virulent form of malaria, with the highest complication rates and mortality. An estimated 80 to 300 million humans are diagnosed with and/or treated for malaria annually, the majority of which were children under the age of five (Mueller et al. *Lancet Infect. Dis.* 2009, 9:555-566; Bousema et al. *Clin. Microbiol. Rev.* 2011, 24:377-410). Given the number of people infected and the increase in resistance of malarial parasites to standard antimalarial drugs such as choroquine, there is a genuine need for agents and compounds that can used to treat malarial infections, particularly those caused by *P. falciparum*. Accordingly, the findings presented herein, showing that peptoid oligomers of the invention show significant activity with respect to the ability to inhibit growth of *P. falciparum* provide evidence that the peptoid oligomers described herein may be used to advantage to treat subjects suffering from malarial infections.

More particularly, the present invention relates to peptoid oligomers having antimicrobial and/or antimalarial properties, according to formula I:

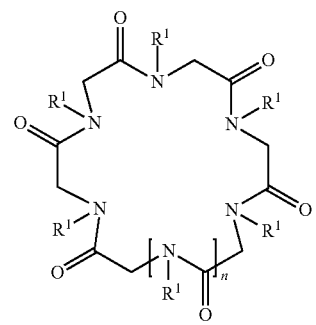

I or a pharmaceutically acceptable salt, solvate or prodrug thereof; and stereoisomers, isotopic variants and tautomers thereof;

wherein
each R¹ is independently fluorenyl, 2-(indol-3-yl)ethyl, or a group selected from

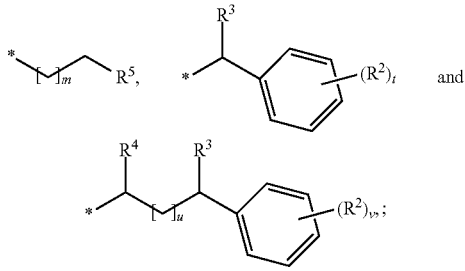

each R² is independently substituted or unsubstituted alkyl, substituted or unsubstituted phenyl, haloalkyl, halo, substituted or unsubstituted alkoxy, or cyano;
each R³ is independently H, methyl, or phenyl; each R⁴ is independently H, or methyl;
each R⁵ is independently —NR$^{6a}$R$^{6b}$; each R$^{6a}$ and R$^{6b}$ is independently H, substituted or unsubstituted alkyl, or substituted or unsubstituted aryl;
the subscript n is 0 or 1; the subscript m is 0, 1, 2, 3, or 4; the subscript t is 1, 2, 3, 4, or 5; the subscript u is 0, 1, or 2; the subscript v is 0, 1, 2, 3, 4, or 5;
and * denotes the attachment point;
and
provided that
i) at least one of R¹s is

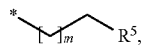

and at least one of R¹s is fluorenyl, 2-(indol-3-yl)ethyl, or a group selected from

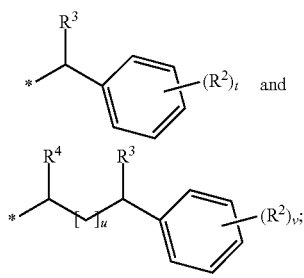

and
ii) the compound is other than

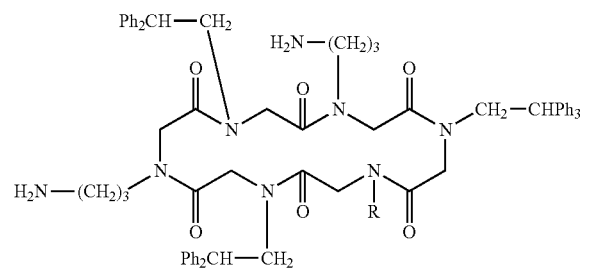

wherein R is —(CH$_2$)$_3$NH$_2$,

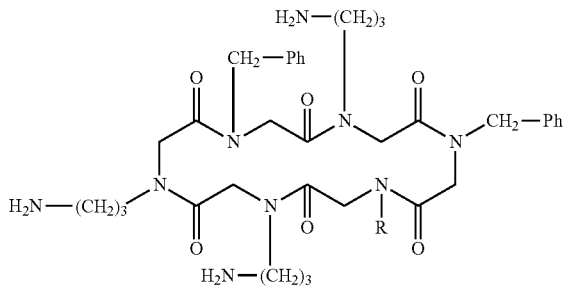

wherein R is —(CH$_2$)$_3$NH$_2$,

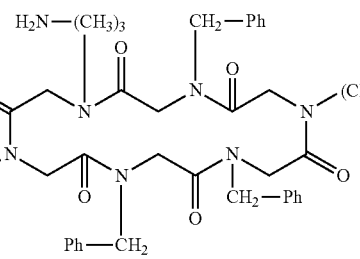

wherein R is —(CH$_2$)$_3$NH$_2$,

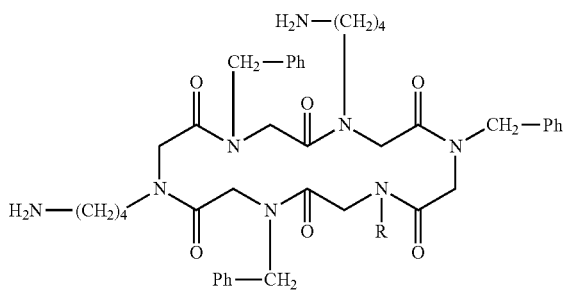

wherein R is —(CH$_2$)$_4$NH$_2$,

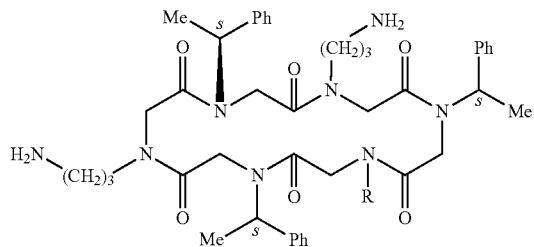

wherein R is —(CH$_2$)$_3$NH$_2$,

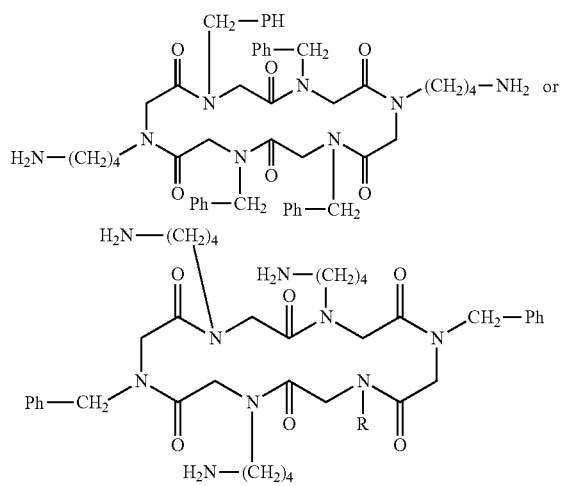

wherein R is —(CH$_2$)$_4$NH$_2$.

In one aspect, the present invention provides benzyl substituted cyclic peptoid oligomers according to the formula I, wherein at least one of the R$^1$s is

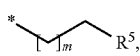

and the rest are selected from

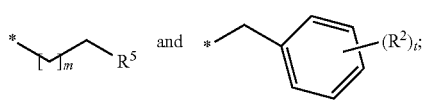

and * denotes the attachment point.

In one aspect, the present invention provides benzyl substituted cyclic peptoid oligomers according to the formula I, wherein at least one of the R$^1$s is

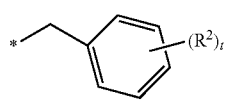

and the rest are selected from

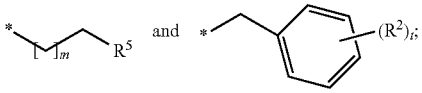

and * denotes the attachment point.

In one particular aspect, the present invention provides benzyl substituted cyclic peptoid oligomers according to the formula I, wherein phenyl of the benzyl is substituted. In one particular embodiment, phenyl is substituted with substituted or unsubstituted alkyl, haloalkyl, halo, substituted or unsubstituted alkoxy, or cyano.

In one particular aspect, the present invention does not include benzyl substituted cyclic peptoids or peptoid oligomers where phenyl of benzyl is unsubstituted.

In one particular aspect, the present invention only includes benzyl substituted cyclic peptoids or peptoid oligomers where phenyl of benzyl is substituted.

In one embodiment, with respect to peptoid oligomers of formula I, R$^1$ is 3-aminopropyl, 4-aminobutyl, or 5-aminopentyl.

In a further aspect, the present invention provides a method for the preparation of the peptoid oligomers of the invention.

In a further aspect, the peptoid oligomers of the invention may be used to treat viral, microbial or fungal conditions affecting lower animals, and possibly, plants. The peptoid oligomers described herein may also be used to advantage to treat protozoal and parasitic conditions affecting animals and humans, as well as plants. The peptoid oligomers could be designed and assembled to include the peptoid oligomers pertinent for the treatment of a particular microbe or fungus of interest, and then formulated into appropriate compositions and dosage forms for administration or application to an affected host. Moreover, such compositions may comprise the peptoid oligomers of the invention in mixtures or combinations with other antibiotic agents, such as known antibiotic compounds. In such formulations, the peptoid oligomers of the invention may act synergistically with the known antibiotic compounds, so that the resulting composition demonstrates improved effectiveness.

In a further aspect, the peptoid oligomers of the invention may be used to treat conditions resulting from gram positive and gram negative bacterial strains.

In a further aspect, the peptoid oligomers of the invention may be used to treat various forms of infectious diseases such as Methicillin-resistant *Staphylococcus aureus* (MRSA).

In a further aspect, the peptoid oligomers of the invention may be used to treat malaria resulting from infection with *P. falciparum*.

In a further aspect, the present invention provides pharmaceutical compositions comprising a peptoid of the invention, and a pharmaceutical carrier, excipient or diluent. In this aspect of the invention, the pharmaceutical composition can comprise one or more variant peptoid oligomers of the invention, prepared, for example, with a differing array of peptoid linkers, to afford a more comprehensive treatment in the instance where a multiplicity of microbial/viral/fungal antigens are known to be present. Likewise, and as stated above, the pharmaceutical compositions may comprise one or more of the peptoid oligomers of the invention, in combination with other antibiotic agents or compounds, including known antibiotic compounds.

In a further aspect of the invention, a method is disclosed for treating mammals, including humans, as well as lower mammalian species, susceptible to or afflicted with a condition attributable to or resulting from a microbial, viral or fungal infection, which method comprises administering an effective amount of a pharmaceutical composition containing or comprising the peptoid oligomers just described.

In a further aspect of the invention, a method is disclosed for treating mammals, including humans, as well as lower mammalian species, susceptible to or afflicted with a condition attributable to or resulting from a *P. falciparum* infection, which method comprises administering an effective amount of a pharmaceutical composition containing or comprising the peptoid oligomers just described.

In addition to the methods of treatment set forth above, the present invention extends to the use of any of the compounds of the invention for the preparation of medicaments or as medicaments, that may be administered for such treatments, as well as to such compounds for the treatments disclosed and specified.

The present invention also encompasses antimicrobial or antimalarial compositions comprising any of the compounds of the invention, an antimicrobial substrate comprising any of the compounds of the invention, wherein such a compound or compounds are bound to or incorporated into the substrate, and an article comprising an antimicrobial substrate. Such articles include, without limitation, a personal care item, an agricultural item, a cosmetic, a package, a food handling item, a food delivery item, a personal garment, a medical device, a personal hygiene item, an article intended for oral contact, a household item, a toy, or a liquid separation article.

Also encompassed herein are methods for making antimicrobial substrates using the compounds of the invention. The present invention further extends to the use of any of the compounds of the invention for the generation of antimicrobial substrates.

In additional aspects, this invention provides methods for synthesizing the complexes of the invention, with representative synthetic protocols and pathways disclosed herein below.

Other objects and advantages will become apparent to those skilled in the art from a consideration of the ensuing detailed description, which proceeds with reference to the following illustrative drawings.

BRIEF DESCRIPTION OF THE DRAWINGS

FIG. 11 shows additional chemical structures of cyclic peptoid compounds and their corresponding antimicrobial activities. The susceptibility of MRSA USA300 to cyclic peptoid oligomers was evaluated. Three different peptoid scaffold types were evaluated, including hexamers (scaffold A) and pentamers (scaffold B or C). MIC: Minimum Inhibitory Concentration.

DETAILED DESCRIPTION OF THE INVENTION

Definitions

Figure 1:
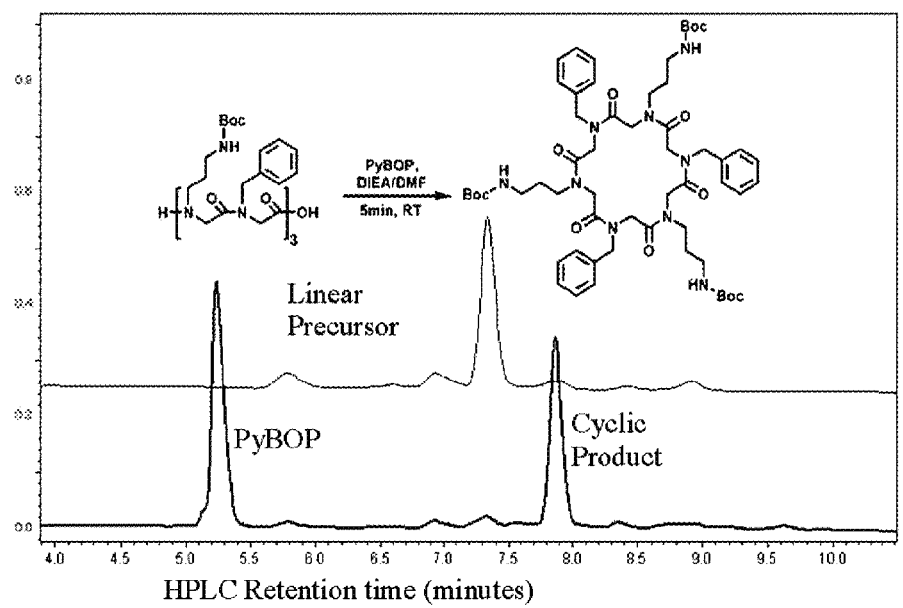
FIG. 1 shows a representative cyclization reaction monitored by RP-HPLC. The Boc protecting groups used on amino groups were removed after the cyclization step in 95% TFA/$H_2O$.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

N-Substituted Glycine Monomer Designators:
Nap=N-(3-aminopropyl)glycine
Nab=N-(4-aminobutyl)glycine
Nah=N-(6-aminohexyl)glycine
Ngb=N-(4-guanidinobutyl)glycine
Npm=N-(phenylmethyl)glycine
Ndpm=N-(1,1-diphenylmethyl)glycine
Npp=N-(benzylphenyl)glycine
N2flene=N-(2-fluorene)glycine
N9flene=N-(9-fluorene)glycine
Nnm=N-(naphthylmethyl)glycine
Ndp=N-(2,2-diphenylethyl)glycine
Ndpp=N-(3,3-diphenylpropyl)glycine
Nip=N-(isopropyl)glycine
Nib=N-(isobutyl)glycine.

Additional monomers are listed in Table S2.
N-Substituted Glycine Monomer Designators:

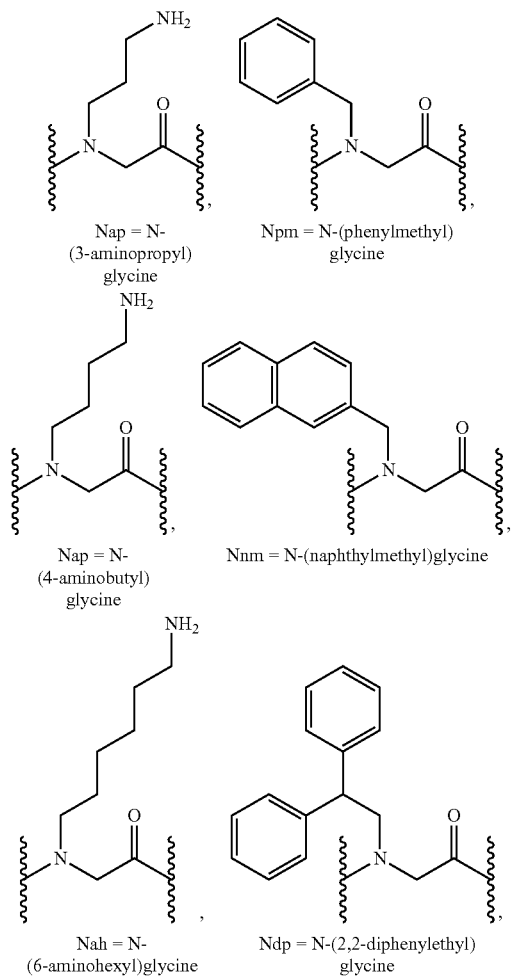

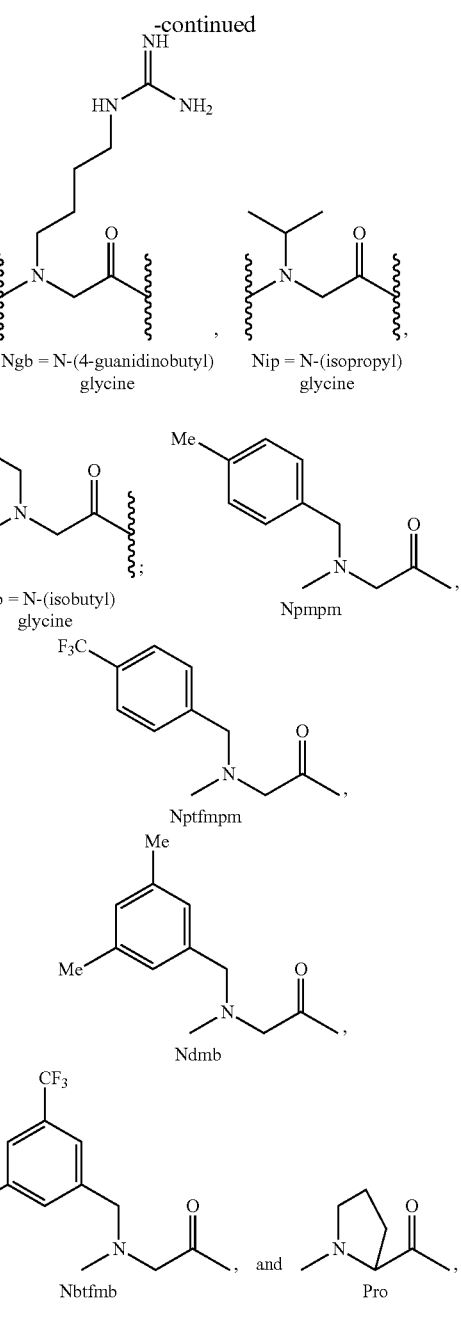

'Acyl' or 'Alkanoyl' refers to a radical —C(O)R$^{20}$, where R$^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently
$C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —$OR^{29}$ where $R^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl, n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and iso-amyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R'', —SO$_2$NR''R''', —C(O)R'', —C(O)OR'', —OC(O)R'', —NR'''C(O)R'', —C(O)NR''R''', —NR''R''', or —(CR'''R'''')$_m$OR'''; wherein each R'' is independently selected from H, $C_1$-$C_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R''' and R'''' independently represents H or $C_1$-$C_8$ alkyl.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or poly-cyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

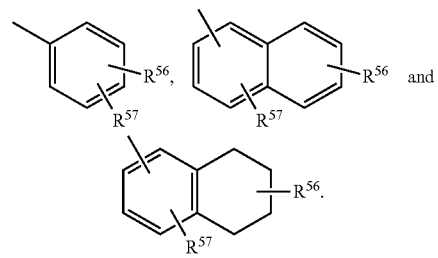

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O or S. R$^{60}$ and R$^{61}$ are independently hydrogen, C1-C8 alkyl, C1-C4 haloalkyl, C3-C10 cycloalkyl, 4-10 membered heterocycloalkyl, C6-C10 aryl, substituted aryl, 5-10 membered heteroaryl.

'Heteroaryl' means an aromatic ring structure, monocyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

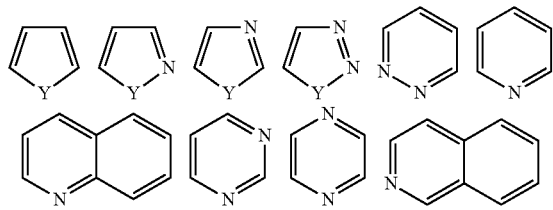

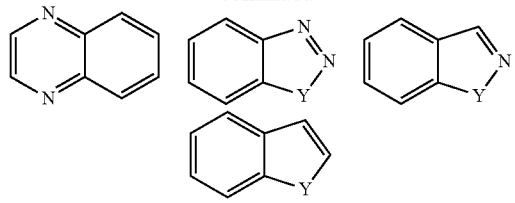

wherein each Y is selected from carbonyl, N, NR$^{65}$, O and S; and R$^{65}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

Examples of representative aryl having hetero atoms containing substitution include the following:

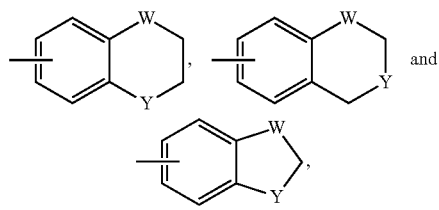

wherein each W is selected from C(R$^{66}$)$_2$, NR$^{66}$, O and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

"Unnatural amino acids" means amino acids and corresponding peptoid oligomers that are synthesized from single amino acid starting materials. Such unnatural amino acids may be prepared and used individually in accordance with the present invention, or may incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, Science, 244: 182-188 (April 1989).

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "patient" and "subject" are used interchangeably herein. Accordingly, a subject can be a mammal, in a particular embodiment a human, or a bird, a reptile, an amphibian, or a plant.

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-C12 substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2H$ or D), carbon-13 ($^{13}C$), nitrogen-15 ($^{15}N$), or the like. It will be understood that, in a compound comprising an unnatural proportion of an isotope, any example of an atom where present, may vary in isotope composition. For example, any hydrogen may be $^2H/D$, or any carbon may be $^{13}C$, or any nitrogen may be $^{15}N$, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The Peptoid Oligomers

As set forth earlier herein, the glycine peptoid macrocycles of the present invention comprise benzyl substituted cyclic peptoids with antimicrobial, antiviral, and/or antifungal properties. Accordingly, the compounds may be cyclic peptoids and may have a lethal effect on bacteria, viruses, and/or fungi. More particularly, the benzyl substituted cyclic peptoids may be any benzyl substituted cyclic peptoids, or fragments thereof, natural cyclic peptoids, and any synthetic analogs or de novo designs. These benzyl substituted cyclic peptoids can accordingly include nonnatural amino acids: beta-amino acids, d-amino acids and/or non-indigenous amino acids.

Peptoids exhibit many advantageous characteristics for development of bioactive compounds, as they:
- are amenable to efficient solid phase synthesis;
- can incorporate highly diverse chemical functionalities;
- can establish a relationship between oligomer sequence, three-dimensional structure, and function;
- do not require the presence of chiral centers; can demonstrate marked resistance to degradation;
- have superior cell permeability characteristics relative to peptoids or peptoid oligomers;
- and can manifest rapid and selective cytotoxicities towards desired cell types.

Some of the advantageous properties of peptidomimetics for use as antibiotics are described in Srinivas et al. (*Science* 2010, 327, 1010-1013), which is incorporated herein in its entirety.

In an effort to discover peptoid sequences with enhanced antimicrobial activity, a library of benzyl substituted cyclic peptoid oligomers was synthesized. The side chain moieties included in the library contain both direct mimics of peptide side chains and also non-proteinogenic side chains. The inventors demonstrate that the benzyl substituted cyclic peptoid oligomers of the present invention are potent and selective antimicrobials. The optimized peptoid sequences are non-toxic to human red blood cells and show potent antimicrobial activities against both gram positive and gram negative bacterial strains, such as *E. coli, S. aureus*, and *B. subtilis*.

Accordingly, the present inventors have determined that antibiotic benzyl substituted cyclic peptoid oligomers may be prepared that exhibit enhanced stability, due, at least in part, to resistance to enzymatic digestion.

As demonstrated herein, peptoid oligomers of the present invention exhibit antibiotic activity, with minimal host cell toxicity. These findings lead to novel peptoid oligomers that are promising candidates for therapeutic use. It also leads to pharmaceutical compositions comprising the benzyl substituted cyclic peptoids of the present invention as active ingredients and to their use to treat, prevent or ameliorate a range of conditions in mammals of various genesis or etiology, however, primarily caused by bacteria, viruses, or fungi.

More particularly, the present invention relates to peptoid oligomers having antimicrobial properties, according to formula I:

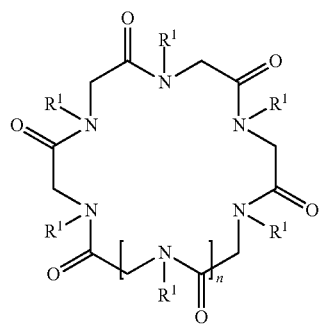

or a pharmaceutically acceptable salt, solvate or prodrug thereof; and stereoisomers, isotopic variants and tautomers thereof;

wherein each $R^1$ is independently fluorenyl, 2-(indol-3-yl)ethyl, or a group selected from

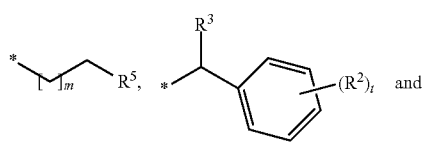

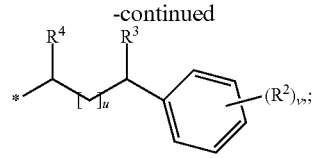

each $R^2$ is independently substituted or unsubstituted alkyl, substituted or unsubstituted phenyl, haloalkyl, halo, substituted or unsubstituted alkoxy, or cyano;

each $R^3$ is independently H, methyl, or phenyl; each $R^4$ is independently H, or methyl;

each $R^5$ is independently —$NR^{6a}R^{6b}$; each $R^{6a}$ and $R^{6b}$ is independently H, substituted or unsubstituted alkyl, or substituted or unsubstituted aryl;

the subscript n is 0 or 1; the subscript m is 0, 1, 2, 3, or 4; the subscript t is 1, 2, 3, 4, or 5; the subscript u is 0, 1, or 2; the subscript v is 0, 1, 2, 3, 4, or 5;

* denotes the attachment point;

and provided that i) at least one of $R^1$s is

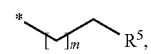

and at least one of $R^1$s is fluorenyl, 2-(indol-3-yl)ethyl, or a group selected from

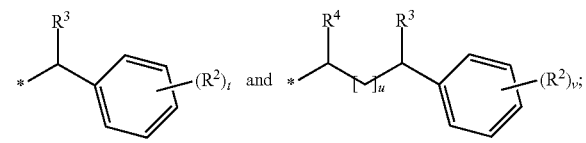

and ii) the compound is other than

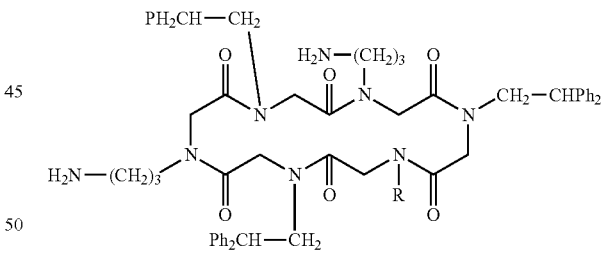

wherein R is —$(CH_2)_3NH_2$,

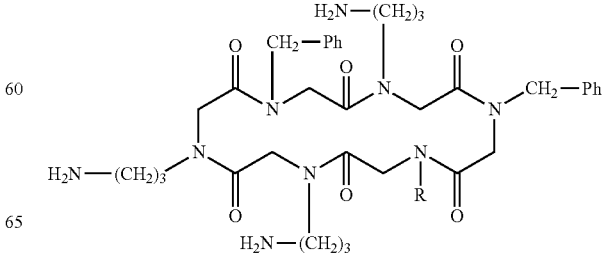

wherein R is —(CH$_2$)$_3$NH$_2$,

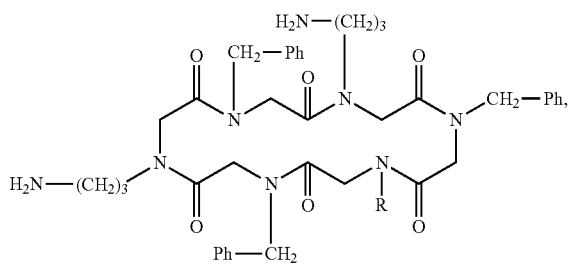

wherein R is —(CH$_2$)$_3$NH$_2$,

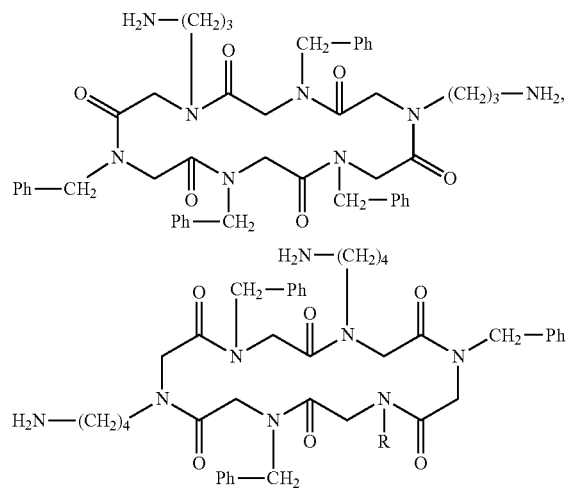

wherein R is —(CH$_2$)$_4$NH$_2$,

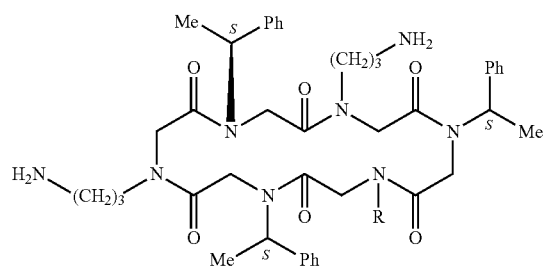

wherein R is —(CH$_2$)$_3$NH$_2$,

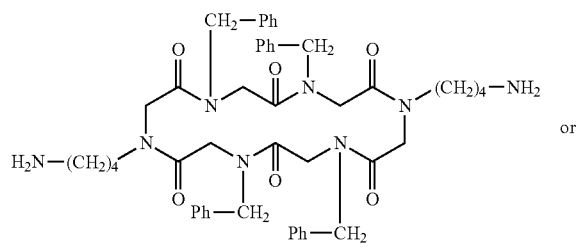

or

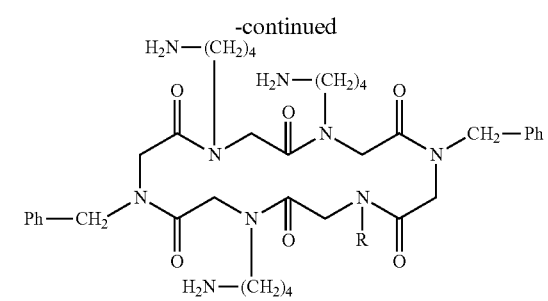

wherein R is —(CH$_2$)$_4$NH$_2$.

In one aspect, the present invention provides benzyl substituted cyclic peptoid oligomers according to the formula I, wherein at least one of the R$^1$s is

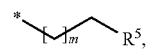

and the rest are selected from

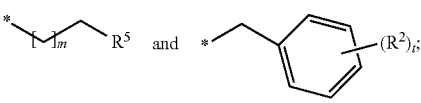

and * denotes the attachment point.

In one aspect, the present invention provides benzyl substituted cyclic peptoid oligomers according to the formula I, wherein at least one of the R$^1$s is

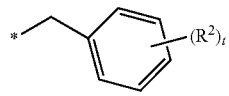

and the rest are selected from

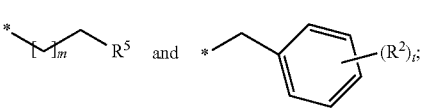

and * denotes the attachment point.

In one particular aspect, the present invention provides benzyl substituted cyclic peptoid oligomers according to the formula I, wherein phenyl of the benzyl is substituted. In one particular embodiment, phenyl is substituted with substituted or unsubstituted alkyl, haloalkyl, halo, substituted or unsubstituted alkoxy, or cyano.

In one particular aspect, the present invention does not include benzyl substituted cyclic peptoids where phenyl of benzyl is unsubstituted.

In one particular aspect, the present invention only includes benzyl substituted cyclic peptoids where phenyl of benzyl is substituted.

In one particular aspect, the present invention does not include 2,2-diphenylethyl substituted cyclic peptoids where phenyl of diphenylethyl is unsubstituted.

In one particular aspect, the present invention does include 1,1-diphenylmethyl substituted cyclic peptoids where phenyl of diphenylmethyl is unsubstituted or substituted.

In one particular aspect, the present invention does include 3,3-diphenylpropyl substituted cyclic peptoids where phenyl of diphenylpropyl is unsubstituted or substituted.

In one particular aspect, the present invention does not include

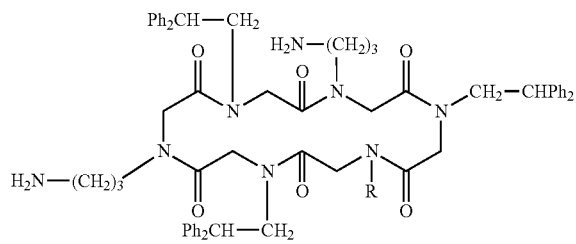

wherein R is —(CH$_2$)$_3$NH$_2$,

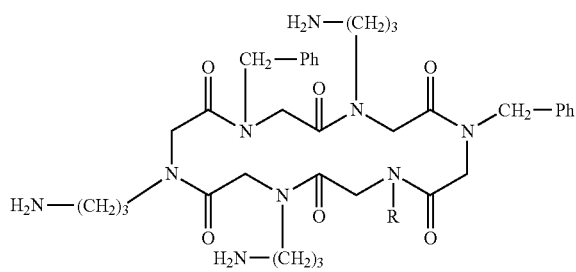

wherein R is —(CH$_2$)$_3$NH$_2$,

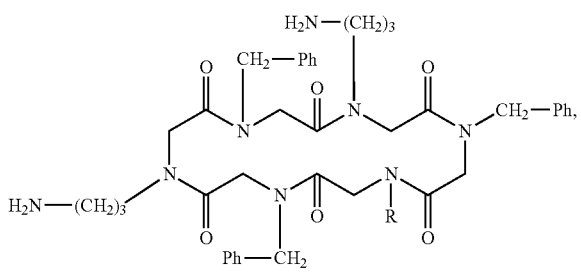

wherein R is —(CH$_2$)$_3$NH$_2$,

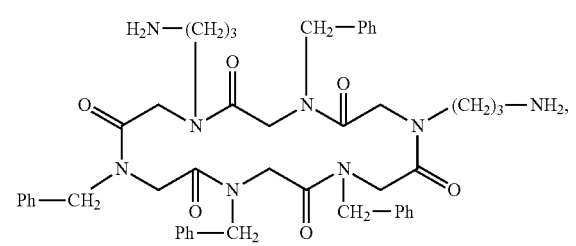

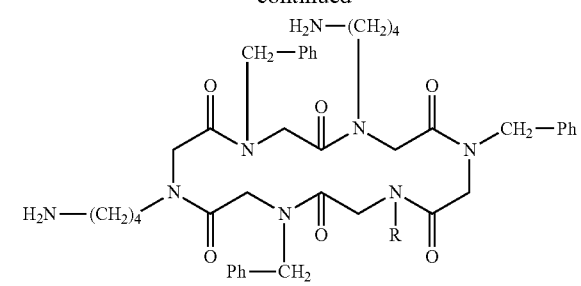

wherein R is —(CH$_2$)$_4$NH$_2$,

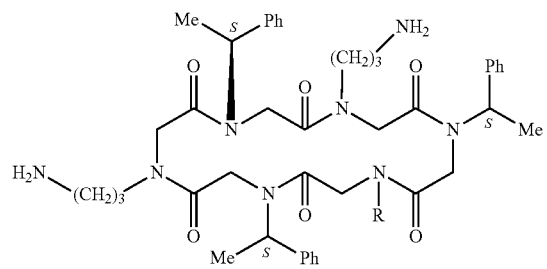

wherein R is —(CH$_2$)$_3$NH$_2$,

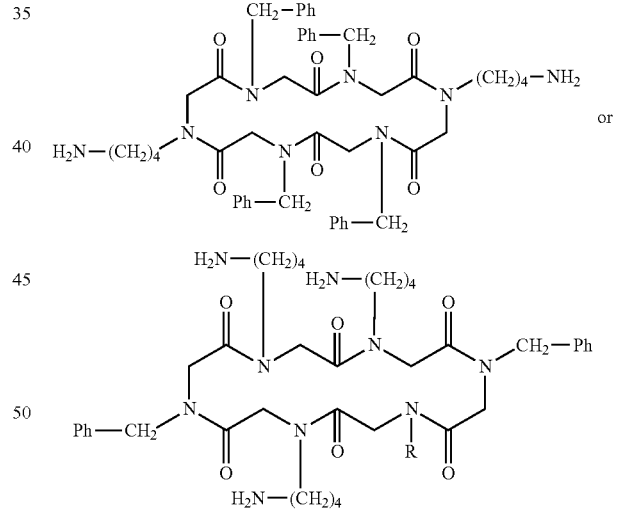

wherein R is —(CH$_2$)$_4$NH$_2$.

In one embodiment, with respect to peptoid oligomers of formula I, when one of R$^1$s is

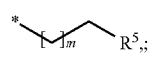

R$^5$ is —NR$^{6a}$R$^{6b}$, and one of R$^{6a}$ and R$^{6b}$ is other than H; then the other R$^1$s may be alkyl or substituted alkyl.

In one embodiment, with respect to peptoid oligomers of formula I, at least one of $R^1$s is

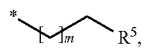

$R^5$ is —$NR^{6a}R^{6b}$, one of $R^{6a}$ and $R^{6b}$ is other than H; and at least one of $R^1$s is substituted or unsubstituted alkyl, fluorenyl, 2-(indol-3-yl)ethyl, or a group selected from

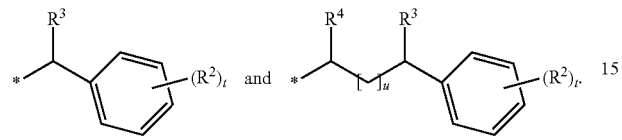

In one embodiment, with respect to peptoid oligomers of formula I, at least one of $R^1$s is

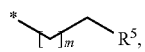

$R^5$ is —$NR^{6a}R^{6b}$, one of $R^{6a}$ and $R^{6b}$ is other than H; and at least one of $R^1$s is Me, Et, n-Pr, Pr, n-Bu, i-Bu, sec-Bu, Ph, or t-Bu.

In one embodiment, with respect to peptoid oligomers of formula I, each of $R^{6a}$ and $R^{6b}$ is independently H.

In one embodiment, with respect to peptoid oligomers of formula I, each of $R^{6a}$ and $R^{6b}$ is independently H, Me, Et, n-Pr, i-Pr, n-Bu, i-Bu, sec-Bu, Ph, benzyl, or t-Bu.

In one embodiment, with respect to peptoid oligomers of formula I, $R^{6a}$ is H; and $R^{6b}$ is independently H, Me, Et, n-Pr, i-Pr, n-Bu, i-Bu, sec-Bu, Ph, benzyl, or t-Bu.

In one embodiment, with respect to peptoid oligomers of formula I, each of $R^{6a}$ and $R^{6b}$ is independently Me.

In one embodiment, with respect to peptoid oligomers of formula I, $R^5$ is —$NR^{6a}R^{6b}$, each of $R^{6a}$ and $R^{6b}$ is other than H; and the oligomer is in the form of a quaternary ammonium salt. In one embodiment, the salt is methiodide. In another embodiment, $R^5$ is $N^+R^{6a}R^{6b}R^{6c}$. $X^-$; and X is a counter ion, such as $Cl^-$, $Br^-$, $I^-$, or $OTs^-$.

In one embodiment, m is 0. In another embodiment, m is 1. In yet another embodiment, m is 2. In yet another embodiment, m is 3. In yet another embodiment, m is 4.

In one embodiment, with respect to peptoid oligomers of formula I, $R^1$ is 2-aminoethyl, 3-aminopropyl, 4-aminobutyl, or 5-aminopentyl.

In one embodiment, with respect to peptoid oligomers of formula I, the subscript n is 0.

In one embodiment, with respect to peptoid oligomers of formula I, the subscript n is 1.

In one embodiment, with respect to peptoid oligomers of formula I, wherein each $R^3$ is independently methyl, or phenyl.

In one embodiment, with respect to peptoid oligomers of formula I, wherein each $R^3$ is independently H.

In one embodiment, with respect to peptoid oligomers of formula I, wherein each $R^4$ is independently methyl.

In one embodiment, with respect to peptoid oligomers of formula I, wherein each $R^4$ is independently H.

In one embodiment, with respect to peptoid oligomers of formula I, wherein two or three of $R^1$s are independently, fluorenyl, or 2-(indol-3-yl)ethyl.

In one embodiment, with respect to peptoid oligomers of formula I, wherein two or three of $R^1$s are independently,

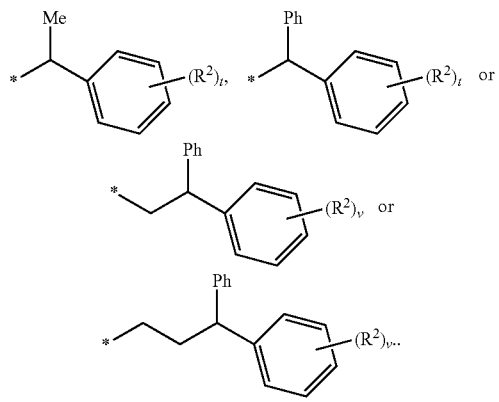

As described herein, * denotes the attachment point.

In one embodiment, with respect to peptoid oligomers of formula I, the oligomer is according to formula IIa or IIb:

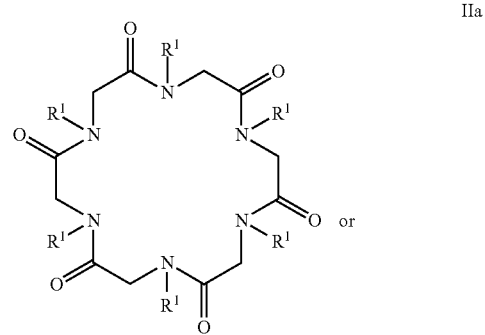

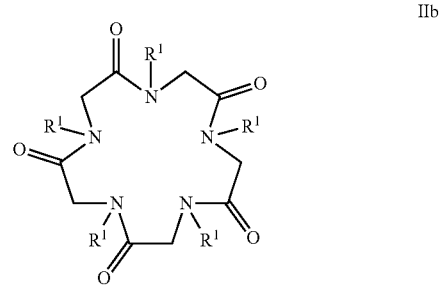

and wherein $R^1$ is as described for formula I.

In one embodiment, with respect to peptoid oligomers of formula I, IIa, and IIb, two of $R^1$s are independently

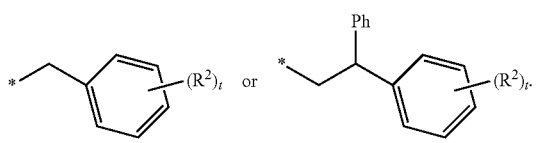

In one embodiment, with respect to peptoid oligomers of formula I, IIa, and IIb, three of $R^1$s are independently

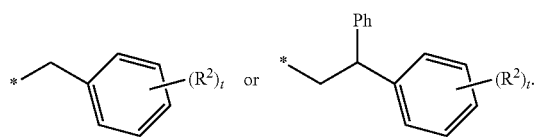

In one embodiment, with respect to peptoid oligomers of formula I, the oligomer is according to formula IIIa, IIIb or IIIc:

IIIa

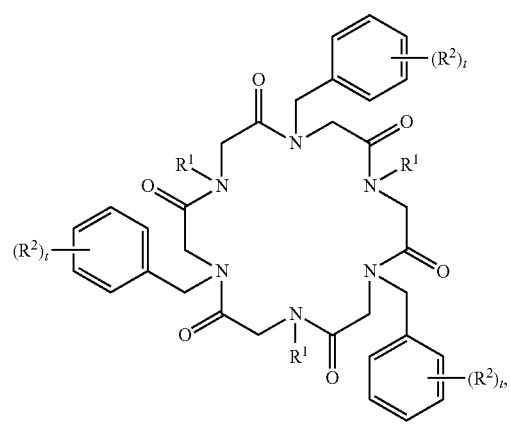

IIIb

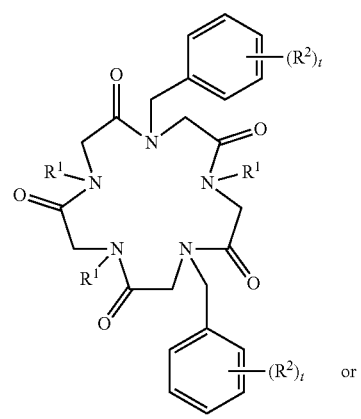

or

IIIc

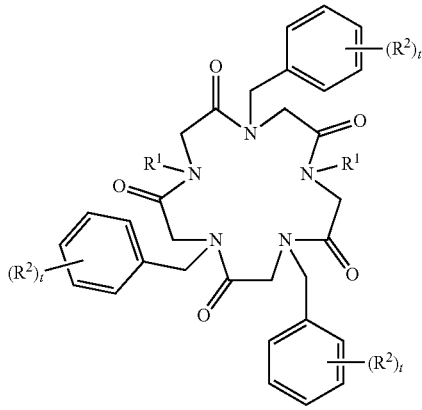

and wherein $R^1$ is

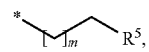

and $R^2$, $R^5$, m and t are as described for formula I.

In one embodiment, with respect to peptoid oligomers of formula I, IIa, and IIb, IIIa, IIIb, and IIIc, the subscript m is 0.

In one embodiment, with respect to peptoid oligomers of formula I, IIa, and IIb, IIIa, IIIb, and IIIc, the subscript m is 1.

In one embodiment, with respect to peptoid oligomers of formula I, IIa, and IIb, IIIa, IIIb, and IIIc, the subscript m is 2.

In one embodiment, with respect to peptoid oligomers of formula I, IIa, and IIb, IIIa, IIIb, and IIIc, the subscript m is 3.

In one embodiment, with respect to peptoid oligomers of formula I, IIa, and IIb, IIIa, IIIb, and IIIc, the subscript m is 4.

In one embodiment, each $R^5$ is independently —$NR^{6a}R^{6b}$; each $R^{6a}$ and $R^{6b}$ is independently H, or substituted or unsubstituted alkyl. In another embodiment, each $R^5$ is $NH_2$.

In one embodiment, with respect to peptoid oligomers of formula I, IIa, and IIb, IIIa, IIIb, and IIIc, $R^1$ is 2-aminoethyl, 3-aminopropyl, 4-aminobutyl, or 5-aminopentyl.

In one embodiment, with respect to peptoid oligomers of formula I, the oligomer is according to formula IVa, IVb or IVc:

IVa

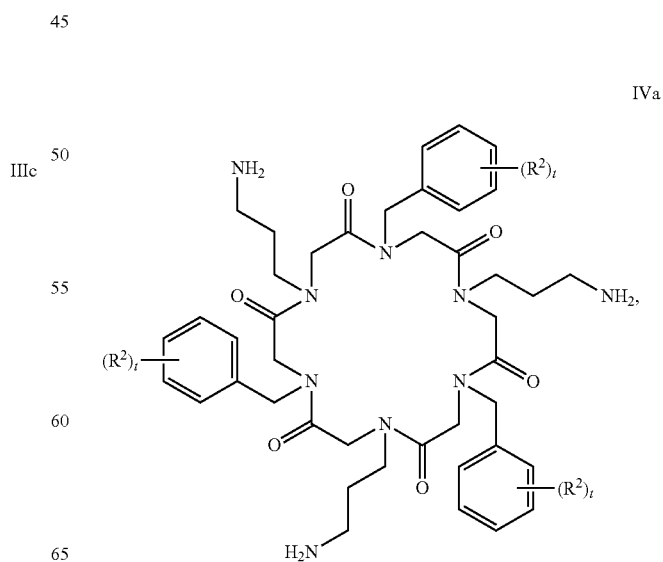

-continued

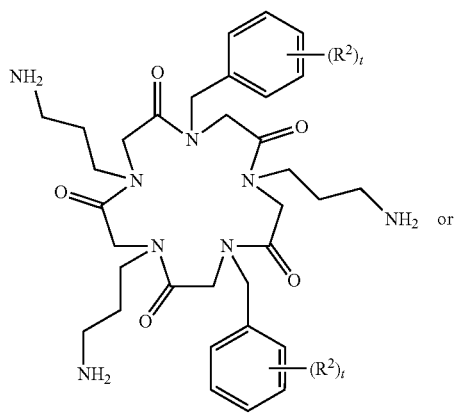

IVb

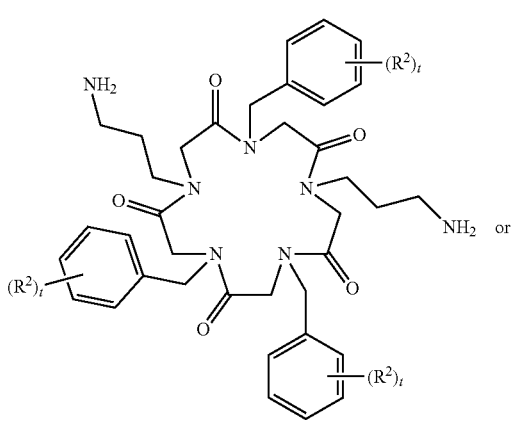

IVc and wherein and R², and t are as described for formula I.

In one embodiment, with respect to peptoid oligomers of formula I, the oligomer is according to formula IVd, IVe or IVf:

IVd

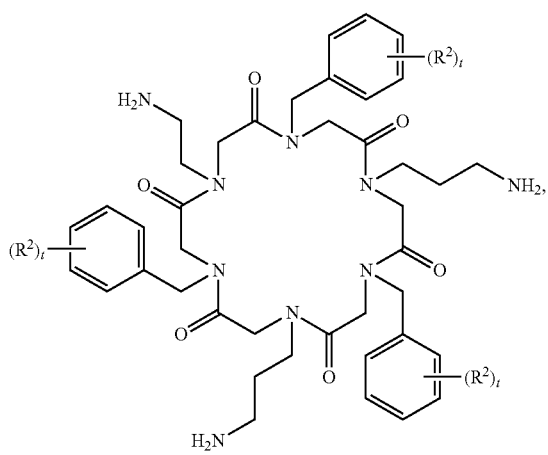

-continued

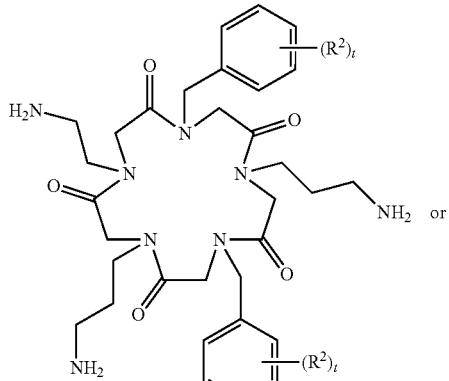

IVe

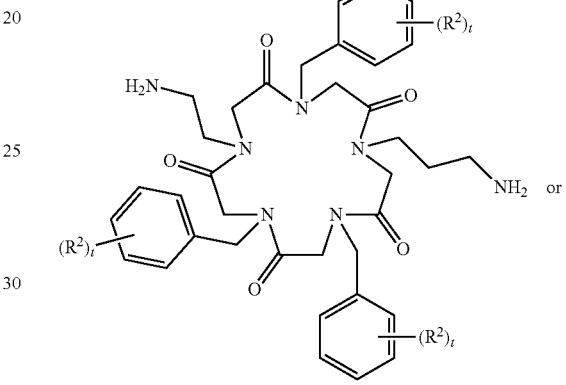

IVf and wherein and R², and t are as described for formula I.

In one embodiment, with respect to peptoid oligomers of formula I, IIa, and IIb, IIIa, IIIb, IIIc, IVa, IVb, IVc, IVd, IVe, and IVf, the subscript t is 1 or 2.

In one embodiment, with respect to peptoid oligomers of formula I, IIa, and IIb, IIIa, IIIb, IIIc, IVa, IVb, IVc, IVd, IVe, and IVf, the subscript t is 3 or 4.

In one embodiment, with respect to peptoid oligomers of formula I, IIa, and IIb, IIIa, IIIb, IIIc, IVa, IVb, IVc, IVd, IVe, and IVf, the subscript t is 5.

In one embodiment, with respect to peptoid oligomers of formula I, IIa, and IIb, IIIa, IIIb, IIIc, IVa, IVb, IVc, IVd, IVe, and IVf, each R² is independently selected from substituted or unsubstituted alkyl, halo, CN, and substituted or unsubstituted alkoxy.

In one embodiment, with respect to peptoid oligomers of formula I, IIa, and IIb, IIIa, IIIb, IIIc, IVa, IVb, IVc, IVd, IVe, and IVf, each R² is independently halo.

In one embodiment, with respect to peptoid oligomers of formula I, IIa, and IIb, IIIa, IIIb, IIIc, IVa, IVb, IVc, IVd, IVe, and IVf, each R² is F.

In one embodiment, with respect to peptoid oligomers of formula I, IIa, and IIb, IIIa, IIIb, IIIc, IVa, IVb, IVc, IVd, IVe, and IVf, each R² is Cl.

In one embodiment, with respect to peptoid oligomers of formula I, IIa, and IIb, IIIa, IIIb, IIIc, IVa, IVb, IVc, IVd, IVe, and IVf, each R² is independently substituted or unsubstituted alkyl.

In one embodiment, with respect to peptoid oligomers of formula I, IIa, and IIb, IIIa, IIIb, IIIc, IVa, IVb, IVc, IVd, IVe, and IVf, each R² is independently is Ph, Me, Et, n-Pr, i-Pr, n-Bu, sec-Bu, or i-Bu.

In one embodiment, with respect to peptoid oligomers of formula I, IIa, and IIb, IIIa, IIIb, IIIc, IVa, IVb, IVc, IVd, IVe, and IVf, each $R^2$ is independently $CF_3$.

In one embodiment, with respect to peptoid oligomers of formula I, IIa, and IIb, IIIa, IIIb, IIIc, IVa, IVb, IVc, IVd, IVe, and IVf, each $R^2$ is independently substituted or unsubstituted alkoxy.

In one embodiment, with respect to peptoid oligomers of formula I, IIa, and IIb, IIIa, IIIb, IIIc, IVa, IVb, IVc, IVd, IVe, and IVf, each $R^2$ is independently OMe, OEt, $OCF_3$, or O-i-Pr.

In one embodiment, with respect to peptoid oligomers of formula I, IIa, and IIb, IIIa, IIIb, IIIc, IVa, IVb, IVc, IVd, IVe, and IVf, t is 1, and $R^2$ is F, Cl, CN, Me or $CF_3$.

In one embodiment, with respect to peptoid oligomers of formula I, IIa, and IIb, IIIa, IIIb, IIIc, IVa, IVb, IVc, IVd, IVe, and IVf, t is 2, and each $R^2$ is independently F, Cl, CN, Me or $CF_3$.

In one embodiment, with respect to peptoid oligomers of formula I, the oligomer is according to formula Va, Vb or Vc:

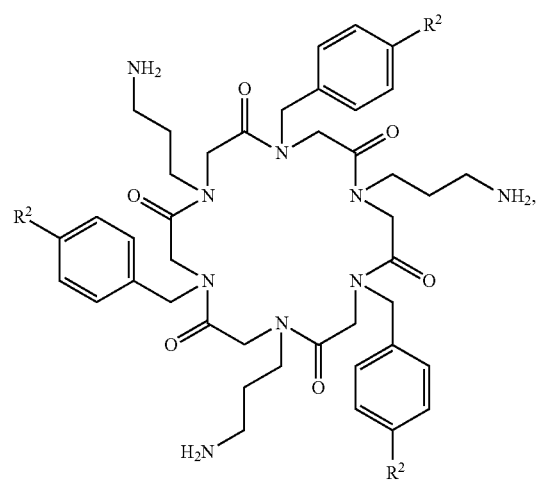

Va

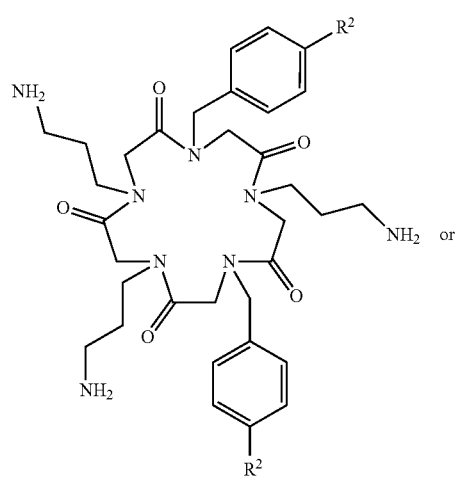

Vb

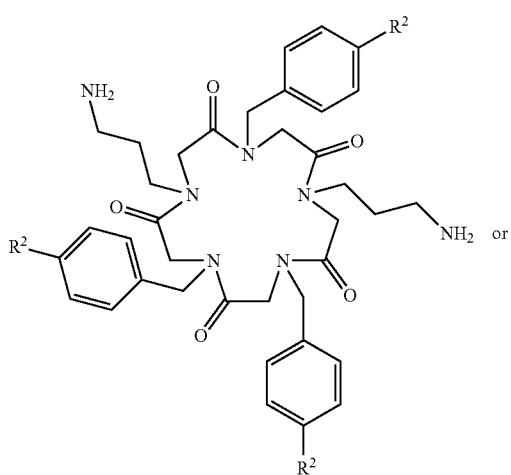

Vc and wherein $R^2$ is as described for formula I.

In one embodiment, with respect to peptoid oligomers of formula I, the oligomer is according to formula Vd, Ve or Vf:

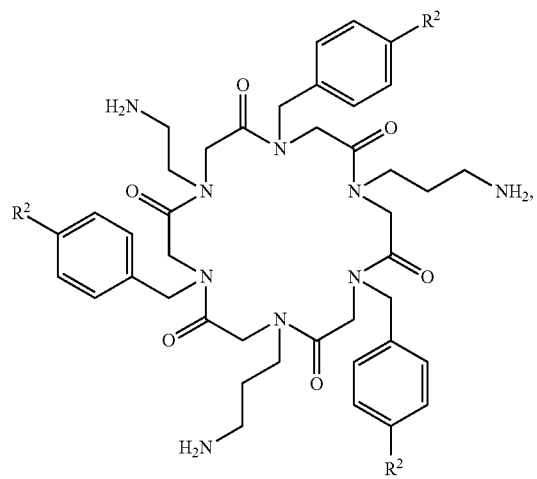

Vd

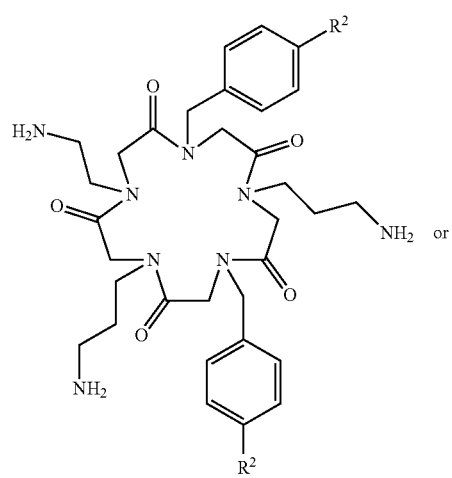

Ve

-continued

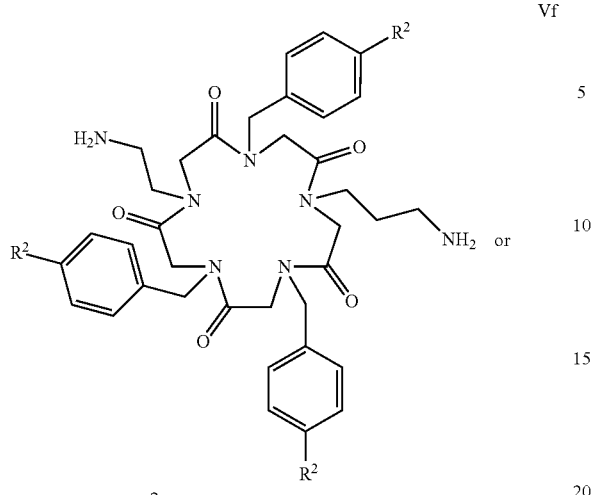

Vf and wherein $R^2$ is as described for formula I.

In one embodiment, with respect to peptoid oligomers of formula Va, Vb, Vc, Vd, Ve or Vf, $R^2$ is Cl, F, $CF_3$, CN, OMe, OEt, O-i-Pr, Ph, Me, Et, n-Pr, i-Pr, n-Bu, sec-Bu, or i-Bu.

In one embodiment, with respect to peptoid oligomers of formula Va, Vb, Vc, Vd, Ve or Vf, $R^2$ is Cl, F, $CF_3$, or Me.

In one embodiment, with respect to peptoid oligomers of formula I, the oligomer is according to formula VIa, VIb or VIc:

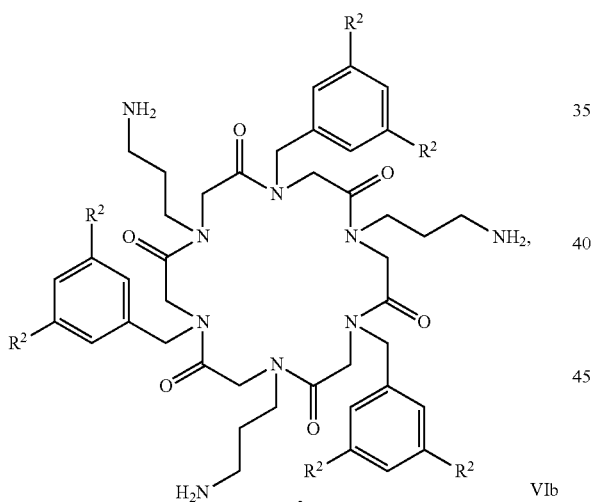

VIa

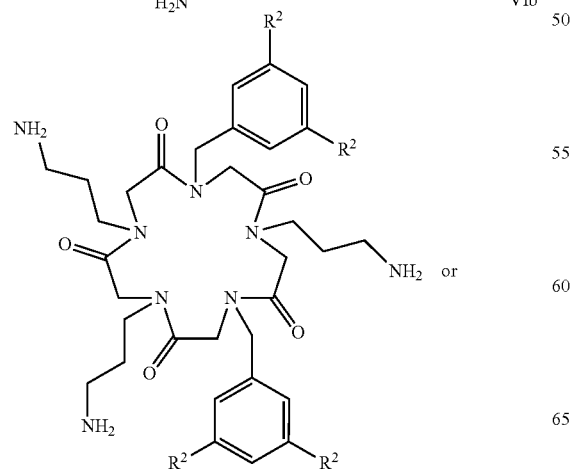

VIb

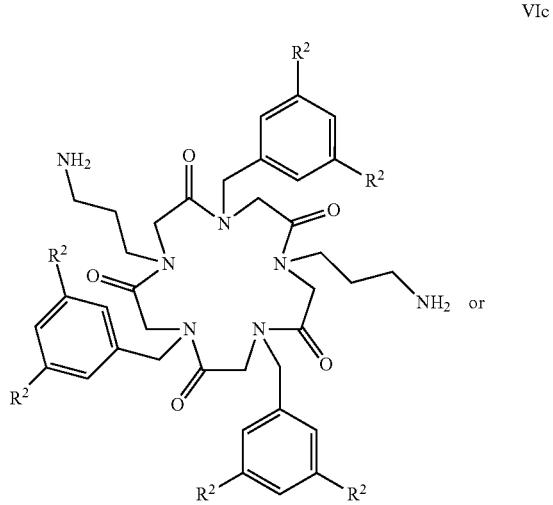

VIc and wherein $R^2$ is as described for formula I.

In one embodiment, with respect to peptoid oligomers of formula I, the oligomer is according to formula VId, VIe or VIf:

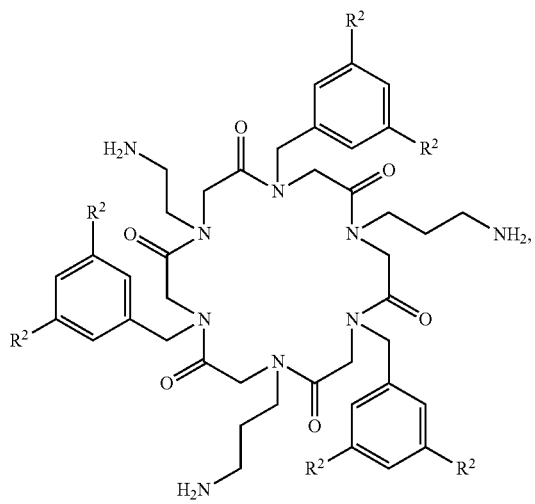

VId

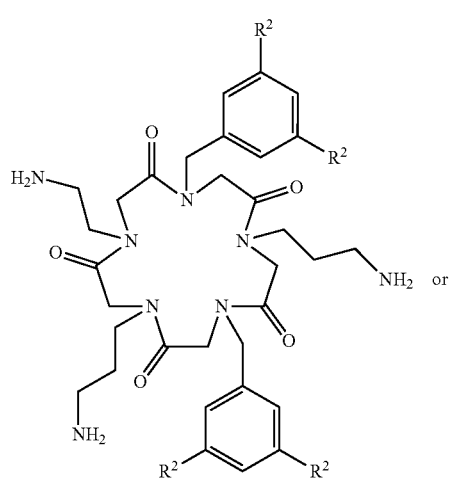

VIe

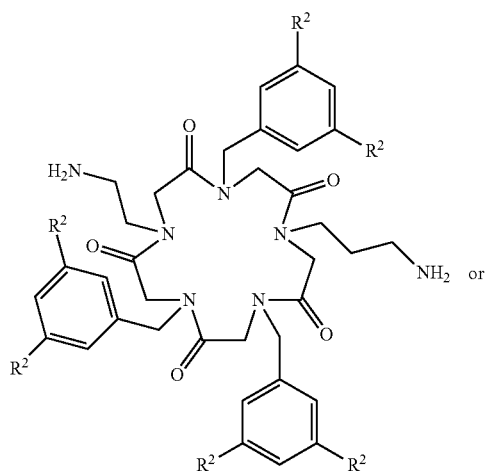

VIf and wherein R² is as described for formula I.

In one embodiment, with respect to peptoid oligomers of formula VIa, VIb, VIc, VId, VIe or VIf, each R² is independently Cl, F, CF₃, CN, OMe, OEt, O-i-Pr, Me, Et, n-Pr, i-Pr, n-Bu, sec-Bu, or i-Bu.

In one embodiment, with respect to peptoid oligomers of formula VIa, VIb, VIc, VId, VIe or VIf, each R² is independently Cl, F, CF₃, or Me.

In one embodiment, with respect to peptoid oligomers of formula VIa, VIb, VIc, VId, VIe or VIf, each R² is CF₃.

In one embodiment, with respect to peptoid oligomers of formula VIa, VIb, VIc, VId, VIe or VIf, each R² is Me.

In one embodiment, with respect to peptoid oligomers of formula I, the oligomer is according to formula VIIa, VIIb or VIIc:

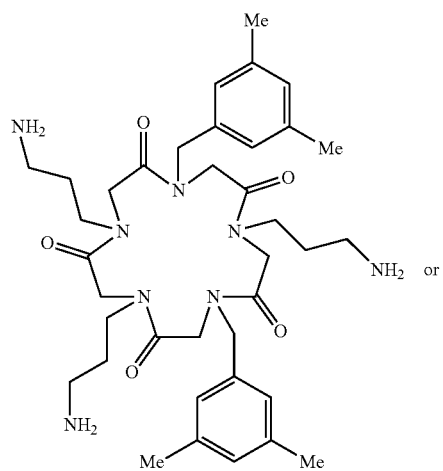

VIIb

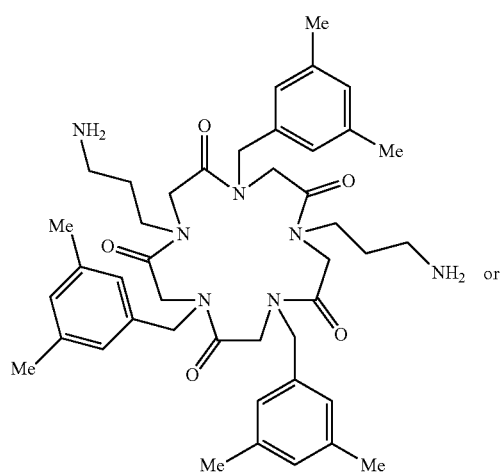

VIIc

In one embodiment, with respect to peptoid oligomers of formula I, the oligomer is according to formula VIId, VIIe or VIIf:

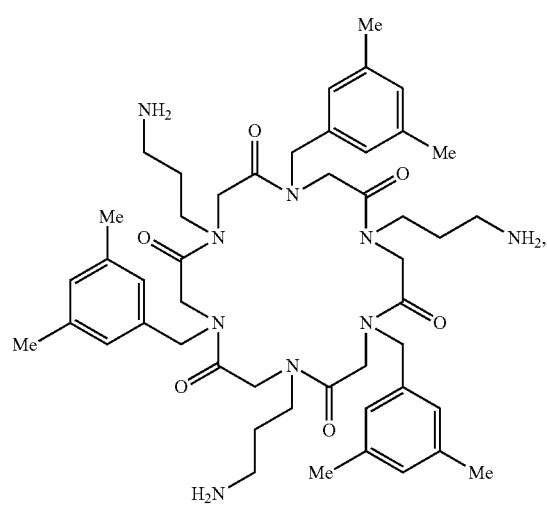

VIIa

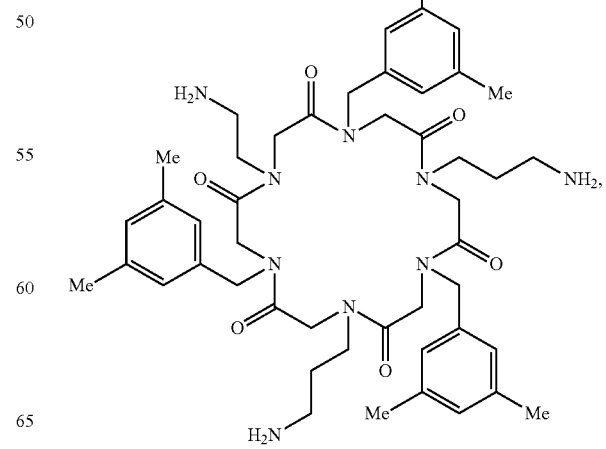

VIId

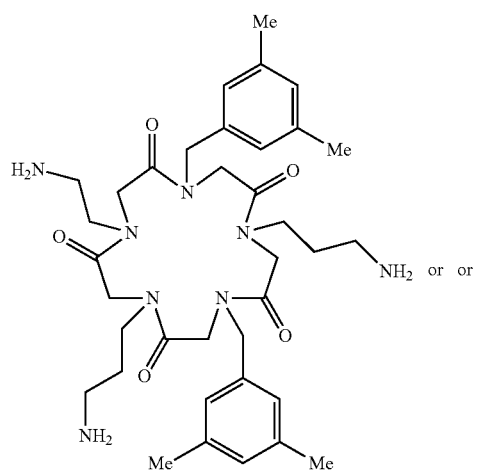
VIIe
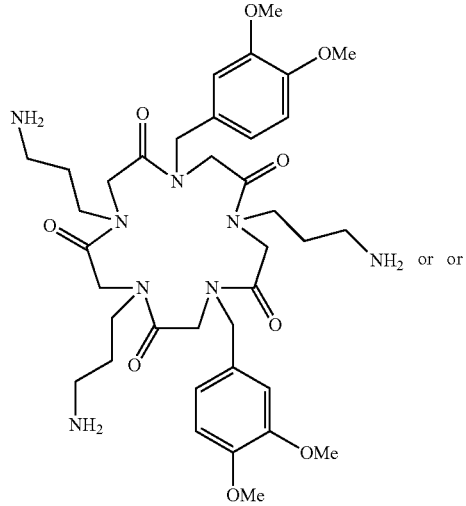
VIIIb
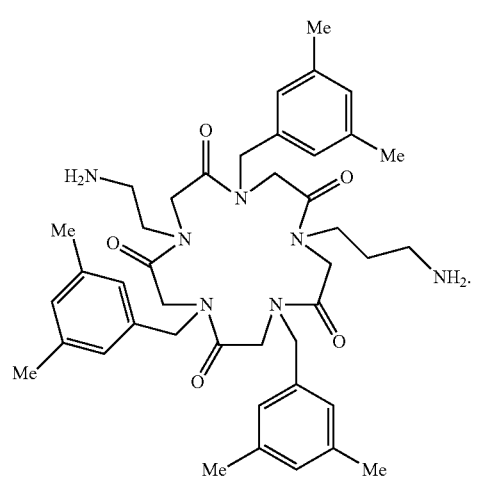
VIIf
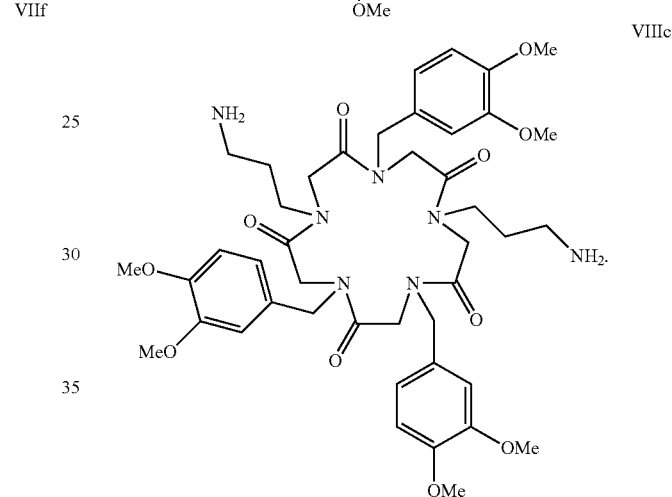
VIIIc
In one embodiment, with respect to peptoid oligomers of formula I, the oligomer is according to formula VIIIa, VIIIb or VIIIc:
In one embodiment, with respect to peptoid oligomers of formula I, the oligomer is according to formula VIIId, VIIIe or VIIIf:
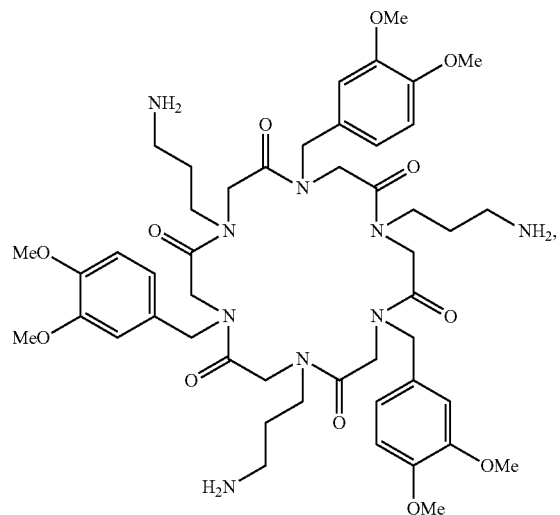
VIIIa
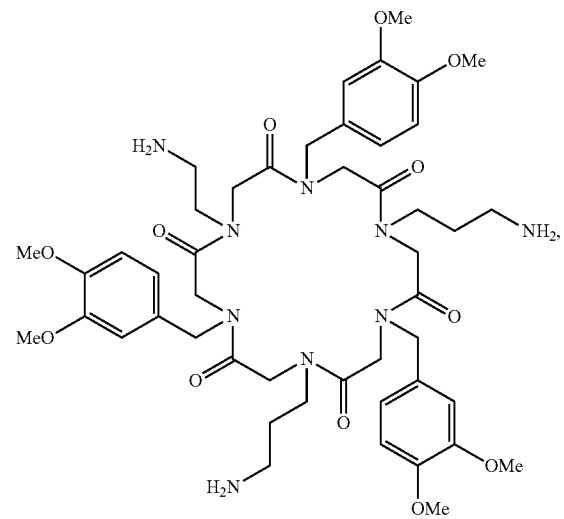
VIIId

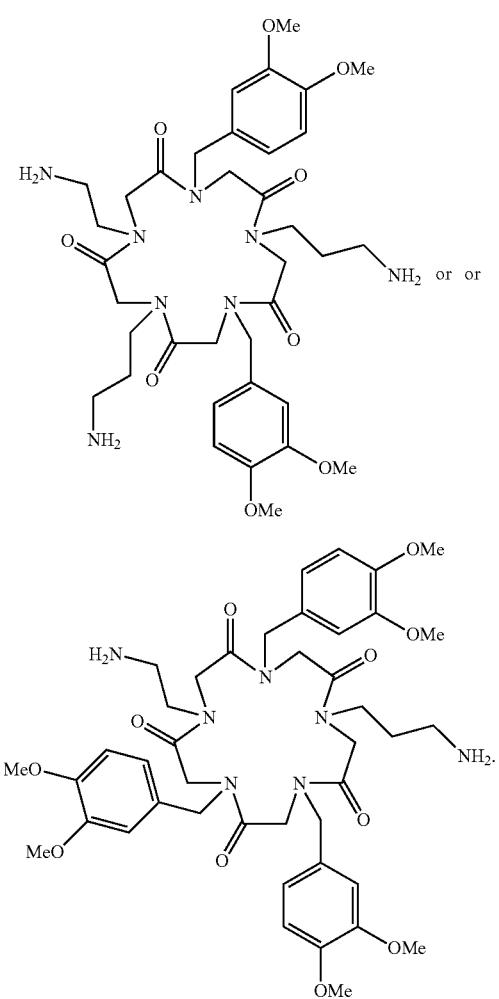

In one embodiment, with respect to peptoid oligomers of formula IVa-IVc, Va-Vc, VIa-VIc, VIIa-VIIc, or VIIIa-VIIIc, the —NH$_2$ group is replaced with alkylamino, or dialkylamino. In one embodiment, alkyl is Me, Et, n-Pr, i-Pr, n-Bu, i-Bu, sec-Bu, Ph, or t-Bu.

In one embodiment, with respect to peptoid oligomers of formula IVa-IVc, Va-Vc, VIa-VIc, VIIa-VIIc, or VIIIa-VIIIc, the —NH$_2$ group is replaced with —NMe$_2$, NHMe, —NEt$_2$. In another embodiment, the —NH$_2$ group is replaced with —N$^+$Me$_3$.X$^-$; and X$^-$ is Cl$^-$, Br$^-$, I$^-$ or OTs$^-$.

In one embodiment, with respect to peptoid oligomers of formula Ia or Ib, the peptoid oligomer is selected from the oligomers listed in Table 1, provided the compound or oligomer is C122, C123, C124 or C125.

In one embodiment, with respect to peptoid oligomers of formula Ia or Ib, the peptoid oligomer is selected from the oligomers listed in FIG. 11, provided the compound or oligomer is C103, C104, C105, C106, C117, or C121.

In one embodiment, with respect to peptoid oligomers of formula Ia or Ib, the peptoid oligomer is selected from the oligomers listed in FIG. 11, and the compound is C122.

In one embodiment, with respect to peptoid oligomers of formula Ia or Ib, the peptoid oligomer is selected from the oligomers listed in FIG. 11, and the compound is C123.

In one embodiment, with respect to peptoid oligomers of formula Ia or Ib, the peptoid oligomer is selected from the oligomers listed in FIG. 11, and the compound is C124.

In one embodiment, with respect to peptoid oligomers of formula Ia or Ib, the peptoid oligomer is selected from the oligomers listed in FIG. 11, and the compound is C125.

In one embodiment, with respect to peptoid oligomers of formula Ia or Ib, the peptoid oligomer is selected from the oligomers listed in FIG. 11, and the compound is C103.

In one embodiment, with respect to peptoid oligomers of formula Ia or Ib, the peptoid oligomer is selected from the oligomers listed in FIG. 11, and the compound is C104.

In one embodiment, with respect to peptoid oligomers of formula Ia or Ib, the peptoid oligomer is selected from the oligomers listed in FIG. 11, and the compound is C105.

In one embodiment, with respect to peptoid oligomers of formula Ia or Ib, the peptoid oligomer is selected from the oligomers listed in FIG. 11, and the compound is C106.

In one embodiment, with respect to peptoid oligomers of formula Ia or Ib, the peptoid oligomer is selected from the oligomers listed in FIG. 11, and the compound is C117.

In one embodiment, with respect to peptoid oligomers of formula Ia or Ib, the peptoid oligomer is selected from the oligomers listed in FIG. 11, and the compound is C5-1.

In one particular aspect, the present invention discloses novel peptoid oligomers, and novel peptoid oligomers selected from oligomers C(1-3), C(1-4), C(1-11), and C(1-14).

In certain aspects and where appropriate, the present invention extends to the preparation of prodrugs and derivatives of the peptoids of the invention. Prodrugs are derivatives which have cleavable groups and become by solvolysis or under physiological conditions the peptoid of the invention, which are pharmaceutically active, in vivo.

In one embodiment, the invention provides a pharmaceutical composition comprising a pharmaceutically acceptable carrier and a pharmaceutically effective amount of the peptoid of formula I.

In one embodiment, the invention provides a pharmaceutical composition of the peptoid of formula I, comprising a pharmaceutically acceptable carrier, and the carrier is a parenteral carrier, oral or topical carrier.

In one embodiment, the invention provides a method for preventing, treating, ameliorating or managing a disease or condition which comprises administering to a patient in need of such prevention, treatment, amelioration or management, a prophylactically or therapeutically effective amount of the pharmaceutical composition of the peptoid of formula I.

In one embodiment, the disease or condition is or results from a bacterial infection.

In one embodiment, the disease or condition is or results from infection with gram positive or gram negative bacterial strains. The compositions of the present invention can be used to kill or inhibit the growth of any of the following microbes or mixtures of the following microbes, or, alternatively, can be administered to treat local and/or systemic microbial infections or illnesses caused by the following microbes or mixtures of the following microbes: Gram-positive cocci, for example *Staphylococci* (*Staph. aureus, Staph. epidermidis*) and *Streptococci* (*Strept. agalactiae, Strept. faecalis, Strept. pneumoniae, Strept. pyogenes*); Gram-negative cocci (*Neisseria gonoirhoeae* and *Yersinia pestis*) and Gram-negative rods such as Enterobacteriaceae, for example *Escherichia coli, Hamophilus influenzae, Citrobacter* (*Citrob. freundii, Citrob. divernis*), *Salmonella* and *Shigella*, and *Francisella* (*Francisella tularensis*); Gram-positive rods such as *Bacillus* (*Bacillus anthracis, Bacillus thuringenesis*); furthermore *Klebsiella* (*Klebs. pneumoniae, Klebs. oxytoca*), *Enterobacter* (*Ent. aerogenes, Ent. agglomerans*), *Hafnia, Serratia* (*Serr. marcescens*), *Proteus* (*Pr.*

*mirabilis, Pr. rettgeri, Pr. vulgaris*), *Providencia, Yersinia*, the genus *Acinetobacter*, and the genus *Brevibacterium*, including *Brevibacterium linens*, which is ubiquitously present on human skin and is the causative agent of foot odor. Furthermore, the antimicrobial spectrum of the peptoid oligomers of the present invention covers the genus *Pseudomonas* (*Ps. aeruginosa, Ps. maltophilia*), the aerotolerant anaerobic gram positive bacterium *Propionibacterium acnes* (*P. acnes*), which is causatively linked to skin acne, and strictly anaerobic bacteria such as, for example, *Bacteroides fragilis*, representatives of the genus *Peptococcus, Peptostreptococcus* and the genus *Clostridium*; furthermore *Mycoplasmas* (*M. pneumoniae, M. hominis, Ureaplasma urealyticum*) as well as Mycobacteria, for example *Mycobacterium tuberculosis*. This list of microbes is purely illustrative and is in no way to be interpreted as restrictive.

In one embodiment, the disease or condition is or results from Methicillin-resistant *Staphylococcus aureus* (MRSA).

Examples of microbial infections or illness that can be treated by administration of the composition of the present invention include, but are not limited to, microbial infections or illnesses in mammals (e.g., humans) such as, for example, otitis, pharyngitis, pneumonia, peritonitis, pyelonephritis, cystitis, endocarditis, systemic infections, bronchitis (acute and chronic), sepsis, illnesses of the upper airways, diffuse panbronchiolitis, pulmonary emphysema, dysentery, enteritis, liver abscesses, urethritis, prostatitis, epididymitis, gastrointestinal infections, bone and joint infections, infections arising in patients afflicted with cystic fibrosis, skin infections, postoperative wound infections, abscesses, phlegmon, wound infections, infected burns, burns, infections in the mouth (including, e.g., but not limited to, periodontal disease and gingivitis), infections after dental operations, osteomyelitis, septic arthritis, cholecystitis, peritonitis with appendicitis, cholangitis, intraabdominal abscesses, pancreatitis, sinusitis, mastoiditis, mastitis, tonsileitis, typhoid, meningitis and infections of the nervous system, salpingitis, endometritis, genital infections, pelveoperitonitis and eye infections.

In one embodiment, the disease or condition is or results from a viral infection. Examples of viral infections that can be treated by administration of the peptoid oligomers of the present invention include, but are not limited to, viral infections caused by human immunodeficiency virus (HIV-1, HIV-2), hepatitis virus (e.g., hepatitis A, hepatitis B, hepatitis C, hepatitis D, and hepatitis E viruses), herpesviruses (e.g. herpes simplex virus types 1 and 2, varicellazoster virus, cytomegalovirus, Epstein Barr virus, and human herpes viruses types 6, 7, and 8), influenza virus, respiratory syncytial virus (RSV), vaccinia virus, and adenoviruses. This list is purely illustrative and is in no way to be interpreted as restrictive.

It will be appreciated by skilled practitioners that subjects suffering from viral illnesses frequently succumb to secondary bacterial and/or fungal infections. Accordingly, in an embodiment of the invention pertaining to treating a disease or condition associated with a viral infection, an attending physician will be monitoring the patient for signs indicating the onset of such a secondary infection.

In one embodiment, the disease or condition is or results from a fungal infection. Examples of fungal infections or illnesses that can be treated by administration of the compositions of the present invention include, but are not limited to, fungal infections caused by *Chytridiomycetes, Hyphochrytridiomycetes, Plasmodiophoromycetes, Oomycetes, Zygomycetes, Ascomycetes*, and *Basidiomycetes*. Fungal infections which can be inhibited or treated with compositions of the peptoid oligomers provided herein include, but are not limited to: *Candidiasis*, including, but not limited to, onchomycosis, chronic mucocutaneous candidiasis, oral candidiasis, epiglottistis, esophagitis, gastrointestinal infections, genitourinary infections, for example, caused by any *Candida* species, including, but not limited to, *Candida albicans, Candida tropicalis, Candida* (*Torulopsis*) *glabrata, Candida parapsilosis, Candida lusitaneae, Candida rugosa* and *Candida pseudo tropicalis; Aspergillosis*, including, but not limited to, granulocytopenia caused, for example, by, *Aspergillus* spp. Including, but not limited, to *Aspergillus fumigatus, Aspergillus favus, Aspergillus niger* and *Aspergillus terreus; Zygomycosis*, including, but not limited to, pulmonary, sinus and rhinocerebral infections caused by, for example, zygomycetes such as *Mucor, Rhizopus* spp., *Absidia, Rhizomucor, Cunningamella, Saksenaea, Basidobolus* and *Conidobolus; Cryptococcosis*, including, but not limited, to infections of the central nervous system, e.g., meningitis, and infections of the respiratory tract caused by, for example, *Cryptococcus neoformans*; Trichosporonosis caused by, for example, *Trichosporon beigelii*; Pseudallescheriasis caused by, for example, *Pseudallescheria boydii; Fusarium* infection caused by, for example, *Fusarium* such as *Fusarium solani, Fusarium moniliforme* and *Fusarium proliferartum*; and other infections such as those caused by, for example, *Penicillium* spp. (generalized subcutaneous abscesses), *Trichophyton* spp., for example, *Trichophyton mentagrophytes* and *Trichophyton rubrum, Stachybotrys* spp., for example, *S. chartarum, Drechslera, Bipolaris, Exserohilum* spp., *Paecilomyces lilacinum, Exophila jeanselmei* (cutaneous nodules), *Malassezia furfur* (folliculitis), *Alternaria* (cutaneous nodular lesions), *Aureobasidium pullulans* (splenic and disseminated infection), *Rhodotorula* spp. (disseminated infection), *Chaetomium* spp. (empyema), *Torulopsis candida* (fungemia), *Curvularia* spp. (nasopharnygeal infection), *Cunninghamella* spp. (pneumonia), *H. Capsulatum, B. dermatitidis, Coccidioides immitis, Sporothrix schenckii* and *Paracoccidioides brasiliensis, Geotrichum candidum* (disseminated infection). The compositions of the present invention can also be used to kill or inhibit the growth of any of the fungi listed above. This list is purely illustrative and is in no way to be interpreted as restrictive.

In one embodiment, the invention provides a method of using pharmaceutical composition of peptoid of formula I, to generation of antiseptic or sterile environment.

In one embodiment, the invention provides a method for preventing, treating, ameliorating or managing a disease or condition, which comprises administering to a patient in need of such prevention, treatment, amelioration or management a prophylactically or therapeutically acceptable amount of a peptoid of formula I, or the pharmaceutical composition thereof, wherein the disease or condition results from or is caused by bacterial infection, viral infection or fungal infection.

Pharmaceutical Compositions

When employed as pharmaceuticals, the peptoid compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the peptoid compounds in combination with one or more non-peptoid antibiotic compounds, including known antibiotic compounds.

Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the peptoid compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, rectal, vaginal, transdermal, subcutaneous, intravenous, intramuscular, intrathecal, and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The present complexes may be used as therapeutic agents for the treatment of conditions in mammals. Accordingly, the complexes and pharmaceutical compositions of this invention find use as therapeutics for preventing and/or treating infections and like maladies resulting from bacterial, viral or fungal attack, and related conditions in mammals, including humans. Thus, and as stated earlier, the present invention includes within its scope, and extends to, the recited methods of treatment, as well as to the compounds for such methods, and the compounds for use in treating infections and like maladies resulting from the presence of bacterial, viral or fungal in a subject, and to the use of such compounds for the preparation of medicaments for treating such conditions and like maladies in a subject.

In a method of treatment aspect, the invention presents a method for treating a mammal susceptible to or afflicted with a condition associated with or resulting from bacterial, viral or fungal attack or infection, which method comprises administering an effective amount of one or more of the pharmaceutical compositions just described.

The methods disclosed herein have veterinary applications and can be used to treat a wide variety of non-human vertebrates. Thus, in other aspects of the invention, the compositions of the present invention are administered in the above methods to non-human vertebrates, such as wild, domestic, or farm animals, including, but not limited to, cattle, sheep, goats, pigs, dogs, cats, and poultry such as chicken, turkeys, quail, pigeons, ornamental birds and the like.

The following are examples of microbial infections in non-human vertebrates that can be treated by administering a composition of the present invention: Pig: coli diarrhoea, enterotoxaemia, sepsis, dysentery, salmonellosis, metritis-mastitis-agalactiae syndrome, mastitis; ruminants (cattle, sheep, goat): diarrhoea, sepsis, bronchopneumonia, salmonellosis, pasteurellosis, mycoplasmosis, genital infections, mastitis; horse: bronchopneumonias, joint ill, puerperal and post-puerperal infections, salmonellosis; dog and cat: bronchopneumonia, diarrhoea, dermatitis, otitis, urinary tract infections, prostatitis; poultry (chicken, turkey, quail, pigeon, ornamental birds and others): mycoplasmosis, *E. coli* infections, chronic respiratory tract illnesses, salmonellosis, pasteurellosis, psittacosis. This list is purely illustrative and is in no way to be interpreted as restrictive.

In additional method of treatment aspects, this invention provides methods of treating a mammal susceptible to or afflicted with a variety of bacteria or other infections, including strains which have developed resistance to traditional antibiotics, such as, for example, *Staphylococcus aureus*. The method comprises administering an effective condition-treating or condition-preventing amount of one or more of the pharmaceutical compositions just described.

The peptoid antimicrobials of the invention may also be used in preventive or prophylactic applications, wherein the peptoid antimicrobials are administered to a subject for preventive purposes (i.e., administered to a subject in advance of exposure to a disease causing entity) individually or as a combination of different peptoid antimicrobials. The peptoid antimicrobials of the invention can also be used in combination with antibiotics administered in a preventive application. A number of antibiotics are used clinically to reduce the risk of contracting bacterial, viral, and/or fungal infections. Ideally such preventive or prophylactic administration prevents infection.

In general, prophylactic administration of antibiotics is recommended only in certain situations or for people with particular medical problems. People with abnormal heart valves, for example, have a high risk of developing heart valve infections even after minor surgery. Such infections occur because bacteria from other parts of the body can enter the bloodstream during surgical procedures and travel to the heart valves. To prevent these infections, people with abnormal heart valves often take antibiotics before having any kind of surgery, including dental surgery.

Antibiotics may also be prescribed to prevent infections in people with weakened immune systems such as those with Acquired Immune Deficiency Syndrome (AIDS) or people who are having chemotherapy treatments for cancer. Even healthy people with strong immune systems, however, may occasionally be given preventive antibiotics if they are scheduled to have surgery that is associated with a high risk of infection, or if they are traveling to parts of the world where they are likely to contract an infection that causes, for example, diarrhea.

Drugs used for antibiotic prophylaxis include: amoxicillin (a type of penicillin) and fluoroquinolones such as ciprofloxacin (Cipro) and trovafloxacin (Trovan). These drugs are available in tablet, capsule, liquid, and injectable forms. Other antibiotics used for prophylactic purposes are known to those skilled in the art.

The following list presents particular embodiments wherein antibiotics are used for preventive purposes, wherein the peptoid antimicrobials of the invention may also be used to advantage either alone or in combination with prophylactic antibiotics. For malaria prophylaxis, clinicians prescribe 100 mg (e.g., doxycycline) by mouth daily 1-2 weeks prior to travel then 4 weeks after travel. For AIDS patients, *pneumocystis carinii* pneumonia prophylaxis is recommended and generally involves administration of Bactrim (trimethoprim-sulfamethoxazole), double strength tablet, one tablet by mouth daily. For AIDS patients, suppression of cryptococcal meningitis relapse is recommended and generally involves administration of fluconazole, 200 mg daily. Patients with other immunocompromising conditions (e.g., bone marrow transplant patients and neutropenic patients on chemotherapy) are also prescribed prophyactic oral antibiotics to prevent opportunistic infections by common fungal or bacterial agents.

For surgical prophylaxis, the cephalosporin antibiotics are usually preferred. This class includes cefazolin (Ancef, Kefzol), cefamandole (Mandol), cefotaxime (Claforan), and others. The choice of drug depends on its spectrum and the type of bacteria that are most likely to be encountered.

Surgery on the intestines, for example, which are filled with many anaerobic bacteria, might call for cefoxitin (Mefoxin), while in heart surgery, where there are no anaerobes, cefazolin might be preferred.

The following list presents particular embodiments wherein antibiotics are used for surgical prophylaxis, wherein the peptoid antimicrobials of the invention may also be used to advantage either alone or in combination with prophylactic antibiotics. For patients with valvular heart disease, patients with a history of any valvular heart disease may be administered oral amoxicillin prior to dental work. Patients with a history of major valvular heart disease (like a valve replacement) may be administered iv antibiotics (usually ampicillin, 1 gram every 6 hours and gentamicin 80 mg every 8 hours) prior to, during and after major abdominal surgery.

As pre-operative antibiotics, any patient having abdominal surgery may be treated with antibiotics intravenously (iv). Typically, patients receive one dose of a cephalosporin (Cefotetan, Cefoxitin, etc.), about 1 gram iv. For heavy intra-operative bleeding or operations lasting longer than 4 hours, another dose of iv antibiotics may be given and, in extended use, iv antibiotics may be administration for 24 hours after the operation. For bowel surgery, general surgeons will frequently administer iv Ciprofloxacin 400 mg and Metronidazole 500 mg. In cases of emergency surgery, post-operative antibiotics are usually given to prevent infection. In all cases, the antibiotic administered is determined by the attending medical practitioner, based on experience as to which microbial agents the patient is most likely to be exposed.

A skilled practitioner would appreciate applications wherein the peptoid antimicrobials of the invention may be used to advantage, alone or in conjunction with antibiotics for prophylactic purposes. In a particular embodiment, peptoid antimicrobials of the invention may be administered alone or in conjunction with antibiotics for preventing bacterial infections.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as those associated with persistent viral or microbial conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

The complexes of this invention can be administered as the sole active agent or they can be administered in combination with other agents, including other active derivatives.

A skilled practitioner would appreciate that the choice as to which compound or compounds of the invention are well suited to a particular application must take into consideration such variables as the severity of the disease or condition, mode of administration, and duration of administration.

Antimicrobial Substrates

The benzyl substituted cyclic peptoid oligomers of the present invention and compositions thereof may also be bound to or incorporated into substrates to provide antimicrobial substrates to reduce or inhibit microbial contamination of the substrate. The present invention also provides articles comprising the antimicrobial substrates of the invention.

As indicated above, a skilled practitioner would take into consideration such variables as the likelihood of microbial contamination of a substrate prior to or during use, risks associated with microbial contamination in a subject using a substrate, and duration of use.

Substrates suitable for the present invention include conventional polymers selected from the group consisting of latex, polyvinyl chloride, polyimide, polyesters, polyethylene, polypropylene, polyamides, polyacrylates, polyolefins, polysaccharides, polyurethane, polysulfone, polyethersulfone, polycarbonate, fluoropolymers, cellulosics, synthetic rubber, silk, silicone, and mixtures or blends thereof. Additional polymer substrates are also functionalized polymer substrates comprising the aforementioned polymers, which may further comprise or may be functionalized to comprise active groups with which peptoid oligomers may react, and which allow for immobilization of same. Examples of active groups include, but are not limited to: acrylic acid, acetal, hydroxyl, amines, epoxides, carboxylates, anhydrides, isocyanates, thioisocyanates, azides, aldehydes, halides, acyl halides, aryl halides and ketones at 1 to 50% by weight of the polymer. Various methods of protein or peptide immobilization are described in Protein Immobilization (Richard F. Taylor (ed.), Marcel Dekker, New York, 1991); similar methods may be used such as those familiar to practitioners skilled in the art of immobilization of peptoids.

Substrates suitable for the present invention also include ceramics, glass, metal, metal oxides, and composites comprised of ceramics, glass, metal or metal oxides plus polymers as described above. Suitable metals include steel, stainless steel, aluminum, copper, titanium, alloys thereof, and combinations thereof.

The articles of the present invention have antimicrobial peptoid oligomers of the invention bound to or incorporated into a substrate. The use of antimicrobial peptoid oligomers to confer antimicrobial properties to substrates provides many advantages due to the fact that the peptoid oligomers of the invention exhibit rapid biocidal activity, broad spectrum activity, and a reduced likelihood of resistance in target organisms compared to more traditional antimicrobials, such as antibiotics. Peptoid oligomers can be bound to a substrate either physicochemically or covalently. Physicochemical binding of peptoid oligomers to the substrate may occur by any one or combinations of the following forces: electrostatic, hydrogen bonding, and Van der Waals. Alternatively, peptoid oligomers may be bound to the substrate surface by a covalent bond. Additionally, antimicrobial peptoid oligomers of the present invention can be incorporated into the polymer by mixing with the polymer, for example by dissolving the peptoid oligomer and the polymer in a common solvent and casting or molding the peptoid oligomer: polymer mixture into an article.

In one embodiment, the antimicrobial peptoid oligomer is bound to the substrate by coating a substrate polymer with an aqueous or non-aqueous solution of the peptoid oligomer, wherein the peptoid oligomer is at concentration ranging from about 0.0001 to about 20 weight percent. The peptoid oligomer is contacted with the substrate polymer, and the peptoid oligomer and substrate polymer are optionally shaken at temperatures ranging from about −10° C. to about 150° C. for a period of time ranging from about 0.1 min to about 96 hrs. Preferably the peptoid oligomer and substrate polymer are shaken at a temperature of from about 25° C. to about 80° C. for a period of time ranging from about 1 min to about 24 hrs.

In another embodiment, the substrate polymer is primed to generate active groups that will bind to the antimicrobial peptoid oligomer. Surface modification of the polymer may be achieved by a variety of techniques well known in the art including: oxidation, reduction, hydrolysis, plasma, and irradiation. Substrate polymers containing acid or base hydrolyzable groups such as polyesters, polyamides, and polyurethanes may be treated with acid or base first. Subsequently, the hydrolyzed polymer is brought into contact with an aqueous or non-aqueous solution of from about 0.001 to about 20 weight percent of the antimicrobial peptoid oligomer. The peptoid oligomer and the polymer may be shaken at temperatures ranging from about −10° C. to about 150° C. for a period of time ranging from about 0.1 min to about 96 hrs. Preferably the peptoid oligomer and substrate polymer are shaken at a temperature of from about 25° C. to about 80° C. for a period of time ranging from about 10 min to about 24 hrs.

In another embodiment, a commercial substrate polymer containing 1-50% active groups is brought into contact with an aqueous or non-aqueous solution comprising from about 0.0001 to about 20 weight percent of the antimicrobial peptoid oligomer. These active groups may include azide and/or alkyne functions to permit formation of triazole crosslinks by cycloaddition reactions.

Methods for binding or incorporating peptides and/or peptoids to substrates are known to those of skill in the art who would, moreover, be aware of additional modifications to the above general guidelines that could be implemented, as required, to improve binding or incorporation of the peptoid oligomers of the invention to substrates. U.S. Pat. No. 7,307,061, for example, describes such methods in detail and is incorporated herein in its entirety.

After treatment with the antimicrobial peptoid oligomer, the article may be washed, preferably with deionized water. Optionally, the article may then be dried via methods known in the art. Such methods include ambient air drying, oven drying, and air forced drying. In one preferred embodiment, the article is dried at about 50° C. to about 120° C., more preferably at about 50° C. to about 100° C., for about 15 min to about 24 hrs.

Articles comprising the polymer substrate of the present invention may be in the form of or comprise an extrudate, film, membrane, laminate, knit fabric, woven fabric, nonwoven fabric, fiber, filament, yarn, pellet, coating, or foam. Articles may be prepared by any means known in the art, such as, but not limited to, methods of injection molding, extruding, blow molding, thermoforming, solution casting, film blowing, knitting, weaving, or spinning.

The preferred articles of the present invention provide multiple uses, since many articles benefit from a reduction in microbial growth and a wide variety of substrates are included in the present invention. The following are examples of articles wherein it is desirable to reduce microbial growth in or on the article in the end-use for which the particular article is commonly intended.

The articles of the invention include packaging for food, personal care (health and hygiene) items, and cosmetics. By "packaging" is meant either an entire package or a component of a package. Examples of packaging components include but are not limited to packaging film, liners, absorbent pads for meat packaging, tray/container assemblies, caps, adhesives, lids, and applicators. The package may be in any form appropriate for the particular application, such as a can, box, bottle, jar, bag, cosmetics package, or closed-ended tube. The packaging may be fashioned by any means known in the art, such as by extrusion, coextrusion, thermoforming, injection molding, lamination, or blow molding.

Some specific examples of packaging include, but are not limited to bottles, tips, applicators, and caps for prescription and non-prescription capsules and pills; solutions, creams, lotions, powders, shampoos, conditioners, deodorants, antiperspirants, and suspensions for eye, ear, nose, throat, vaginal, urinary tract, rectal, skin, and hair contact; lip product packaging, and caps.

Examples of applicators include those for lipstick, chapstick, and gloss; packages and applicators for eye cosmetics, such as mascara, eyeliner, shadow, dusting powder, bath powder, blusher, foundation and creams. These applicators are used to apply substances onto the various surfaces of the body and reduction of bacterial growth will be beneficial in such applications.

Other forms of packaging components included in the present invention include drink bottle necks, replaceable caps, non-replaceable caps, and dispensing systems; food and beverage delivery systems; baby bottle nipples and caps; and pacifiers. Where a liquid, solution or suspension is to be applied, the package may be fashioned for application in a form for dispensing discrete drops or for spraying of droplets. The invention will also find use in pharmaceutical applications fashioned as inhalers.

Examples of end-use applications, other than packaging, in the area of food handling and processing that benefit from antimicrobial functionality and wherein microbial growth is reduced in the particular end-use of the consumer are coatings for components of food handling and processing equipment, such as temporary or permanent food preparation surfaces; conveyer belt assemblies and their components; equipment for mixing, grinding, crushing, rolling, pelletizing, and extruding and components thereof; heat exchangers and their components; and machines for food cutting and slicing and components thereof. Where the surface of such equipment components is metal, the metal could be coated directly, or a coating of a polymer or functionalized polymer could first be applied to the metal surface. Alternatively, a film of such a polymer or functionalized polymer could be coated with an antimicrobial peptoid oligomer of the invention and then applied to the equipment surface. Additional articles of the invention include foods and seeds.

Articles of the present invention can also be used in or as items of apparel, such as a swimsuit, undergarment, shoe component (for example, a woven or nonwoven shoe liner or insert), protective sports pad, or child's garment. Articles of the invention also include protective medical garments or barrier materials, such as gowns, masks, gloves, slippers, booties, head coverings or drapes.

Articles of the present invention can also be used in or as medical materials, devices, or implants, such as bandages, adhesives, gauze strips, gauze pads, syringe holders, catheters such as peripheral IV catheters and central venus catheters comprised of either polyurethane or silicon, sutures, urinary catheter ostomy ports, orthopedic fixtures, orthopedic pins, pacemaker leads, defibrillator leads, ear canal shunts, vascular stents, cosmetic implants, ENT implants, staples, implantable pumps, hernia patches, plates, screws, blood bags, external blood pumps, fluid administration systems, heart-lung machines, dialysis equipment, artificial skin, artificial hearts, ventricular assist devices, hearing aids, vascular grafts, pacemaker components, hip implants, knee implants, and dental implants.

In the hygiene area, articles of the present invention include personal hygiene garments such as diapers, incontinence pads, sanitary napkins, sports pads, tampons and their applicators; and health care materials such as antimicrobial wipes, baby wipes, personal cleansing wipes, cosmetic wipes, diapers, medicated wipes or pads (for example, medicated wipes or pads that contain an antibiotic, a medication to treat acne, a medication to treat hemorrhoids, an anti-itch medication, an anti-inflammatory medication, or an antiseptic).

Articles of the present invention also include items intended for oral contact, such as a baby bottle nipple, pacifier, orthodontic appliance or elastic bands for same, denture material, cup, drinking glass, toothbrush, or teething toy. Additional child-oriented articles that benefit from the present invention include baby bottles, baby books, plastic scissors, toys, diaper pails, and a container to hold cleansing wipes.

Household articles of the present invention include telephones and cellular phones; fiberfill, bedding, bed linens, window treatments, carpet, flooring components, foam padding such as mat and rug backings, upholstery components (including foam padding), nonwoven dryer sheets, laundry softener containing sheets, automotive wipes, household cleaning wipes, counter wipes, shower curtains, shower curtain liners, towels, washcloths, dust cloths, mops, table cloths, walls, and counter surfaces.

The current invention is also useful in reducing or preventing biofilm growth on the surface of separation membranes (for example, pervaporation, dialysis, reverse osmosis, ultrafiltration, and microfiltration membranes) comprised of polymer substrates of the invention.

As used herein and referred to in the art, a biofilm is an aggregate of microbes with a distinct architecture. A biofilm is essentially a collective in which microbial cells, each only a micrometer or two long, form towers that can be hundreds of micrometers high. The channels between the towers act as fluid-filled conduits that circulate nutrients, oxygen, waste products, etc., as required to maintain a viable biofilm community. The biofilm or microbial (bacterial, fungal, or algal) community is typically enveloped by extracellular biopolymers produced by the microbial cells and adheres to the interface between a liquid and surface. The encapsulated property of biofilms renders the microbial organisms therein highly resistant to standard anti-microbial therapeutics. Bacteria growing in a biofilm, for example, are highly resistant to antibiotics, and in some cases are up to 1,000 times more resistant than the same bacteria growing without a biofilm superstructure. Standard antibiotic therapy can be useless wherein a biofilm contaminated implant is detected and the only recourse under such circumstances may be to remove the contaminated implant. Fungal biofilms also frequently contaminate medical devices. They can cause chronic vaginal infections and lead to life-threatening systemic infections in immunocompromised individuals. Biofilms are, furthermore, involved in numerous diseases. Cystic fibrosis patients, for example, suffer from *Pseudomonas* infections that often result in antibiotic resistant biofilms.

The antimicrobial peptoid oligomers of the invention are well suited to applications directed to the prevention of biofilm formation or eradication of a pre-existing biofilm because they act quickly, exhibit good permeability, and are resistant to proteolysis. As indicated herein above, these advantageous properties also apply to other uses of the antimicrobial peptoid oligomers of the invention.

In order to impart antimicrobial functionality to the products listed, the product can be treated with an antimicrobial peptoid oligomer of the invention before it is manufactured, or after, or at any time during manufacture of the product. For example, in making an antimicrobial shower curtain, an antimicrobial peptoid oligomer of the invention may be bound to or incorporated into the polymer substrate, followed by fashioning a shower curtain from the treated material. Alternatively, treatment of the polymer substrate with an antimicrobial peptoid oligomer of the invention may be performed after the substrate is made into a shower curtain.

Antimicrobial substrates or articles prepared by methods of the invention exhibit antimicrobial functionality, wherein microbes are killed, or microbial growth is reduced or prevented. Antimicrobial activity of the antimcrobial substrate or article can be determined by using any of a number of methods well known in the art, such as the Shake Flask Test described in U.S. Pat. No. 7,307,061 and United States Patent Application No. 2008/0081789, the entire contents of which are incorporated herein in their entireties. Additional methods for determining antimicrobial activity are discussed in Tenover et al. (eds.), Manual of Clinical Microbiology, 7.sup.th Edition, Section VIII, 1999, American Society for Microbiology, Washington, D.C.

General Synthetic Procedures

The complexes of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative peptoid oligomers that have been listed hereinabove. The peptoid oligomers of the invention may be prepared from known or commercially available starting materials and reagents by one skilled in the art of organic synthesis.

Solvents and reagents purchased from commercial sources were used without further purification. Abbreviations for reagents are as follows: 9-fluorenylmethoxycarbonyl (Fmoc); tert-butoxycarbonyl (Boc); benzotriazole-1-yl-oxy-tris-pyrrolidino-phosphonium hexafluorophosphate (PyBOP); Bromo-tris-pyrrolidino phosphoniumhexafluorophosphate (PyBrOP); trifluoroacetic acid (TFA); hexafluoroisopropyl alcohol (HFIP); methylene chloride (DCM); N,N'-dimethylformamide (DMF); N,N'-diisopropylcarbodiimide (DIC); diisopropylethylamine (DIEA); acetonitrile (ACN); N-methylmorpholine (NMM); O-Benzotriazole-N, N,N',N'-tetramethyl-uronium-hexafluoro-phosphate (HBTU).

Representative Synthetic Method Preparation of Peptoid Oligomers of the Invention General protocols for the synthesis of both linear and benzyl substituted cyclic peptoid oligomers are shown in Scheme 1. These sequence-specific N-substituted glycine oligomers can be efficiently synthesized via "submonomer chemistry" methods to incorporate a large number of diverse side chain chemical functionalities (Figliozzi et al, Synthesis of N-substituted glycine peptoid libraries. In *Methods Enzymol.*, Academic Press: 1996; Vol. 267, pp 437-447; Bartlett et al., *Proc. Natl. Acad. Sci. U.S.A.* 1992, 89, 9367-9371). This approach iterates sequential steps of bromoacylation and nucleophilic displacement to construct each monomer unit. The side chain moieties are introduced upon the displacement of bromide by diverse primary amine submonomer reagents. The Table S2 lists monomers used in the synthesis of the peptoid oligomers of the invention.

TABLE S2

Monomers used and corresponding submonomer precursors.

| Monomer Name | Submonomer | Chemical Structure | Source |
|---|---|---|---|
| Nap<br>N-(3-aminopropyl)glycine | N-Boc-1,3-diaminopropane | 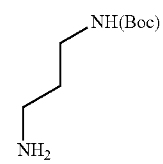 | Synthesized[S1] |
| Ndp<br>N-(2,2-diphenylethyl)glycine | 2,2-diphenylethylamine | 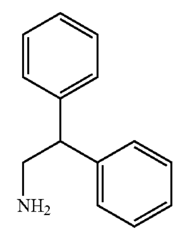 [SMILES: NCC(c1ccccc1)c1ccccc1] | Acros or<br>Sigma-Aldrich |
| Ndpp<br>N-(3,3-diphenylpropyl)glycine | 3,3-diphenylpropylamine | 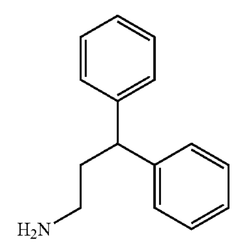 [SMILES: NCCC(c1ccccc1)c1ccccc1] | Sigma-Aldrich |
| Ndpm<br>N-(1,1-diphenylmethyl)glycine | 1,1-diphenylmethylamine | 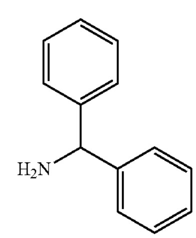 [SMILES: NC(c1ccccc1)c1ccccc1] | Sigma-Aldrich |
| Npp<br>N-(benzylphenyl)glycine | 4-phenylbenzylamine | 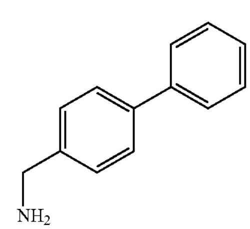 [SMILES: NCc1ccc(-c2ccccc2)cc1] | Sigma-Aldrich |

TABLE S2-continued

Monomers used and corresponding submonomer precursors.

| Monomer Name | Submonomer | Chemical Structure | Source |
| --- | --- | --- | --- |
| N2flene<br>N-(2-fluorene)glycine | 2-Aminofluorene | 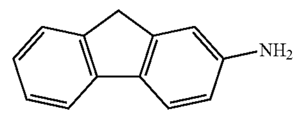 [SMILES: Nc1ccc2c(c1)Cc1ccccc1-2] | Alfa Aesar |
| N9flene<br>N-(9-fluorene)glycine | 9-Aminofluorene hydrochloride | 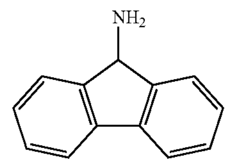 [SMILES: NC1c2ccccc2-c2ccccc21] | Alfa Aesar |
| Nsne<br>N-(S-naphthylethyl)glycine | S-napthylethylamine | 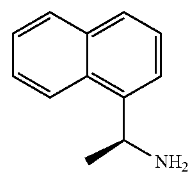 | Sigma-Aldrich |
| Netrp<br>N-(ethyltryptophan)glycine | Tryptamine | 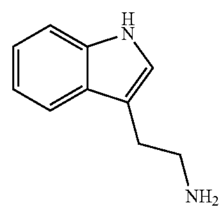 [SMILES: NCCc1c[nH]c2ccccc12] | Sigma-Aldrich |
| Npero<br>N-(piperonyl)glycine | Piperonylamine | 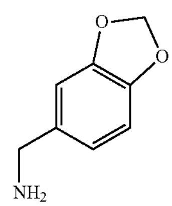 [SMILES: NCc1ccc2c(c1)OCO2] | Sigma-Aldrich |
| Nar<br>N-(aryl)glycine | Aniline | 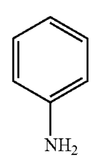 | Sigma-Aldrich |
| Npfa<br>N-(4-fluoroaryl)glycine | 4-fluoroaniline | 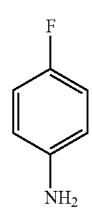 | Oakwood Products |
| Npma<br>N-(4-methylaryl)glycine | p-toluidine | 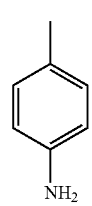 | Sigma-Aldrich |

TABLE S2-continued

Monomers used and corresponding submonomer precursors.

| Monomer Name | Submonomer | Chemical Structure | Source |
|---|---|---|---|
| Nspe<br>N-(S-phenylethyl)glycine | S-phenylethylamine | 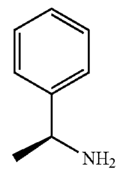 | TCI America |
| Nrpe<br>N-(R-phenylethyl)glycine | R-phenylethylamine | 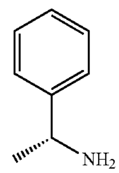 | TCI America |
| Nspfpe<br>N-(S-4-fluorophenylethyl)glycine | S-(4-fluoro)<br>phenylethylamine | 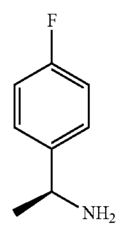 | Acros |
| Npmpm<br>N-(p-methylphenylmethyl)glycine | 4-methylbenzylamine | 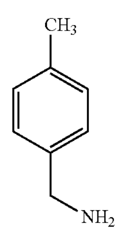 | Sigma-Aldrich |
| Nptfmpm<br>N-(p-trifluoromethylphenylmethyl)glycine | 4-trifluoromethylbenzyl-<br>amine | 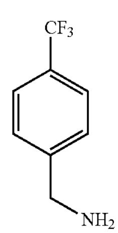 | Alfa Aesar |
| Ndmb<br>N-(3,5-dimethylbenzyl)glycine | 3,5-dimethylbenzylamine | 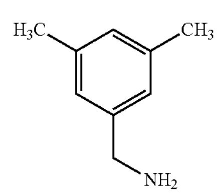 | Oakwood<br>Products |

TABLE S2-continued

Monomers used and corresponding submonomer precursors.

| Monomer Name | Submonomer | Chemical Structure | Source |
|---|---|---|---|
| Nbtfmb<br>N-(3,5-bis-trifluoromethylbenzyl)glycine | 3,5-bis-(trifluoromethyl)<br>benzylamine | F$_3$C―⬡―CF$_3$ with ―NH$_2$ | Oakwood<br>Products |

Scheme1: Synthesis (A) N-acetylated linear peptoid oligomers and (B) cyclic peptoid oligomers.

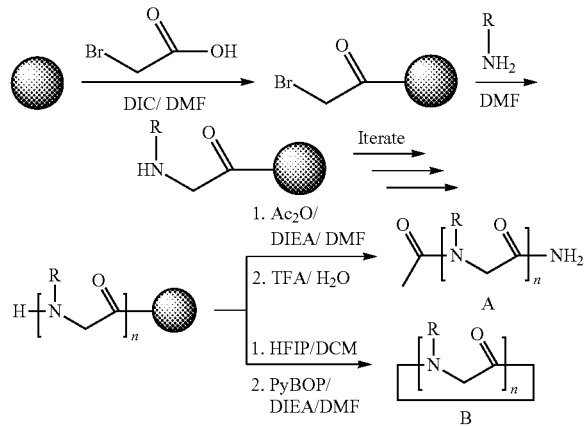

wherein R = R$^1$, and R$^1$ is as described herein.
DIC: diisopropylcarbodiimide; DMF; N, N-dimethylformamide;
DIEA: diisopropylethylamine; TFA: trifluoroacetic acid;
HFIP: 1,1,1,3,3,3-haxefluoroisopropanol.
*Rink Amide resin was used to generate N-acetylated linear oligomers and 2-chlorotrityl chloride resin was used to generate benzyl substituted cyclic peptoid oligomers.
** n = 6,8, 10

N-acetylated linear oligomers were synthesized on Rink® Amide resin to afford peptoid C-terminal amides. The N-terminus was acetylated with acetic anhydride prior to TFA cleavage. Macrocyclic peptoid oligomers were generated from linear precursors containing free N-terminal amino groups and C-terminal carboxylic acid groups in PyBOP/DIEA/DMF. The linear precursors were synthesized on 2-chlorotrityl resin and cleaved with 20% HFIP/DCM.

Figure 10:
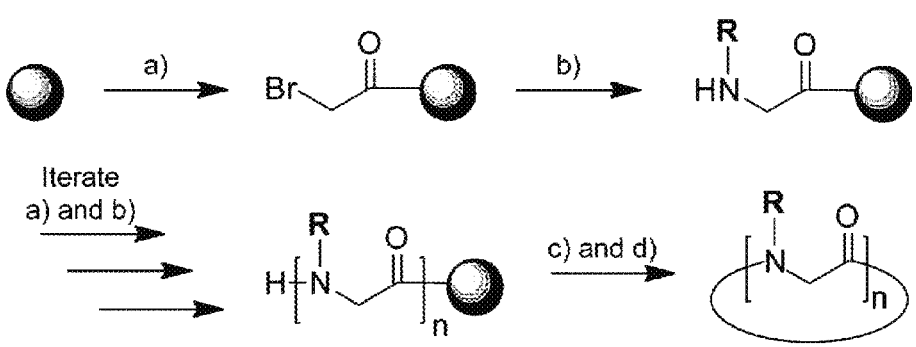
FIG. 10 shows a representative synthetic scheme for preparation of cyclic peptoids. Submonomer synthesis of cyclic peptoid oligomers. The linear precursors were synthesized on solid-phase using 2-chlorotrityl chloride resin. Elongation of the linear peptoid entails iterative a) bromoacetylation (with bromoacetic acid) and b) nucleophilic displacement (with a primary amine, R—$NH_2$) steps. Chemical diversity can easily be incorporated into the peptoid chain by varying the R groups on the primary amine. Following c) cleavage of the peptoid oligomer from the resin (20% HFIP/DCM), d) head-to-tail macrocyclization can then be employed in solution with an activating agent (PyBOP/DIEA/DMF). Conversion yields ≥95% are routinely observed in the synthesis of cyclic peptoid oligomers.

Amphiphilic peptoid macrocycles were synthesized with aminopropyl groups as cationic residues and included a variety of hydrophobic residues (FIG. 11; Table S2). The hydrophobic residues included in the library featured aromatic side chain groups including phenyl, diphenyl, naphthyl, fluorene, and fluoroaryl groups. The cationic and hydrophobic residues were alternated within the oligomer sequence to produce cyclic peptoid hexamers (scaffold A in FIG. 11) that would allow cationic and hydrophobic surface areas to segregate on opposite faces of the planar macrocycle (Kirshenbaum et al, J. Am. Chem. Soc. 2007, 129, 3218-3225). Head-to-tail macrocyclization of peptoid oligomers was implemented in solution (FIG. 10), following the step-wise assembly and cleavage of the corresponding linear precursors on solid-support. Due to the odd number of residues in cyclic pentamers, these were synthesized to include either two (scaffold B) or three (scaffold C) hydrophobic residues (FIG. 11). Following RP-HPLC purification (to ≥95% purity) and ESI-MS characterization, a total of 25 peptoid compounds (C101 to C125) were prepared, including 18 cyclohexamers and 7 cyclopentamers (Table S2 and S3, FIG. 13).

Synthesis and Purification of Cyclic Peptoid Oligomers

Previously reported solid phase peptoid synthesis protocols were used with adjustments in reaction time and washing conditions. Peptoid synthesis was performed using an automated synthesizer (Charybdis Technologies Inc., San Diego, Calif.) at room temperature. Peptoid oligomers were synthesized on 2-chlorotrityl chloride resin (NovaBiochem; 100-200 mesh; 1.1 mmol/g).

Typically, for the generation of benzyl substituted cyclic peptoid oligomers, 200 mg of 2-chlorotrityl chloride resin was washed twice in 2 mL of DCM, followed by swelling in 2 mL of DCM. The first monomer was added manually by reacting 37 mg of bromoacetic acid (0.27 mmol; Sigma-Aldrich) and 189 µL of DIEA (1.08 mmol; Chem Impex International) in 2 mL of DCM on a shaker platform for 30 minutes at room temperature, followed by extensive washes with DCM (five times with 2 mL) and DMF (five times with 2 mL). Bromoacylated resin was incubated with 2 mL of 1 M. amine submonomer in DMF on a shaker platform for 30 minutes at room temperature, followed by extensive washes with DMF (five times with 2 mL). After initial manual loading of bromoacetic acid, the first submonomer displacement step and all subsequent bromoacetylation and amine displacement steps were performed by a robotic synthesizer until the desired oligomer length was obtained. The automated bromoacetylation step was performed by adding 1660 µL of 1.2 M bromoacetic acid in DMF and 400 µL of DIC (Chem Impex International). The mixture was agitated for 20 min, drained, and washed with DMF (three times with 2 mL). Next, 2 mL of a 1 M. solution of submonomer (2 mmol) in DMF was added to introduce the side chain by nucleophilic displacement of bromide. The mixture was agitated for 20 min, drained, washed with DMF (three times with 2 mL) and washed with DCM (three times with 2 mL). The peptoid-resin was cleaved in 2 mL of 20% HFIP (Alfa Aesar) in DCM (v/v) at room temperature. The cleavage was conducted in a glass tube with constant agitation for 30 minutes. HFIP/DCM was evaporated under a stream of nitrogen gas. The final product was dissolved in 5 mL of 50% ACN in HPLC grade H$_2$O and filtered with a 0.5 µm stainless steel fritted syringe tip filter (Upchurch Scientific).

Peptoid oligomers were analyzed on a $C_{18}$ reversed-phase analytical RP-HPLC column at room temperature (Peeke Scientific, 5 µm, 120 Å, 2.0×50 mm) using a Beckman Coulter System Gold instrument. A linear gradient of 5-95% acetonitrile/water (0.1% TFA, Acros Organics) over 20 min was used with a flow rate of 0.7 mL/min. In order to remove any traces of HFIP in the sample solution, linear precursors dissolved in 50% ACN/$H_2O$ were freeze-dried overnight.

Cyclization reactions were conducted, with crude linear precursors, in dry, deoxygenated DMF. The purified linear oligomer (12 µmoles) was suspended in 5.25 mL of DMF in a 15 mL conical tube. PyBOP (NovaBiochem) solution (375 µL, 96 mM, freshly prepared in DMF) and 375 µL of DIEA solution (192 mM, freshly prepared in DMF) were added to the peptoid. The reaction vessel was flushed with nitrogen and sealed to exclude air. The reaction proceeded for 5 minutes at room temperature and 10 µL of reaction mixture was diluted with 140 µL of 50% ACN in $H_2O$ to quench the reaction. The diluted sample was analyzed by HPLC. Preparative HPLC was performed on a Delta-Pak $C_{18}$ (Waters, 15 µm, 100 Å, 25×100 mm) with a linear gradient of 5-95% acetonitrile/water (0.1% TFA) over 60 min with a flow rate of 5 mL/min. LC-MS was performed on an Agilent 1100 Series LC/MSD Trap XCT (Agilent Technologies). The purified HPLC fraction was freeze-dried. Boc protecting groups were removed with 5 mL of 95% TFA/$H_2O$ over 30 minutes at room temperature. A stream of nitrogen gas was used to reduce the volume of TFA solution to 10% of its original volume. The concentrated sample was dissolved in 15 mL of 50% ACN/$H_2O$ and freeze-dried.

Alternate Synthesis of Benzyl Substituted Cyclic Peptoid Oligomers

Synthesis of Cyclic Peptoid Library.

The peptoids in this library were synthesized based on the observations that (i) macrocyclization enhances antimicrobial activity, (ii) hydrophobicity is critical for potency, and (iii) varying the composition of cationic residues types does not significantly alter activity. With these parameters in mind, a library of cyclic peptoids ranging from five to six residues were synthesized using previously published protocols (Figliozzi et al, *Method Enzymol* 1996, 267:437-447; Shin et al, Cyclic peptoids. *J Am Chem Soc* 2010, 129:3218-3225; Shin et al, Cyclic peptoids. *J Am Chem Soc* 2010, 129:3218-3225) The peptoid macrocycles were synthesized with aminopropyl groups as cationic residues and varying hydrophobic residues. The macrocycle sizes were chosen to minimize molecular weights without significantly decreasing cyclization yields.

The hydrophobic residues incorporated in the library included aromatic groups ranging from phenyl, diphenyl, naphthyl, and fluorene groups. Fluorinated hydrophobic residues were also included in the library to compare the effects of substituting fluorine for hydrogen atoms on bioactivity. Hydrophobic groups with chiral side chains were introduced, as well as N-aryl side chains, and side chains which are capable of hydrogen bonding. The cationic aminopropyl and varying hydrophobic residues were alternated in the sequences of cyclic hexamers. (formula IVa). Due to the odd number of residues in cyclic pentamers, they were synthesized with either two (formula IVb) or three (formula IVc) hydrophobic residues. Cyclic pentamers with IVb are expected to be less hydrophobic than corresponding sequences with IVc. Following step-wise assembly on solid-support and macrocyclization in solution, the cyclic peptides were purified by RP-HPLC (to >95% purity) and their identities were confirmed by ESI-MS.

2-Chlorotrityl chloride (100 mg) was swollen with DCM (5 min., RT) and reacted with bromoacetic acid (90.3 mg) and DIEA (107 µL) in 2 mL DCM (≥40 min.). Following washes with DCM (3×1 min.) and DMF (3×1 min.), the desired first amine submonomer was added (1.0 mL of a 1.0 M. solution in DMF) and allowed to react for 20 min. The resins were then washed with DMF (3×1 min.), and bromoacylated with bromoacetic acid (1.0 mL of a 1.0 M. solution in DMF) and DIC (300 µL, neat) for 20 minutes. Following washings (3×1 min.) with DMF, the amine displacement and bromoacetylation steps were repeated until the final submonomer has been added and the desired sequence has been obtained. The resins were then washed extensively with DMF (3×1 min.) and DCM (3×1 min.), and cleaved off the resin with (3 mL) 20% HFIP/DCM (30 min.). The cleavage cocktail was evaporated with a $N_2$ stream, re-dissolved with 50% ACN/$H_2O$, frozen, and lyophilized. Cyclization reactions were conducted with the crude linear precursors in dry deoxygenated DMF. Typically, the linear oligomer (12 µmol) was suspended in DMF (5.25 mL) with freshly prepared solutions of PyBOP (375 µL of a 96 mM solution in DMF) and DIEA (375 µL of a 192 mM solution in DMF) (FIG. 1). The reaction vessel was sealed with parafilm to exclude air and allowed to react for ~30 min. at room temperature. The solution was then evaporated under pressure and heat (temperatures≤60° C.), and the resulting product re-dissolved in 50% ACN/$H_2O$, frozen, and lyophilized.

The crude products were re-dissolved in 50% ACN/$H_2O$, and purified by RP-HPLC ($C_{18}$ semi-prep column, Waters, 15 µm, 100 Å, 25×100 mm) using a Beckman Coulter System Gold Instrument operated with 32Karat. A typical method used for the purification was 30-100% ACN/$H_2O$ in 40 min. at a 2.5 mL/min flow rate and 214 nm or 230 nm wavelength. Relevant fractions were collected, frozen, and lyophilized. The Boc groups were deprotected by subjecting the dried product with 50% TFA/DCM (30 min., RT). The cocktail was evaporated with $N_2$, and the product was re-dissolved with 50% ACN/$H_2O$, frozen, and lyophilized. Characterization of purified (to >95% by RP-HPLC) products was performed on a RP-HPLC $C_{18}$ analytical column (Peeke Scientific, 5 µm, 120 Å, 2.0×50 mm) and Agilent 100 Series LC-MSD Trap XCT (Agilent Technologies).

Another Synthesis of Benzyl Substituted Cyclic Peptoid Oligomers

Cyclic Peptoid Library.

Cyclic peptides were manually synthesized using standard solid-phase submonomer synthesis protocols as given herein. The 2-chlorotrityl resin (100 mg) was added to a fritted syringe and swelled in DCM (3 mL) for 10 min followed by two washes with DCM (2 mL). The first monomer was prepared in situ by reacting bromoacetic acid (0.65 mmol) and DIEA (107 µL) and was added in DCM (1 mL) to the above mixture on a shaker platform for 30 min at room temperature, followed by five washes with DCM (2 mL) and five washes with DMF (2 mL). The bromoacetylated resin was incubated with the amine submonomer (1 mL of 1 M. solution in DMF) on a shaker platform for 30 min at room temperature followed by 5 washes with DMF (2 mL) to add the first side chain. Subsequent bromoacetylation steps and amine displacement steps were conducted until the desired oligomer length was obtained. Each bromoacetylation step was performed by adding 1.2 M. bromoacetic acid (1 mL in DMF) and DIC (200 μL). The mixture was agitated on a shaker platform for 30 min at room temperature followed by five washes with DMF (2 mL). Each amine displacement step was performed by reacting 1 M. amine submonomer (1 mL) on a shaker platform for 30 min at room temperature followed by five washes with DMF (2 mL). After addition of the final submonomer, the peptoid-resin was washed five times with DMF (2 mL) and five times with DCM (2 mL). The peptoid was cleaved from resin with 20% HFIP/DCM (3 mL) with constant agitation for 30 min at room temperature. HFIP/DCM was evaporated under a stream of nitrogen gas. The final product was dissolved in 50% ACN/H$_2$O (6 mL), frozen, and lyophilized overnight.

Cyclization reactions were performed in dry, deoxygenated DMF. The purified linear oligomer (12 μmol) was dissolved in DMF (5.25 mL) along with DIEA (12.5 μL) and PyBOP (18.7 mg). The reaction vessel was flushed with nitrogen gas and sealed to exclude air. The reaction was shaken for 30 min at room temperature. The solution was evaporated under reduced pressure and elevated temperature (<65° C.), and the resulting oil was dissolved in 50% ACN/H$_2$O (6 mL), frozen, and lyophilized overnight.

Peptoid oligomers were analyzed by C$_{18}$ reversed-phase analytical RP-HPLC (C$_{18}$ Peeke Scientific column, 5 μm, 120 Å, 2.0×50 mm) using a Beckman Coulter System Gold Instrument. A linear gradient of 5 to 95% ACN/H$_2$O (0.1% TFA) in 10 min with a 0.7 mL/min flow rate and 214 nm wavelength was used for each analysis. Crude oligomers were then redissolved in 50% ACN/H$_2$O and purified by preparative RP-HPLC (C$_{18}$ Waters column, 15 μm, 100 Å, 25×100 mm) with a linear gradient of 5 to 95% ACN/H$_2$O (0.1% TFA) in 50 min with a 2.5 mL/min flow rate and 230 nm wavelength. The desired fractions were collected, frozen, and lyophilized. Deprotection of boc groups was accomplished by dissolving the lyophilized powder in 50% TFA/DCM (2 mL) in a tightly sealed vial and stirring for 30 min at room temperature. The mixture was evaporated under a stream of nitrogen gas, and the product was dissolved in 50% ACN/H$_2$O, frozen, and lyophilized. Oligomers were characterized by analytical RP-HPLC as described above (>95% purity) and by Agilent 100 Series LC-MSD Trap XCT.

Synthesis and Purification of Gramicidin S

Peptide gramicidin S sequence was synthesized using standard Fmoc solid-phase peptide synthesis protocols. 200 mg of 2-chlorotrityl chloride resin (NovaBiochem; 100-200 mesh; 1.1 mmol/g) was washed twice in 2 mL of DCM, followed by swelling in 2 mL of DCM. The first amino acid was added manually by reacting 0.27 mmol of Fmoc-Phe (NovaBiochem) and 142 μL of DIEA in 2 mL of DCM on a shaker platform for 30 minutes at room temperature, followed by extensive washes with DCM (five times with 2 mL) and DMF (five times with 2 mL). Resin loaded with Fmoc-Phe was incubated twice with 2 mL of 20% piperidine/DMF (v/v) on a shaker platform for 15 minutes at room temperature, followed by extensive washes with DMF (five times with 2 mL). After manual loading of Phe, all subsequent amino acid addition and Fmoc deprotection steps were performed on a robotic synthesizer (Charybdis Technologies Inc., San Diego, Calif.) until the desired peptide length was obtained. Fmoc-Phe-OH, Fmoc-Leu-OH, Fmoc-Orn(Boc)-OH, Fmoc-Val-OH, and Fmoc-Pro-OH were purchased from NovaBiochem (San Diego, Calif.). The automated amino acid addition step was performed by adding 1 mL of 0.5 M. Fmoc-amino acid in DMF, 1 mL of 0.5 M. HBTU (NovaBiochem) in DMF and 1 mL of 1.5 M. NMM (Alfa Aesar) in DMF. The mixture was agitated for 30 min, drained, and washed with DMF (three times with 2 mL). Next, the resin was incubated twice with 2 mL of a 20% piperidine/DMF (v/v) for 15 minutes. The reaction was drained and washed with DMF (three times with 2 mL) and washed with DCM (three times with 2 mL). The peptide-resin was cleaved in 2 mL of 20% HFIP in DCM (v/v) at room temperature. The cleavage was conducted in a glass tube with constant agitation for 30 minutes. HFIP/DCM was evaporated under a stream of nitrogen gas. The final product was dissolved in 5 mL of 70% ACN in HPLC grade H$_2$O. Peptide oligomers were analyzed by RP-HPLC and ESI mass spectrometry as described above. Cyclization of gramicidin S sequence was performed as described above.

FIG. 1 shows a representative cyclization reaction monitored by RP-HPLC. The Boc protecting groups used on amino groups were removed after the cyclization step in 95% TFA/H$_2$O.

Table 1 shows LC-MS data of representative peptoid oligomers, following the removal of Boc protecting groups.

TABLE 1
ESI mass spectrometric data of representative peptoid oligomers
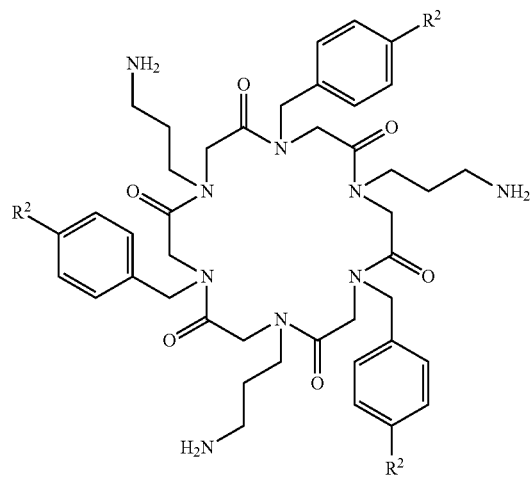
Va
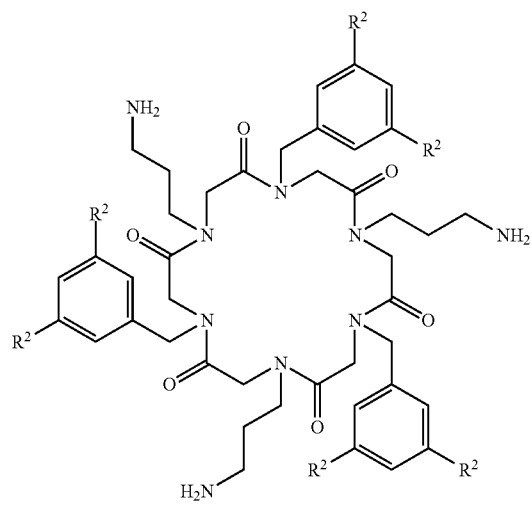
VIa
| # | Compounds | Chemical Structure | Calculated Mass[a] | Observed Mass |
|---|---|---|---|---|
| 17 | C(Gramicidin S) | 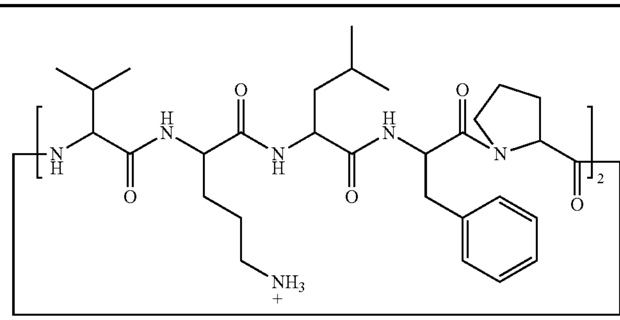 | 1140.71 | 1141.7 |

TABLE 1-continued
ESI mass spectrometric data of representative peptoid oligomers
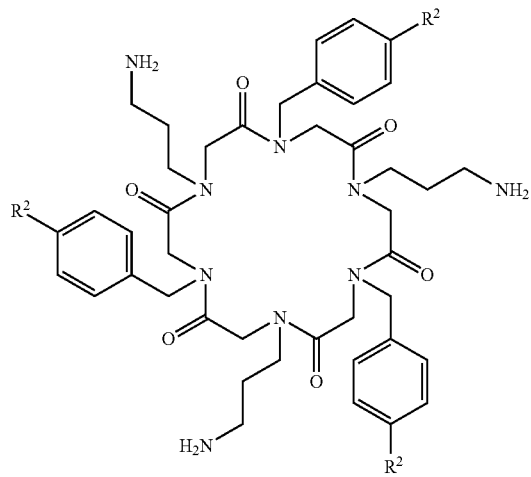
Va
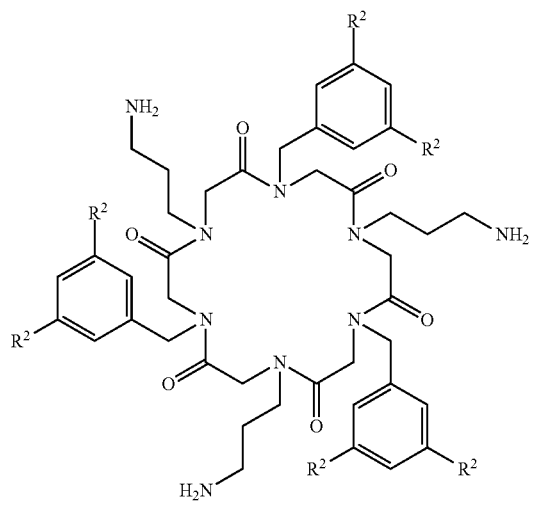
VIa
| # | Compounds | Chemical Structure | Calculated Mass[a] | Observed Mass |
|---|---|---|---|---|
| 18 | C(NgbNpm)₃ | 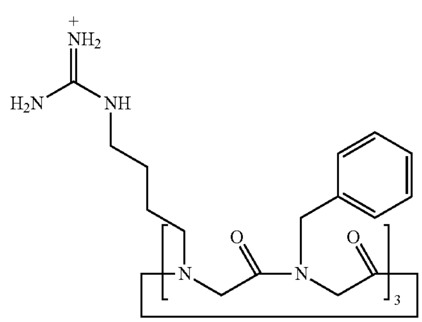 | 951.56 | 952.3 |

TABLE 1-continued
ESI mass spectrometric data of representative peptoid oligomers
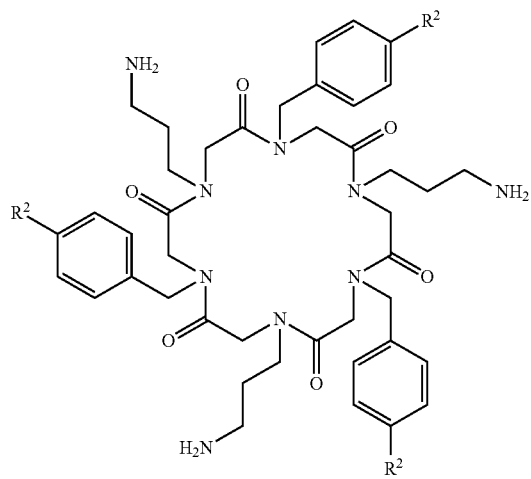
Va
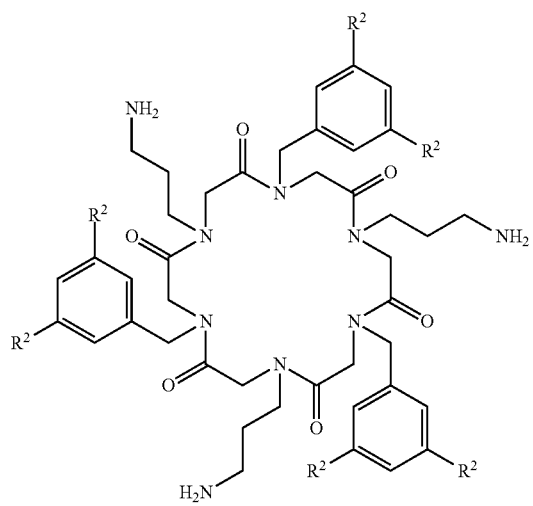
VIa
| # | Compounds | Chemical Structure | Calculated Mass[a] | Observed Mass |
|---|---|---|---|---|
| 19 | C(NahNpm)$_3$ | 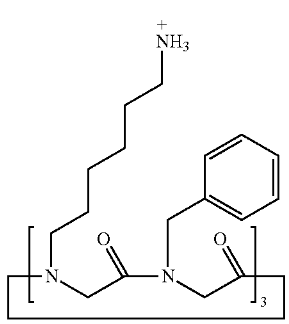 | 909.58 | 910.3 |
| 20 (C3) | C(NapNdp)$_3$ | 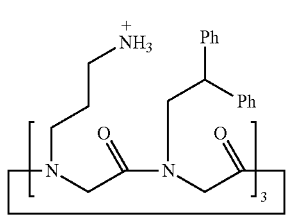 | 1053.58 | 1054.6 |

TABLE 1-continued
ESI mass spectrometric data of representative peptoid oligomers
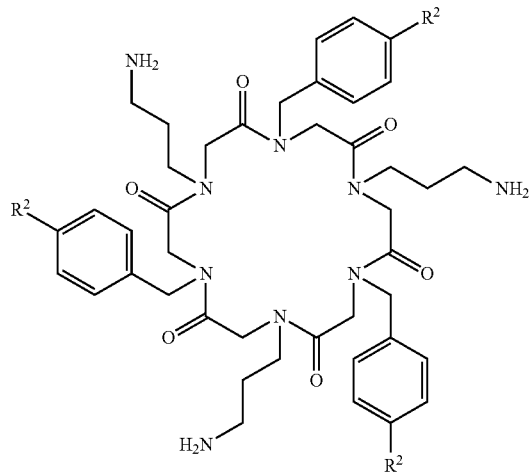
Va
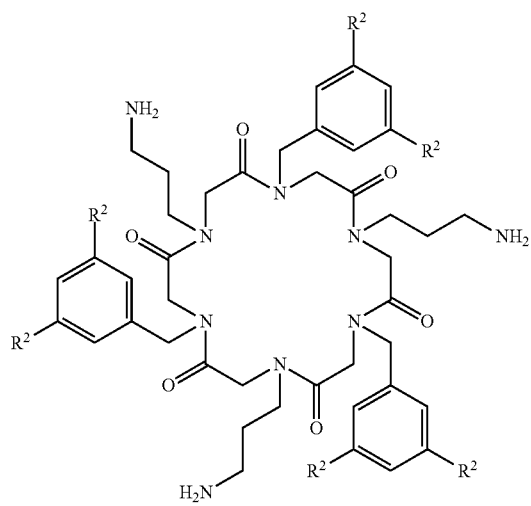
VIa
| # | Compounds | Chemical Structure | Calculated Mass[a] | Observed Mass |
|---|---|---|---|---|
| 21 | C(NapNnm)$_3$ | 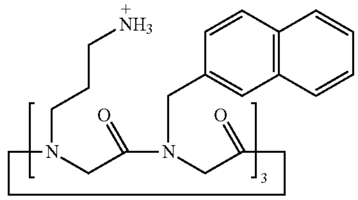 | 933.49 | 934.2 |
| 23 | C(NapNpm)$_3$ | 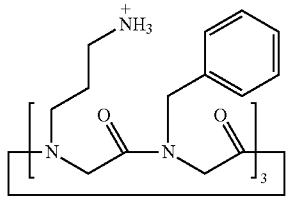 | 783.44 | 784.2 |

TABLE 1-continued
ESI mass spectrometric data of representative peptoid oligomers
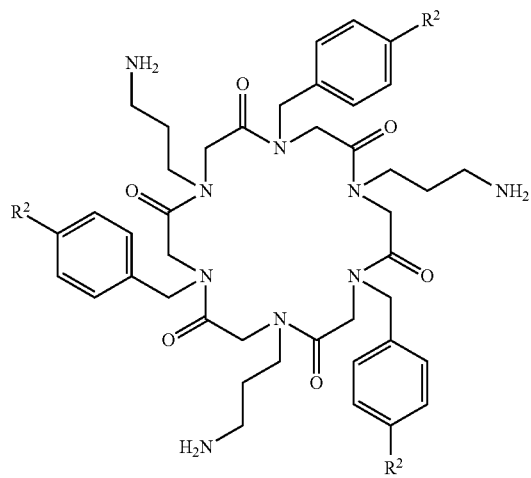
Va
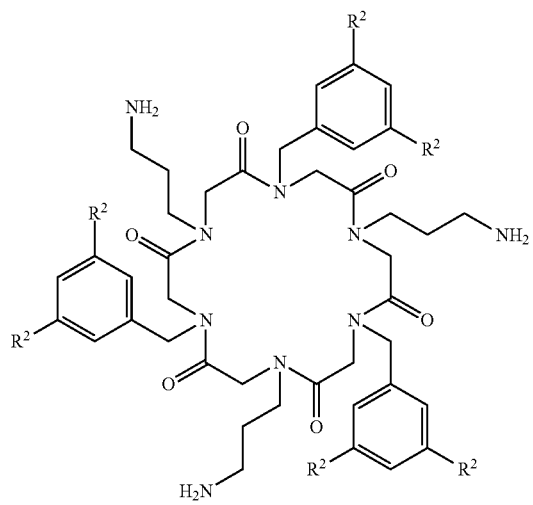
VIa
| # | Compounds | Chemical Structure | Calculated Mass[a] | Observed Mass |
|---|---|---|---|---|
| 24 | C(NapNpm)$_4$ | 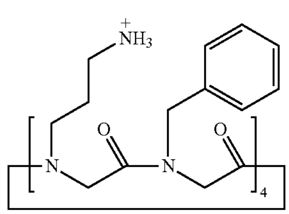 | 1044.59 | 1067.2 (M + Na) |
| 25 | C(NapNpm)$_5$ | 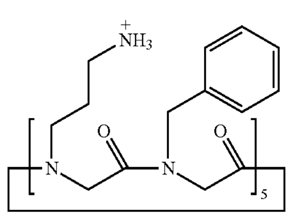 | 1305.74 | 1328.2 (M + Na) |

TABLE 1-continued
ESI mass spectrometric data of representative peptoid oligomers
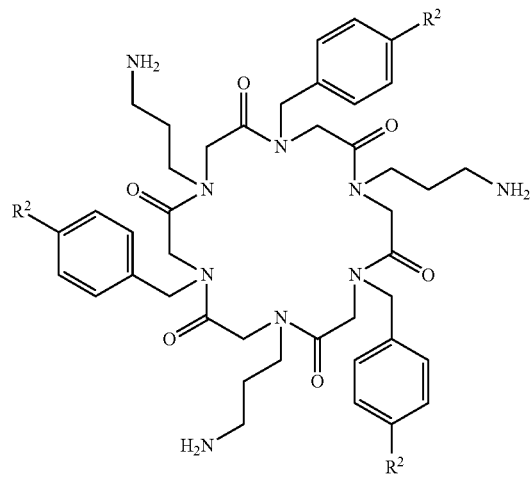
Va
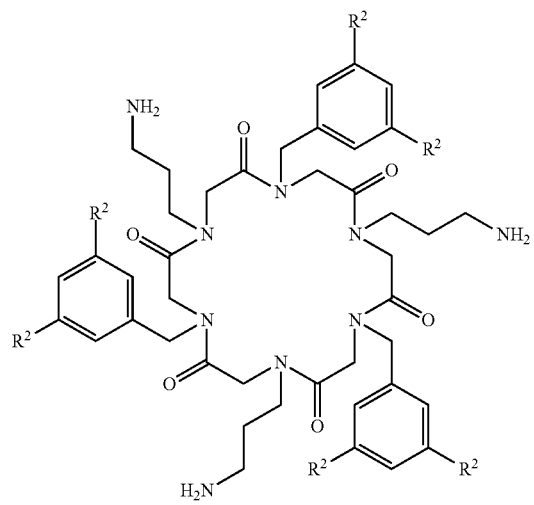
VIa
| # | Compounds | Chemical Structure | Calculated Mass[a] | Observed Mass |
|---|---|---|---|---|
| 26 | C(NpmNap)$_2$Npm$_2$ | 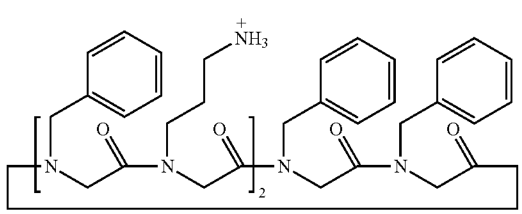 | 816.43 | 817.4 |
| 30 | C(NabNpm)$_3$ | 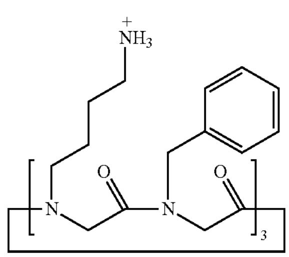 | 825.49 | 826.6 |

Figure 13:
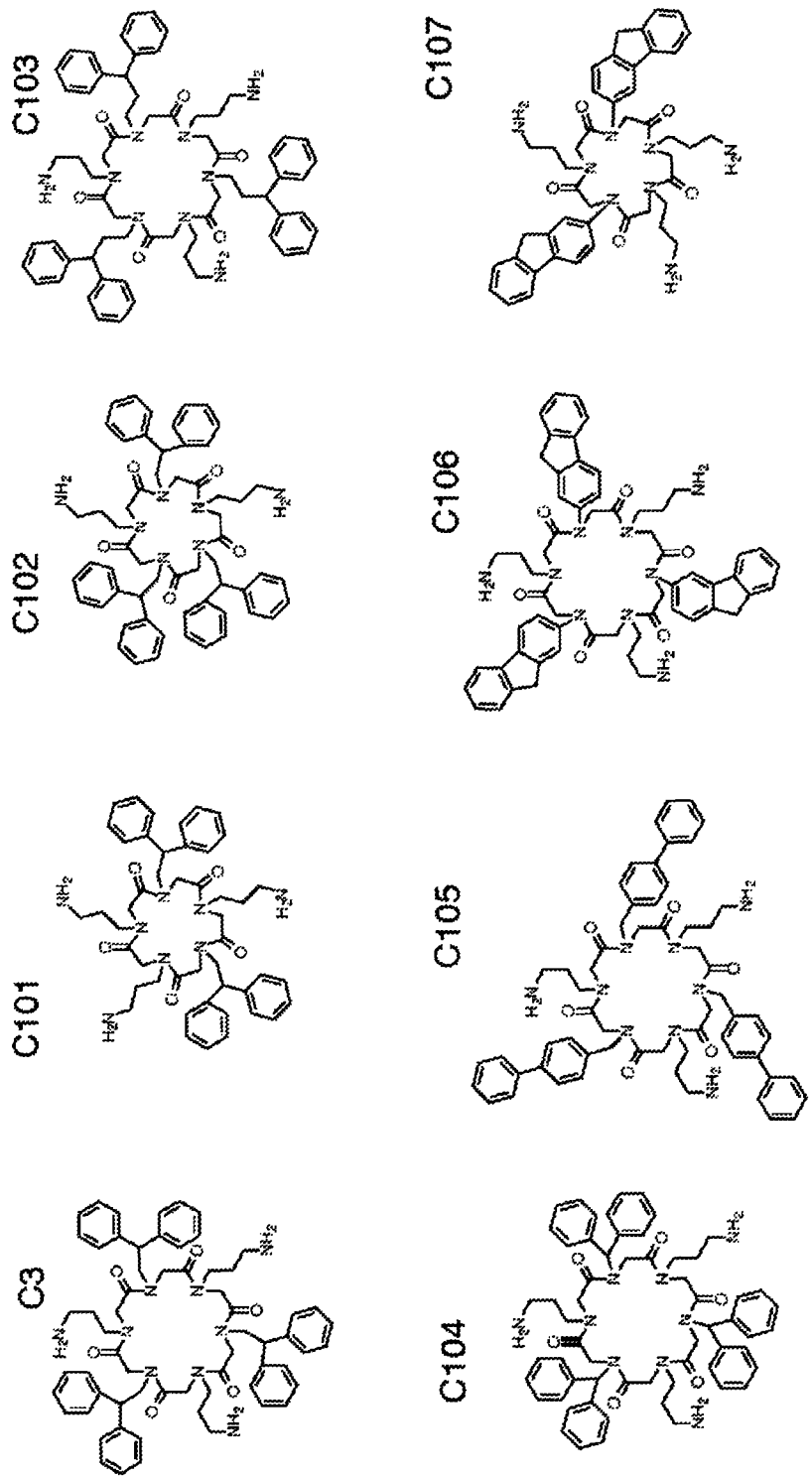
FIG. 13 shows structures of the representative cyclic peptoid compounds.
Figure 13:
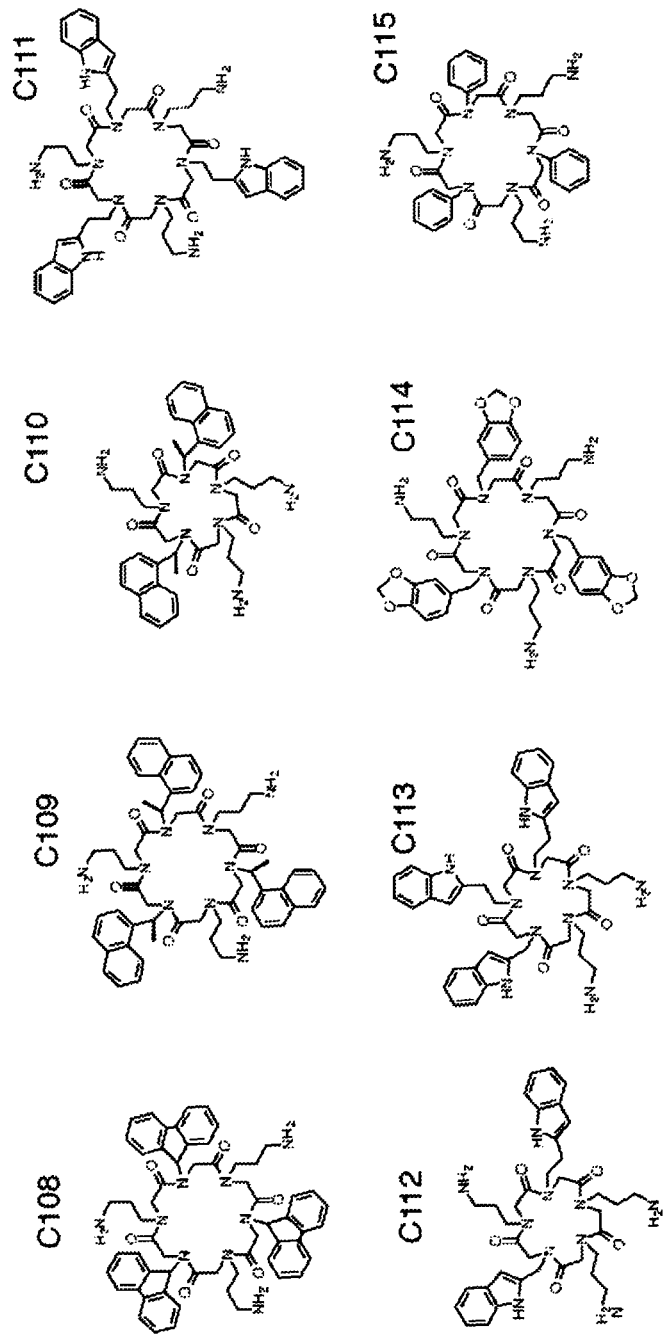
Figure 13:
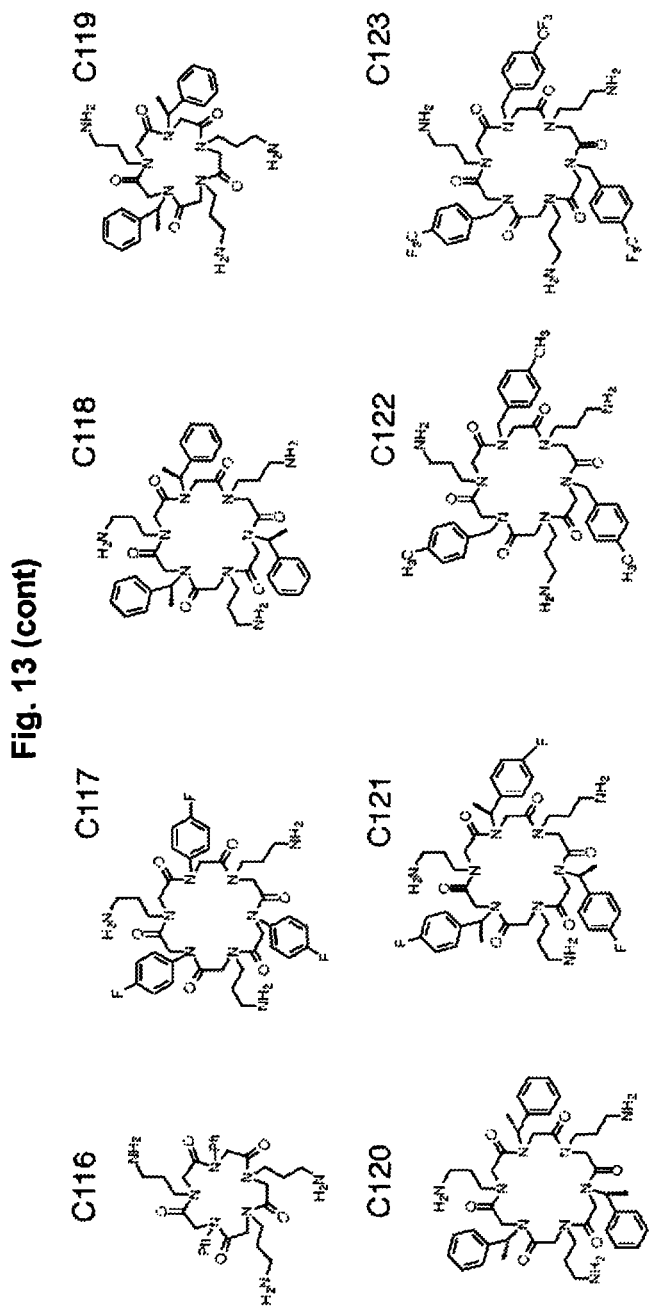
Figure 13:
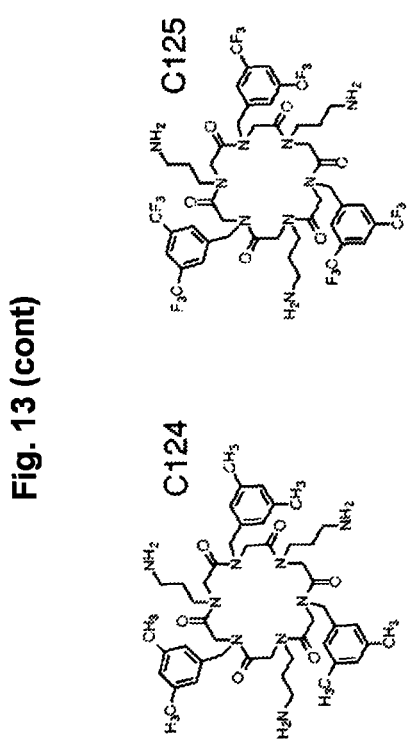

TABLE 1-continued
ESI mass spectrometric data of representative peptoid oligomers
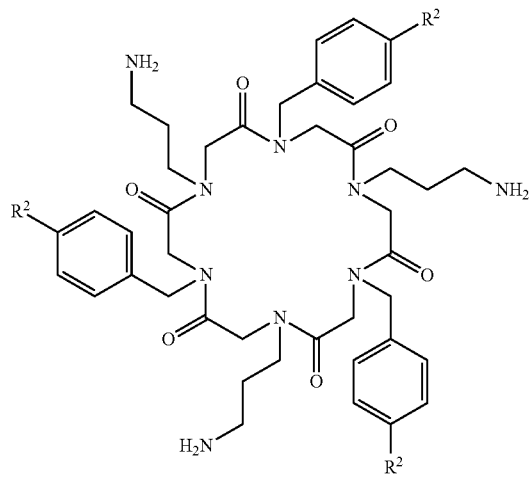
Va
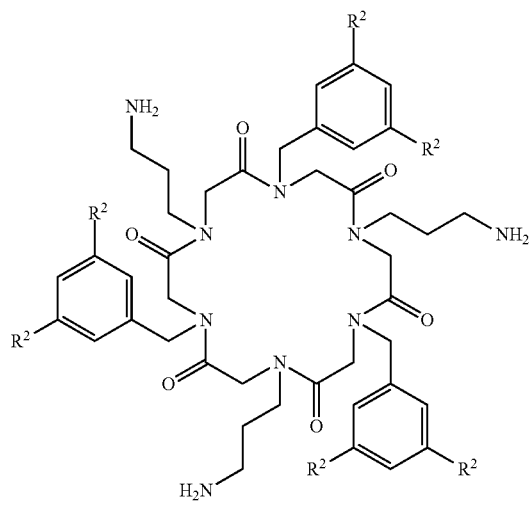
VIa
| # | Compounds | Chemical Structure | Calculated Mass[a] | Observed Mass |
|---|---|---|---|---|
| 31 | C(NgbNdp)$_5$ | 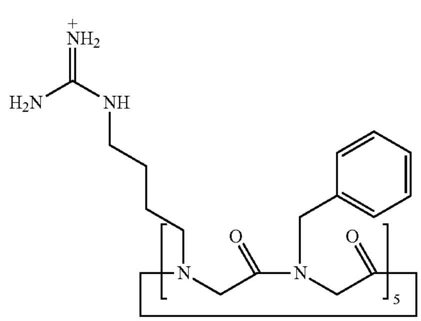 | 2036.16 | 510.1 (M + 4)/4 |
| C102 | C[(NapNdpp)$_2$Nap] | See FIG. 13 | 940.5 | 940.6 |
| C103 | C(NapNdpp)$_3$ | See FIG. 13 | 1096.6 | 1096.8 |
| C104 | C(NapNdpm)$_3$ | See FIG. 13 | 1012.5 | 1012.6 |
| C105 | C(NapNpp)$_3$ | Va (R$^2$ = Ph) | 1012.5 | 1012.6 |
| C106 | C(NapN2flene)$_3$ | See FIG. 13 | 1006.5 | 1006.6 |
| C122 | C(NapNpmpm)$_3$ | Va (R$^2$ = Me) | 825.49 | 826.5 (M + H) |

TABLE 1-continued
ESI mass spectrometric data of representative peptoid oligomers
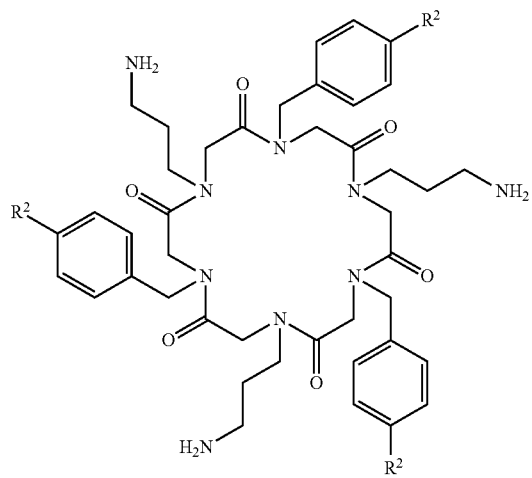
Va
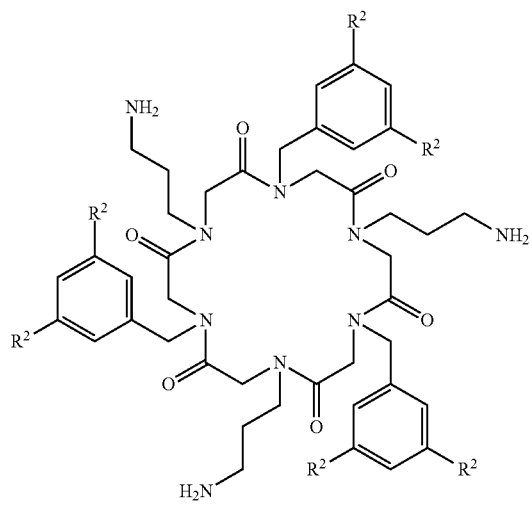
VIa
| # | Compounds | Chemical Structure | Calculated Mass[a] | Observed Mass |
|---|---|---|---|---|
| C123 | C(NapNptfmpm)$_3$ | Va (R$^2$ = CF$_3$) | 987.41 | 988.6 (M + H); 494.8 (M + 2/2) |
| C124 | C(NapNdmb)3 | VIa (R$^2$ = Me) | 867.54 | 868.5 (M + H); 434.9 (M + 2/2) |
| C125 | C(NapNbtfmb)3 | VIa (R$^2$ = CF$_3$) | 1191.37 | 1192.3 (M + H); 596.7 (M + 2/2) |
| C5-1 | | See below | 963.51 | 964.13 |
Side chain abbreviations are as described herein;
[a]Calculated mass = (M + H)/z;
C: cyclic.

Additional Representative Compounds
Additional representative compounds are given below.
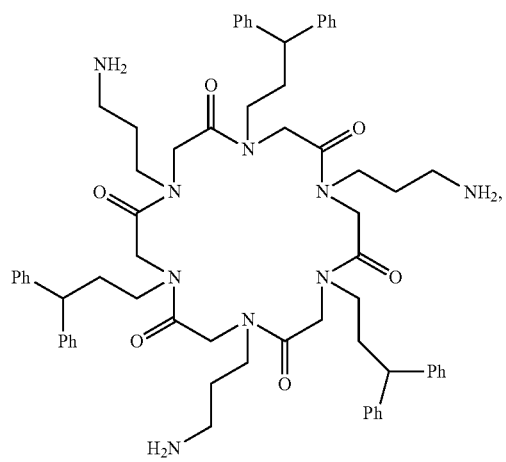
C103
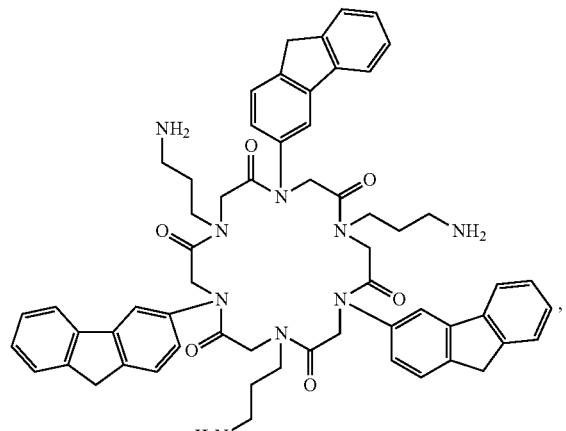
C106
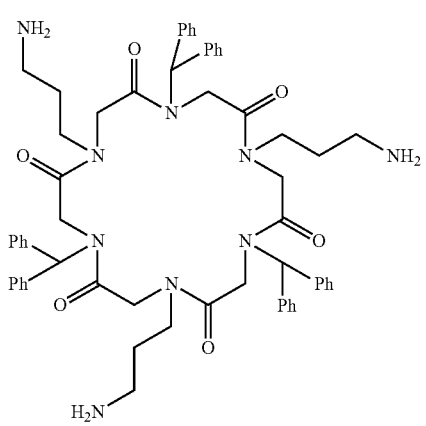
C104
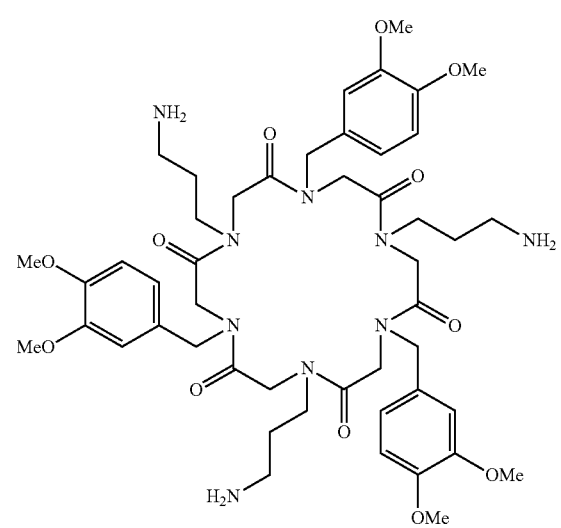
C5-1
The structures of the additional representative compounds are also presented in FIG. 13.
The following Table S3 lists HPLC retention time of the representative peptoids of the invention.

TABLE S3

ESI-MS and RP-HPLC characterization data for synthesized compounds. Side chain abbreviations are listed in Table S2. RP-HPLC analysis was conducted using a C18 column operated under a 5 to 95% acetonitrile in water (0.1% TFA) gradient at a 0.7 mL min$^{-1}$ flow rate monitored by UV absorbance at 214 nm.[a] Calculated mass = $(M + nH)^{n+}$.

| | Sequence | Calculated Mass[a] | Observed Mass(es) | Retention Time |
|---|---|---|---|---|
| C100 | C(NapNdp)$_3$ | [M + H]$^+$: 1054.6 | [M + H]$^+$: 1054.6 | 7.301 |
| C101 | C[(NapNdp)$_2$Ndpp] | [M + H]$^+$: 817.5 | [M + H]$^+$: 817.6 | 6.075 |
| C102 | C[(NapNdpp)$_2$Nap] | [M + H]$^+$: 940.5 | [M + H]$^+$: 940.6 | 7.615 |
| C103 | C(NapNdpp)$_3$ | [M + H]$^+$: 1096.6 | [M + H]$^+$: 1096.8; [M + 2H]$^{2+}$: 549.0 | 7.542 |
| C104 | C(NapNdpm)$_3$ | [M + H]$^+$: 1012.5 | [M + H]$^+$: 1012.6 | 6.942 |
| C105 | C(NapNpp)$_3$ | [M + H]$^+$: 1012.5 | [M + H]$^+$: 1012.6 | 6.800 |
| C106 | C(NapN2flene)$_3$ | [M + H]$^+$: 1006.5 | [M + H]$^+$: 1006.6; [M + 2H]$^{2+}$: 503.9 | 7.320 |
| C107 | C[(NapN2flene)$_3$Nap] | [M + H]$^+$: 785.4 | [M + H]$^+$: 785.5 | 5.957 |
| C108 | C(NapN9flene)$_3$ | [M + H]$^+$: 1006.5 | [M + H]$^+$: 1006.4; [M + 2H]$^{2+}$: 503.7 | 6.767 |
| C109 | C(NapNsne)$_3$ | [M + H]$^+$: 976.5 | [M + H$^+$]: 976.5; [M + $^{23}$Na]$^+$: 998.5 | 6.956 |
| C110 | C[(NapNsne)$_2$Nap] | [M + H]$^+$: 765.4 | [M + H]$^+$: 765.5 | 5.808 |
| C111 | C(NapNetrp)$_3$ | [M + H]$^+$: 943.5 | [M + H]$^+$: 943.6; [M + $^{23}$Na]$^+$: 965.7 | 5.875 |
| C112 | C[(NapNetrp)$_2$Nap] | [M + H]$^+$: 743.4 | [M + H]$^+$: 743.3; [M + 2H$^+$]$^{2+}$: 372.1 | 4.958 |
| C113 | C[(NapNetrp)$_2$Netrp] | [M + H]$^+$: 829.4 | [M + $^{23}$Na]$^+$: 852.5 | 6.383 |
| C114 | C(NapNpero)$_3$ | [M + H]$^+$: 915.4 | [M + H]$^+$: 916.4; [M + 2H$^+$]$^{2+}$: 458.7 | 4.975 |
| C115 | C(NapNar)$_3$ | [M + H]$^+$: 742.5 | [M + H]$^+$: 742.5; [M + $^{23}$Na]$^+$: 764.5 | 4.479 |
| C116 | C[(NapNar)$_2$Nap] | [M + H]$^+$: 609.3 | [M + H]$^+$: 609.4; [M + $^{23}$Na]$^+$: 631.4 | 2.664 |
| C117 | C(NapNpfa)$_3$ | [M + H]$^+$: 796.4 | [M + H]$^+$: 796.3; [M + 2H$^+$]$^{2+}$: 398.6 | 5.150 |
| C118 | C(NapNspe)$_3$ | [M + H]$^+$: 826.5 | [M + H]$^+$: 826.6; [M + $^{23}$Na]$^+$: 848.6 | 5.817 |
| C120 | C(NapNrpe)$_3$ | [M + H$^+$]: 826.5 | [M + H]$^+$: 826.6; [M + $^{23}$Na]$^+$: 848.6 | 5.746 |
| C121 | C(NapNspfpe)$_3$ | [M + H]$^+$: 880.5 | [M + H]$^+$: 880.4; [M + 2H]$^{2+}$: 440.7 | 5.677 |
| C122 | C(NapNpmpm)$_3$ | [M + H$^+$]: 826.5 | [M + H]$^+$: 826.5 | 5.900 |
| C123 | C(NapNptfmpm)$_3$ | [M + H$^+$]: 988.4 | [M + H]$^+$: 988.6; [M + 2H$^+$]$^{2+}$ 494.8 | 6.475 |
| C124 | C(NapNdmb)$_3$ | [M + H$^+$]: 868.5 | [M + H]$^+$: 868.5; [M + 2H$^+$]$^{2+}$: 434.9 | 6.592 |
| C125 | C(NapNbtfmb)$_3$ | [M + H$^+$]: 1192.4 | [M + H]$^+$: 1192.3; [M + 2H$^+$]$^{2+}$: 596.7 | 7.375 |
| Gramicidin S | C(VOLDFP)$_2$ | [M + H$^+$]: 1141.7 | [M + H]$^+$: 1141.7 | 8.512 |

EXAMPLES

The following examples are presented in order to more fully illustrate the preferred embodiments of the invention. They should in no way be construed, however, as limiting the broad scope of the invention.

Example 1

Antimicrobial Activity Screening.

The cyclic pentamers and hexamers were evaluated for antimicrobial activity against *S. aureus* LAC, a clinical isolate of MRSA. The antimicrobial assay was conducted using previously published procedures (CLSI Broth Macrodilution Procedures CLSI M07-A7). Compound C3 (Table 1, ID 20), which was previously identified as a "hit" compound due to its potent antimicrobial activity was included as a reference compound. The results reveal that cyclic peptoid hexamers and pentamers can display potent antimicrobial activity, with some oligomers exhibiting MIC values of 3.9 µg mL$^{-1}$. (Table 2, and FIG. 11). The antimicrobial activities of the oligomers in the library were also observed to maximize at 3.9 µg mL$^{-1}$, similar to other peptidomimetic antimicrobial systems (Porter et al, 2005, *J Am Chem Soc* 127, 11516-11529).

TABLE 2

Antimicrobial activity of representative peptoid oligomers

| # | Compound | Structure | MIC (µg mL$^{-1}$) |
|---|---|---|---|
| 20 (C3) | C(NapNdp)$_3$ | 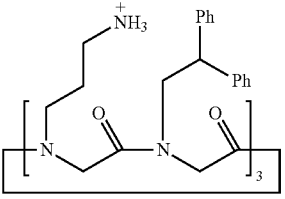 | 3.9-7.8 |
| 23 | C(NapNpm)$_3$ | Va (R$^2$ = H) | >500 |
| 30 | C(NabNpm)$_3$ | 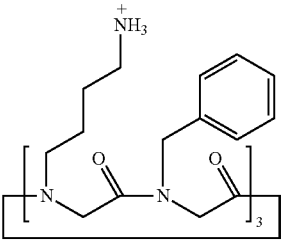 | 250 |
| 31 | C(NgbNdp)$_5$ | 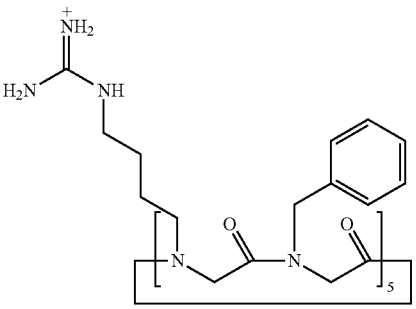 | 250 |
| C103 | C(NapNdpp)3 | See FIG. 13 | 3.9 |
| C104 | C(NapNdp)3 | See FIG. 13 | 3.9 |
| C105 | C(NapNpp)3 | Va (R$^2$ = Ph) | 3.9 |
| C106 | C(NapN2flene)3 | See above | 3.9 |
| C122 | C(NapNpmpm)$_3$ | Va (R$^2$ = Me) | 15.6 |
| C123 | C(NapNptfmpm)$_3$ | Va (R$^2$ = CF$_3$) | 3.9 |
| C124 | C(NapNdmb)$_3$ | VIa (R$^2$ = Me) | 3.9 |
| C125 | C(NapNbtfmb)$_3$ | VIa (R$^2$ = CF$_3$) | 3.9 |

The above data show that substitution on the phenyl ring improves the antimicrobial activity. It is noteworthy that within the context of conformationally-ordered antimicrobial peptoids (Chongsiriwatana et al. 2008. Proc Natl Acad Sci 105:2794-2799; Patch et al. 2003. J Am Chem Soc 125:12092-12093; Comegna et al. 2010. Bioorganic & Medicinal Chemistry 18:2010-2018; Huang et al. 2012. ChemMedChem 7:114-122), it is not intuitive to introduce substitutions into the phenyl ring to gain potent antimicrobial activity. In fact, several groups have studied the effects of varying peptoid side chain chemical groups with respect to antimicrobial activity (Chongsiriwatana et al. 2011. Antimicrob Agents Ch 55:5399-5402; Kapoor et al. 2011. Antimicrob Agents Ch 55:3054-3057; Kapoor et al. 2011. Antimicrob Agents Ch 55:3058-3062; Chongsiriwatana et al. 2011. Antimicrob Agents Ch 55:417-420), but no one has systematically investigated the effects of substituted phenyls.

It is, furthermore, known that enhancements in antimicrobial activity can be attained by substantially increasing the hydrophobicity of peptidomimetic oligomers. Accordingly, large increases in hydrophobicity are often implemented through the introduction of bulky hydrophobic groups, including naphthyl (Chongsiriwatana et al. 2008. Proc Natl Acad Sci 105:2794-2799) and long-chain alkyl groups (Chongsiriwatana et al. 2011. Antimicrob Agents Ch 55:417-420). The present inventors were, therefore, surprised to discover that relatively small increases in hydrophobicity imparted by small substitution(s) on phenyl rings resulted in dramatically enhanced antimicrobial activity.

As shown herein, C(NapNpm)$_3$ (#23 in Table 1), a cyclic peptoid hexamer with un-substituted phenyl rings, was inactive against *Escherichia coli* (MIC, minimum inhibitory concentration>500 μg mL$^{-1}$) and displayed moderate antimicrobial activity of 31.3 μg mL$^{-1}$ against *Staphylococcus aureus* (Huang et al., 2012, *ChemMedChem* 7, 114-122). C122, a cyclic peptoid hexamer with phenyl rings monosubstituted with a methyl group at the para position, displayed relatively improved antimicrobial activity of 15.6 μg mL$^{-1}$ against MRSA. C124, an exemplary antimicrobial compound of this genus, is a cyclic peptoid hexamer with phenyl rings di-substituted with two methyl groups at meta positions that displayed potent antimicrobial activity of 3.9 μg mL$^{-1}$. The additional methyl unit in C124 compared to C122 conferred only a small increase in hydrophobicity (a 0.7 min increase in retention time, R$_f$=6.6 vs. 5.9, respectively on a C$_{18}$ RP-HPLC column), but surprisingly also conferred a four-fold increase in antimicrobial activity. Fluorinated versions of the peptoid compound generally exhibit increased or similar hydrophobicity as evidenced by RP-HPLC retention time. These compounds, accordingly, also displayed enhanced antimicrobial activities than their corresponding hydrocarbon analogs.

Antimicrobial Activity in the Presence of Serum.

The bioactivities of compounds C124 and C125 were further evaluated. Compounds C3 and Gramicidin S (Table 1, ID 17) (Gause, et al, *Nature*, 1944, 154, 703-703) were also included to allow comparisons to a member of the previous cyclic peptoid library and a cyclic antimicrobial peptide. The antimicrobial activities of these four compounds were evaluated in the presence of serum. Such a consideration is critical in evaluating the potential of antimicrobial compounds to be used systemically, as serum components (e.g. proteins) may complicate antimicrobial activity. The assay was conducted similarly as described above, with the media supplemented with 50% normal human serum (NHS).

The MIC values in serum for compounds C3, C124, C125, and Gramicidin S were determined to be 15.6 μg mL$^{-1}$, 15.6 μg mL$^{-1}$, 62.5 μg mL$^{-1}$, and 31.3 μg mL$^{-1}$, respectively. The MIC values for all the compounds were observed to increase in the presence of serum, indicating the retention of antimicrobial activity with varying degrees of inactivation. C3 and C124 exhibited an approximately four-fold decrease in anti-microbial activity in serum, and the antimicrobial activity of C125 decreased sixteen-fold (Table 3).

Minimum Inhibitory Concentrations (MIC) were determined against *S. aureus* LAC in RPMI media supplemented with or without normal human serum (NHS). The 10% hemolytic dose was determined from lysis of human erythrocytes. A selectivity ratio (SR) is defined as HC$_{10}$/MIC. Cytotoxicity assays were performed using a CellTiter kit with HeLa cells. LD$_{50}$: 50% lethal dose. TI: therapeutic index defined as LD$_{50}$/MIC.

TABLE 3

Bioactivities of select representative compounds

| Compound | MIC[a] [μg mL$^{-1}$] | MIC + NHS[b] [μg mL$^{-1}$] | HC$_{10}$[c] [μg mL$^{-1}$] | SR[d] | LC$_{50}$[e] [μg mL$^{-1}$] | TI[f] |
|---|---|---|---|---|---|---|
| 20 (C3) | 3.9 | 15.6 | 31.3 | 8 | 63 | 16 |
| 23 | 500 | | >250 | | | |
| 30 | 500 | | >250 | | | >1 |
| 31 | 250 | | >62.5 | | | >1 |
| C124 | 3.9 | 15.6 | 125 | 32 | 180 | 45 |
| C125 | 3.9 | 62.5 | 31.3 | 8 | 47 | 12 |
| Gramicidin S | 31.3 | 31.3 | 15.6 | 0.5 | 31.3 | 1 |

[a] Minimum Inhibitory Concentrations against MRSA USA300 (Dunman et al, *J. Clin. Microbiol.* 2006, 44, 108-118; Fridkin et al, *J. A. M. A.* 2007, 298, 1763-1771). [b] MIC values against MRSA USA300 in 50% (v/v) normal human serum (NHS). [c] HC$_{10}$ represents the concentration of antimicrobial required to lyse 10% of human erythrocytes. [d] SR (selectivity ratio) values are defined as the ratio HC$_{10}$/MIC. [e] LC$_{50}$ (50% lethal concentration) represents the concentration of antimicrobial required to kill 50% of HeLa cells. [f] Therapeutic indices (TI) are calculated as the ratio LC$_{50}$/MIC.

Improved Selectivity of Peptoid C124.

A detrimental property of most AMPs is their toxicity towards host cells due to non-specific interactions with eukaryotic membranes. Thus, the development of antimicrobial oligomers is often aimed at maximizing antimicrobial activity while minimizing eukaryotic cell toxicity. The inventors therefore sought to determine the toxicity of the cyclic peptoids by measuring hemolytic activity. The concentration of antimicrobial compound required to lyse 10% of human erythrocytes (HC$_{10}$) following incubation for 1 hour at 37° C., was determined. These experiments revealed that gramicidin S exhibited an HC$_{10}$ of 15.6 μg mL$^{-1}$, whereas molecules C3 and C125 both exhibited an HC$_{10}$ of 31.3 μg mL$^{-1}$ (Table 3).

Selectivity ratio (SR) values are often calculated as the ratio of hemolytic to antimicrobial activity. SR values can be calculated using different metrics of hemolytic activity (e.g., HC$_{50}$ and HC$_{10}$ to yield SR$_{50}$ and SR$_{10}$ values, respectively). The determination of selectivity using SR$_{10}$ values is a more stringent parameter than SR$_{50}$ values. Large SR$_{10}$ values indicate that a compound possesses potent antimicrobial activity and low hemolytic activity, corresponding to a high specificity for prokaryotic versus eukaryotic cytotoxicity.

AMP-mimics have been reported to exhibit values that approach $SR_{10}$=30 (Chongsiriwatana, et al, *Proc. Natl. Acad. Sci. U.S.A.* 2008, 105, 2794-2799; Mowery, et al, *J. Am. Chem. Soc.* 2007, 129, 15474-15476) and $SR_{50}$=200 (Choi, et al, *Proc. Natl. Acad. Sci. U.S.A.* 2009, 106, 6968-6973). In previous work, the inventors reported that a cyclic peptoid octamer displayed a significant 32-fold selectivity ($SR_{10}$=32) for *E. coli* bacterial cells versus human erythrocytes. In this work, the inventors aimed to achieve similar or greater selectivity ($SR_{10} \geq 32$) for *S. aureus* versus human erythrocytes by cyclic peptoid oligomers. The results confirm the strongly hemolytic nature of gramicidin S, which displayed an $SR_{10}$=0.5 (Table 3). Both C3 and C125 are moderately selective, exhibiting $SR_{10}$=8. On the other hand, compound C124 displayed substantial selectivity ($SR_{10}$=32), establishing that significant selectivity for *S. aureus* versus human erythrocytes can be achieved with cyclic peptoid hexamers. The comparison between C124 and C125 reveals that fluorination deters selectivity.

Figure 3:
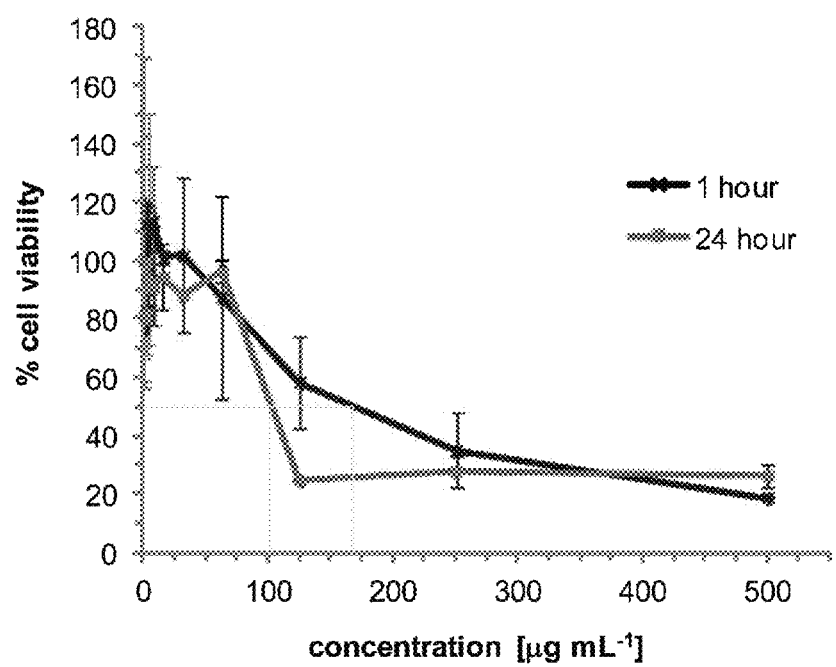
FIG. 3 shows cytotoxicity of compound C124 toward HeLa cells. $LC_{50}$ (50% cell viability) within 1 hour of incubation with C124 was determined to be ~180 µg $mL^{-1}$, and $LC_{50}$ within 24 hours of incubation was determined to be ~100 µg $mL^{-1}$.
Figure 4:
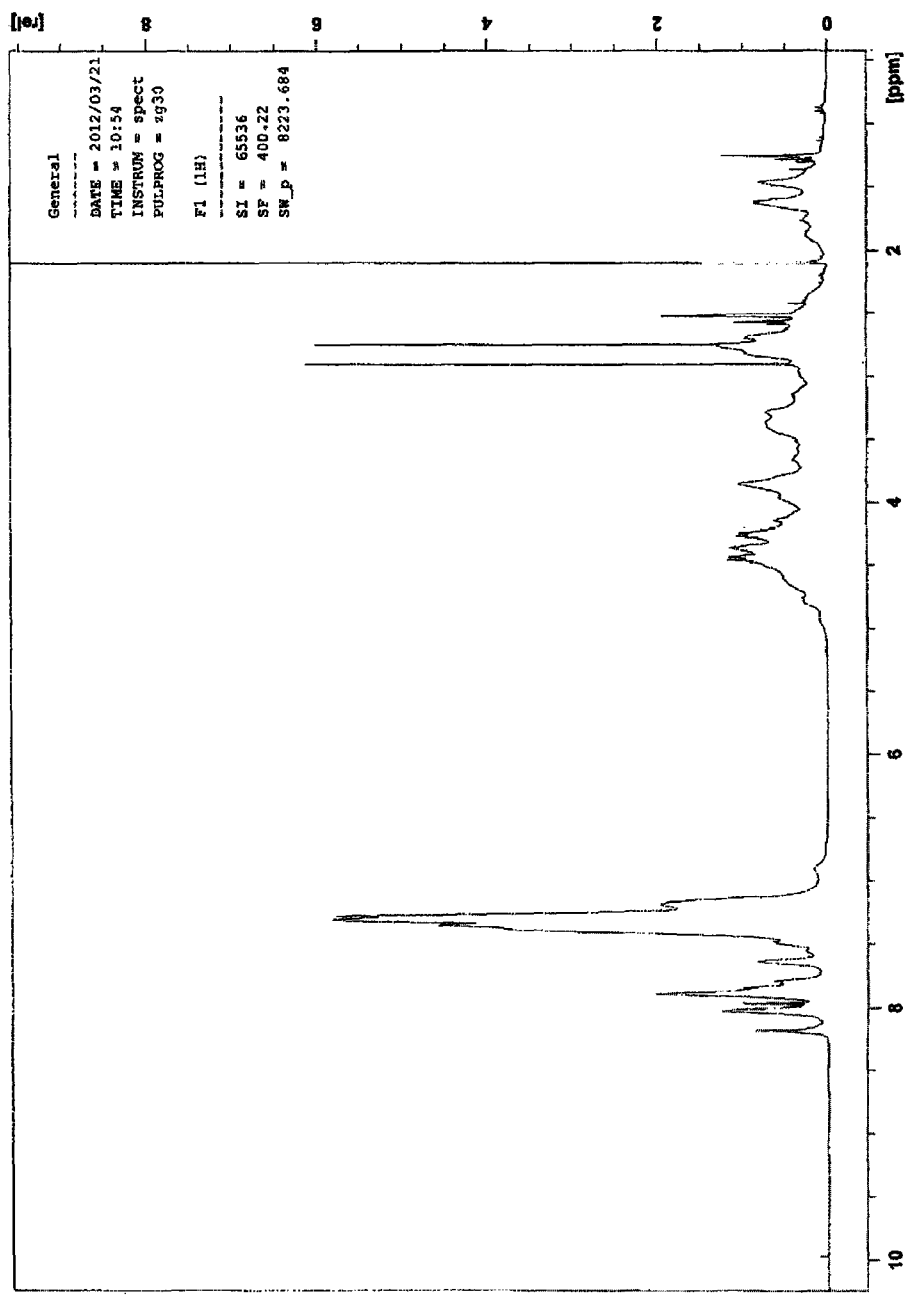
FIG. 4 shows $^1H$ NMR spectra of Compound C124 in DMSO-d6.
Figure 5:
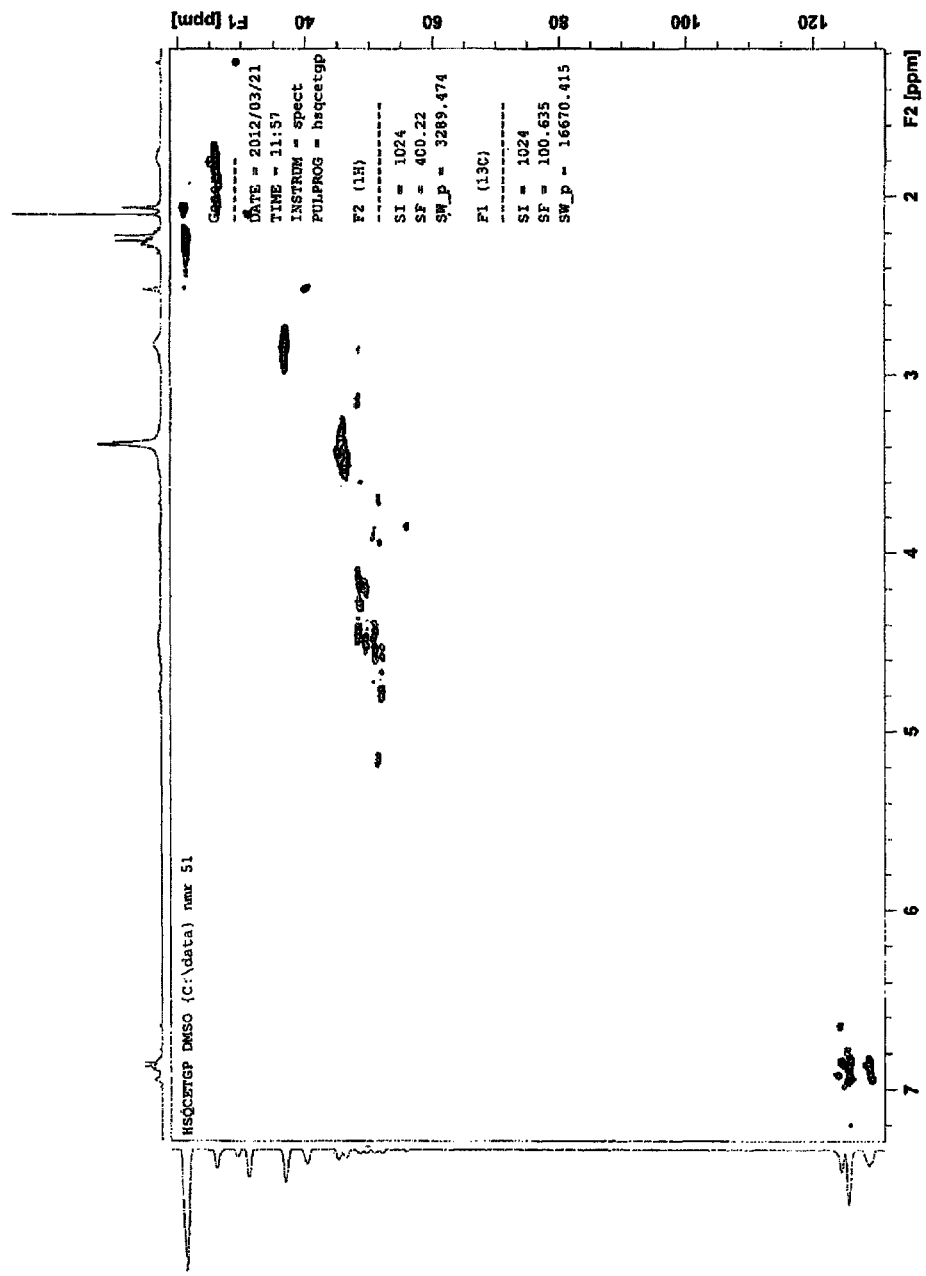
FIG. 5 shows $^1H$-$^{13}C$ HSQC spectra of Compound C124 in DMSO-d6.
Figure 6:
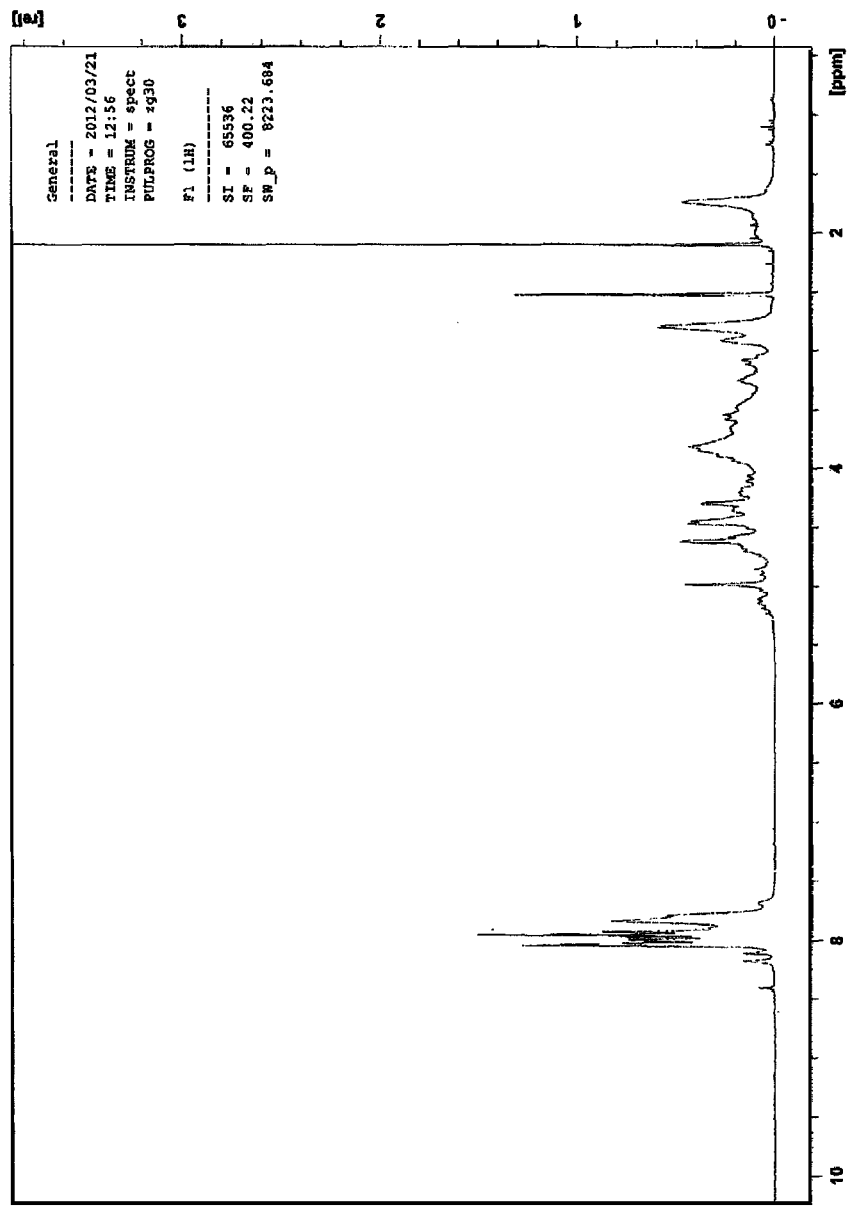
FIG. 6 shows $^1H$ NMR spectra of Compound C125 in DMSO-d6.
Figure 7:
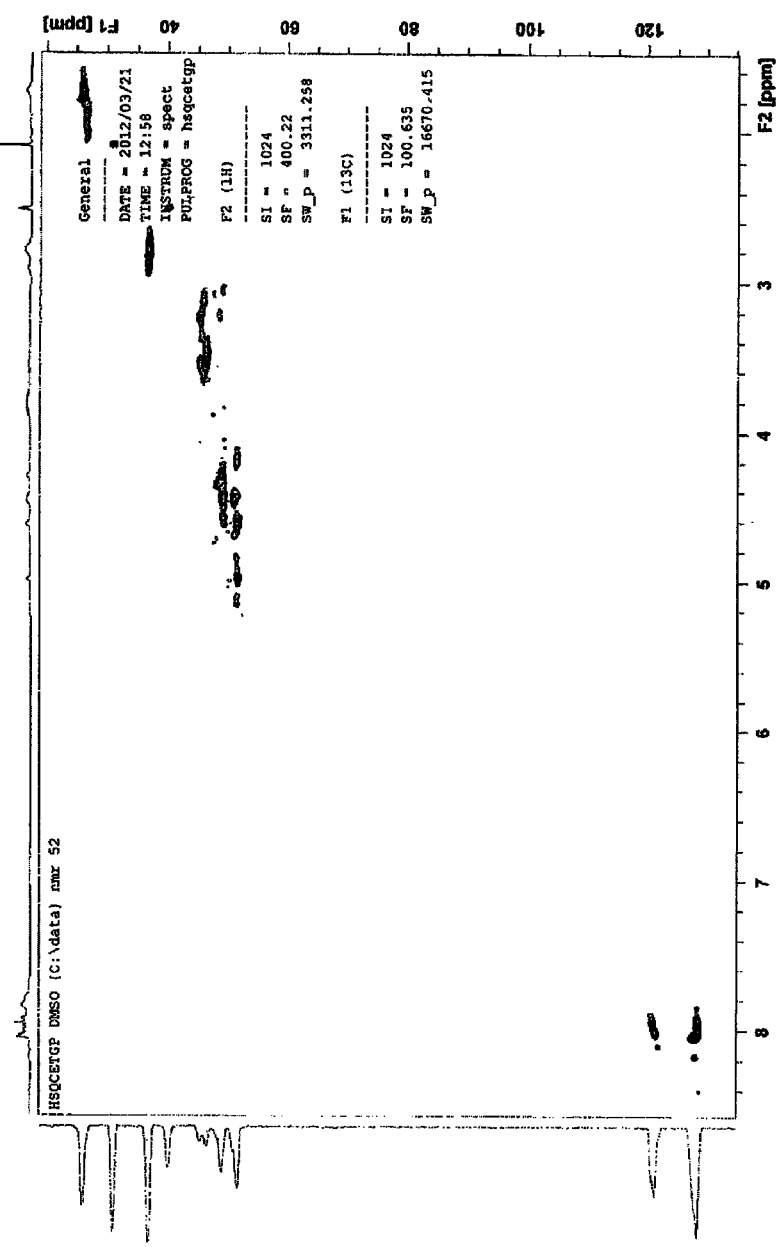
FIG. 7 shows $^1H$-$^{13}C$ HSQC spectra of Compound C125 in DMSO-d6.
Figure 8:
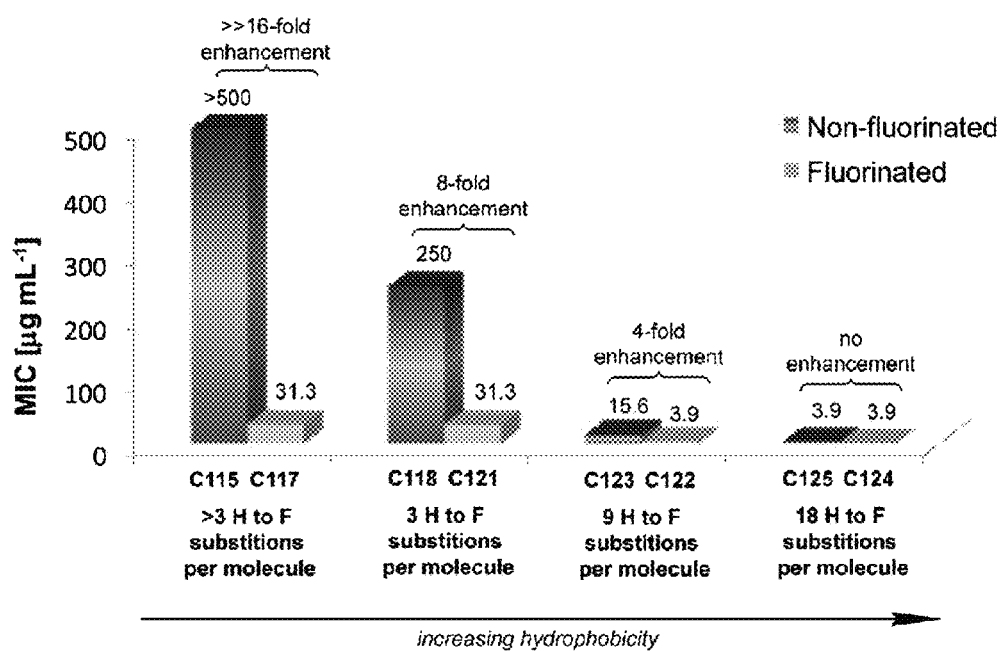
FIG. 8 shows comparison of the antimicrobial activities of non-fluorinated cyclic peptoids and their fluorinated counterparts against MRSA USA300. Fluorinated cyclic peptoids generally exhibited greater antimicrobial activity than their non-fluorinated counterparts (e.g., C117>C115, C121>C118, C123>C122). The enhancement in antimicrobial activity was observed to decrease with increasing hydrogen to fluorine atom substitutions, as seen in the comparison above. The fluorinated analogs of cyclic peptoids that are sufficiently hydrophobic possess similar potency as their hydrocarbon counterparts (C125=C124).

As an additional parameter of selectivity, the inventors also evaluated the compounds for toxicity towards nucleated mammalian cells (FIG. 3). The compounds were incubated with HeLa cells for 1 hr at 37° C. and cell viability was determined by a dye-based assay. The concentration of compound that yielded 50% lethality ($LC_{50}$), was determined. Compounds C3, C124, C125, and gramicidin S exhibited $LC_{50}$ values of 63 µg mL$^{-1}$, 180 µg mL$^{-1}$, 47 µg mL$^{-1}$, and 31.3 µg mL$^{-1}$, respectively (Table 3).

Therapeutic indices (TI), defined as the ratio $LC_{50}$/MIC, were determined for each compound as a measure of selective toxicity for bacterial over mammalian cells. All the peptoids in this series exhibited more favorable TI values than gramicidin S (TI=1). C3 displayed a TI=16, whereas C124 and C125 displayed TI=45 and 12, respectively. The high TI value calculated for C124 relative to C3 signifies the substantial improvement in pharmacological attributes obtained with the new library of cyclic peptoids, since C124 is smaller in size (MW=868 Da) than C3 (MW=1053 Da) and is water-soluble at $\geq$15 mg mL$^{-1}$ concentrations.

In Vivo Safety and Efficacy.

Despite promising in vitro data, the development of membrane-active antimicrobials as therapeutic agents for the treatment of bacterial infections has often been stifled by toxicity and pharmacodynamic problems. To date, only a small number of peptidomimetic oligomers have been shown to be effective antimicrobial agents in vivo. (Choi et al, 2009, *P Natl Acad Sci USA* 106, 6968-6973; Fernandez-Lopez et al, 2001, *Nature* 412, 452-455; Vallon-Eberhard et al, 2008, *Antimicrob Agents Ch* 52, 3118-3126) Thus, membrane-active peptoid antimicrobials that demonstrate efficacy in vivo possess substantial potential as therapeutic agents and further support the promise of peptoids as drug molecules (Zuckermann et al, *Curr Opin Mol Ther* 11, 299-307)

Membrane Damage.

Figure 2:
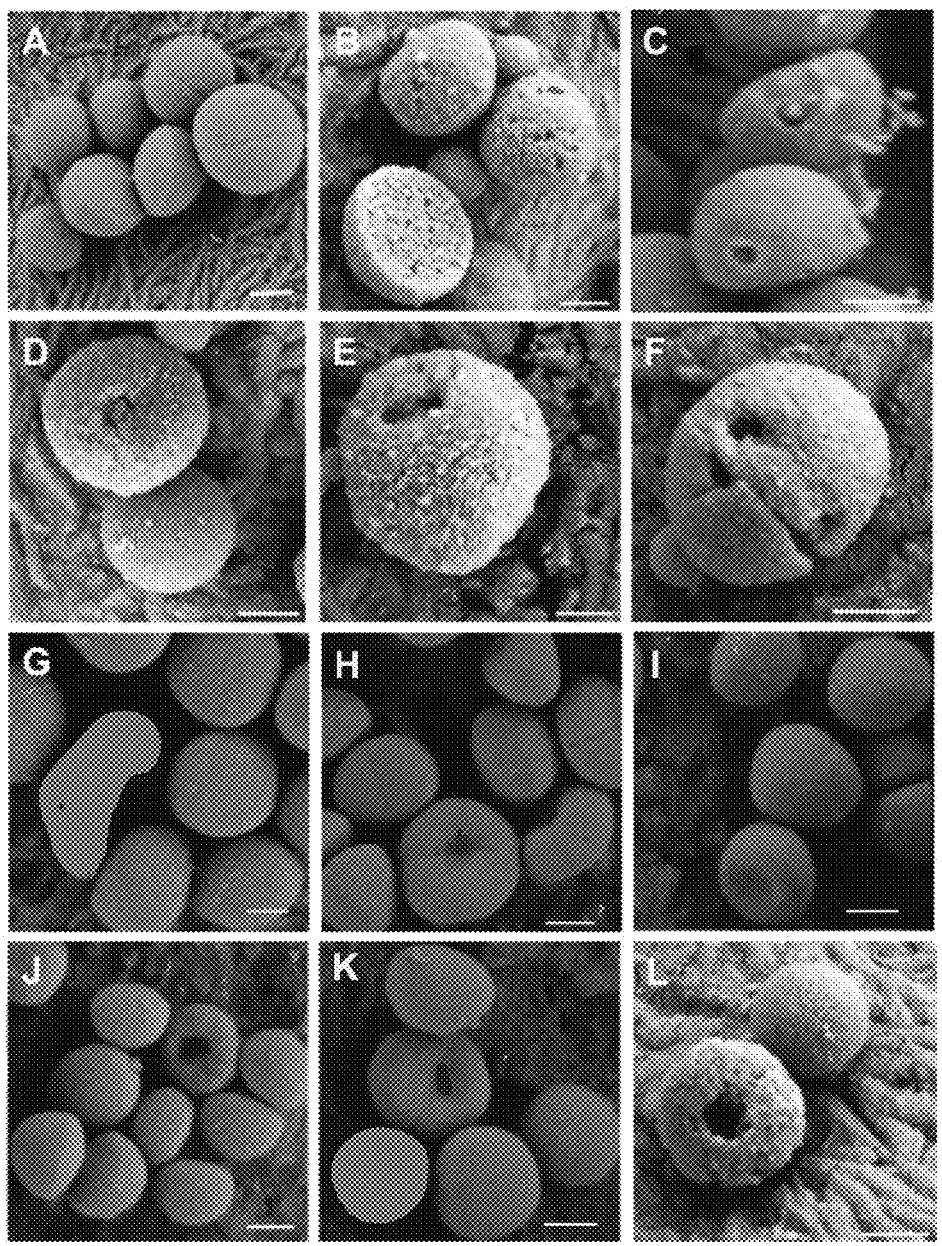
FIG. 2 shows scanning electron micrographs of untreated (A) *S. aureus* cells and those treated with cyclic peptoid antimicrobials (B to I). Membrane damage caused by cyclic peptoid oligomers is depicted. Untreated MRSA USA300 cells (A) appear spherical with smooth cell surfaces, whereas cells treated with the antimicrobial peptoids C3 (B to F) and C124 (G to L) exhibited depressions (G to I), small pores (B, C, D, J, and K) or large craters (E, F, and L). Scale bar: 300 nm. Bacterial cells were incubated with C3 at its MIC (3.9 µg $mL^{-1}$) for 1 hour (C) or 18 hours (B, D, E, and F), or C124 for 1 hour at sub-MIC (1.95 µg $mL^{-1}$, G to J) or MIC values (3.9 µg $mL^{-1}$; K and L).

AMPs have long been thought to exert their bactericidal activities by interacting with negatively-charged bacterial membranes (Zasloff, *Nature* 2002, 415, 389-395; Ivankin, et al, *Angew. Chem. Int. Ed.* 2010, 49, 8462-8465). While the exact mode of action has yet to be fully understood, the interaction of the AMP eventually leads to damage of the bacterial membrane that is visible by scanning electron microscopy (SEM). (Hartmann et al, 2010, *Antimicrob Agents Ch* 54, 3132-3142) SEM was used to examine the morphological changes which occur to the *S. aureus* cell surface upon exposure to peptoid antimicrobials (FIG. 2).

Figure 9:
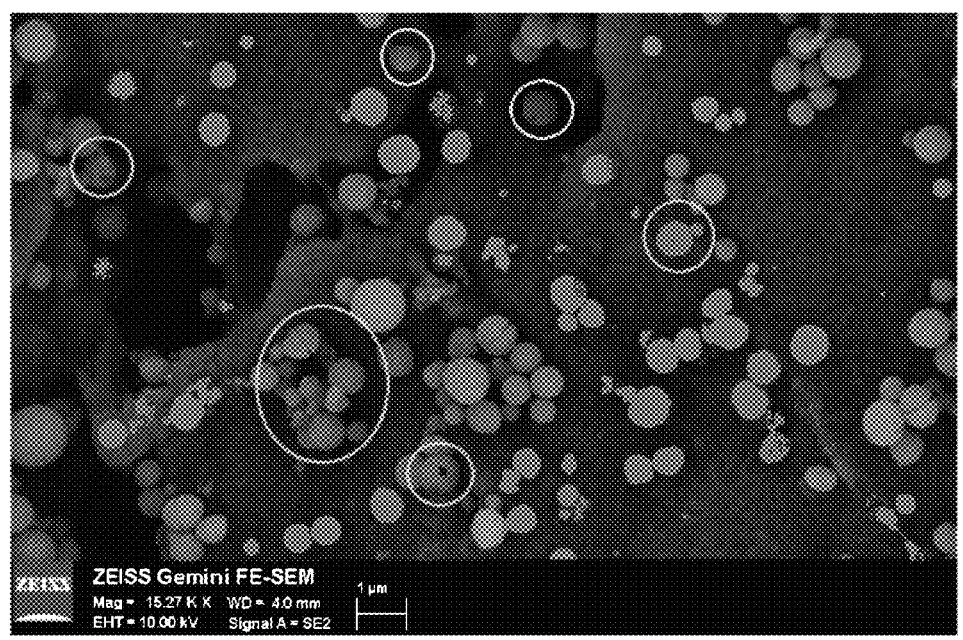
FIG. 9 shows representative SEM images collected for compound C124 (at MIC=3.9 µg mL-1) under 10.0 kV. Yellow circles highlight damaged cell surfaces which display pores.

SEM images of untreated *S. aureus* cultures showed smooth cell surfaces with varying cell diameters from 500-800 nm (FIG. 2A). The cells appeared roughly spherical and occurred in grape-like clusters. Dividing cells were also observed. Cells treated with sub-MIC, MIC, or supra-MIC of compounds C3 and C124 exhibited cell surface damage (FIG. 2B to L). The effects of the different compounds, incubation times (1 hr vs. 18 hr), and concentrations (sub-MIC, MIC, or supra-MIC) on cell morphologies were not readily distinguishable by SEM. Some cell surfaces were observed to collapse upon treatment with the antimicrobial peptoids (FIG. 2G-I). The formation of small pores (FIGS. 2B-D, J, and K) and large craters (FIGS. 2E,F and L) were also observed, with some present near or at the division hemisphere (septum). These features were consistently observed in microscopy images obtained for antimicrobial-treated bacterial cells (FIG. 9).

Methods:

Antimicrobial Susceptibility Assays (Method a).

Antimicrobial susceptibility assays were conducted in 96-well plates using the broth microdilution procedure outlined in the document M07-A7 of the CLSI (Clinical and Laboratory Standards Institute. Methods for Dilution Antimicrobial Susceptibility Tests for Bacteria That Grow Aerobically-Seventh Edition: Approved Standard CLSI document M07-A7. CLSI, Wayne, USA, 2006). Screens against *Staphylococcus aureus* LAC, MW2, Newman, and RN6734 were conducted in RPMI (Roswell Park Memorial Institute) medium. For assays in serum, normal human pooled serum (NHS) was filtered through a 0.45 µm syringe filter (Pall) prior to dilution with RPMI, such that each well contained 50% (v/v) NHS. Experiments were conducted in three independent replicates of three parallel trials to ensure statistical significance.

Antimicrobial Assays (Method B).

MRSA pulse-field gel electrophoresis types USA300 (strain LAC) (Kennedy, et al, *Proc. Natl. Acad. Sci. U.S.A.* 2008, 105, 1327-1332) and USA500 (BK2395) (Alonzo, 3rd, et al, *Mol. Microbiol.* 2012, 83, 423-435) were used in this study. *S. aureus* were grown in tryptic soy broth (BD Biosciences) as described previously. (Alonzo) Antimicrobial susceptibility assays were conducted in 96-well plates using the broth macrodilution procedure outlined in the document M07-A7 of the CLSI. (Clinical and Laboratory Standards Institute. Methods for Dilution Antimicrobial Susceptibility Tests for Bacteria That Grow Aerobically-Seventh Edition: Approved Standard CLSI document M07-A7. CLSI, Wayne, USA, 2006). The screens against *Staphylococcus aureus* LAC were conducted in either LB (Luria-Bertani) or RPMI medium. For assays in serum, normal human pooled serum (NHS) was filtered through a 0.45 µm syringe filter (Pall) prior to dilution with RPMI, such that each well contained 50% (v/v) NHS. Experiments were conducted in three independent replicates of three parallel trials to ensure statistical significance.

Hemolysis Assays.

Hemolysis assays were conducted in 96-well plates using fresh human erythrocytes in PBS (phosphate-buffered saline) solution. Erythrocytes treated with a detergent (1% Triton X-100) solution were used as a positive control for erythrocyte lysis, and vehicle buffer (PBS) was used as a negative control. Hemolytic percentages were defined as $[(A-A_{testblank})/(A_{control}-A_{blank})] \times 100$, where A is the absorbance of the test well and $A_{control}$ the average absorbance of wells with erythrocytes exposed to PBS but no antimicrobial, $A_{testblank}$ (PBS and antimicrobial) and $A_{blank}$ (PBS only). Experiments were conducted in three independent replicates of three parallel trials to ensure statistical significance.

Killing Assay.

Killing assays were conducted by placing aliquots of bacteria incubated with the peptoid at different times in TSB or LB plates. CFU (colony forming units) per mL were determined by standard plate counting after drying the plates overnight at 37° C.

Cytotoxicity Experiments (Description A).

HeLa cells (~1×10$^6$ cells per well) were seeded in a tissue culture-treated 96-well plate (Corning). The cells were monitored for confluence via light microscopy prior to the addition of compounds to a final volume of 100 μL/well. Following incubation with the compounds (for 1 hour or 24 hours at 37° C.), Cell Titer (Promega) was added to each well and the assay was allowed to develop for 1 hour at 37° C. Absorbance was then read at 490 nm using a Wallac Envision plate reader. The experiments were always conducted in triplicate with water or ethanol as the negative control. Percent cell viability (% CV) was calculated as the ratio of mean absorbance of the test wells and the mean absorbance of the water or ethanol treated wells.

Cytotoxicity Assays (Description B).

Following seeding in DMEM supplemented with 10% v/v FBS (fetal bovine serum) in tissue-culture plates (Corning), adherent HeLa cells were trypsinized, washed in PBS, and re-suspended in medium at a density of 1×10$^6$ cells/mL. A 100 μL cell suspension was seeded onto a 96-well plate and cultured for 25 hrs. Subsequently, cells were exposed to the different compounds for 1 and 24 hrs and the cell viability evaluated using CellTiter 96® AQueous Non-Radioactive Cell Proliferation Assay (Promega).

Scanning Electron Microscopy.

SEM samples were prepared following the procedure outlined in Hartmann et al (2012, *Antimicrob Agents Ch* 54:3132-3142). Mid-exponential *S. aureus* LAC in LB medium (10 g/L tryptone and 5 g/L yeast, pH 7.4) was prepared by diluting an overnight culture of *S. aureus* LAC in LB media till OD$_{600}$~0.4 (approximately 3 hours at 37° C.). The culture was then treated with the antimicrobial compound at the MIC as well as two-fold higher and lower concentrations of the MIC (previously determined for cell density at OD$_{600}$~0.4 for 1 hour or 24 hours at 37° C. Samples were then centrifuged (6000×g, 20 min), washed with a phosphate-buffered saline solution (PBS), and the cell suspension was placed on a 1 cm$^2$ piece of membrane filter (Millipore 0.45 μm) to dry. The samples were then fixed with 8% glutaraldehyde (Alfa Aesar) for 1 hour at RT, washed with PBS, and fixed with 0.5% osmium tetroxide (Electron Microscopy Sciences) at 4° C. overnight. After washing with PBS, the samples were treated with 30% ethanol for 10 minutes, 3% uranyl acetate (Electron Microscopy Sciences) in 30% ethanol/water, 50% ethanol for 10 minutes, and 70% ethanol overnight at 4° C. The membrane pieces were then dried at room temperature, attached to an aluminum pin stub with a carbon conductive adhesive (PELCO), and sputter-coated (Electron Microscopy Sciences coater EMS1505ES) with a 5 nm layer of gold, and imaged with a Zeiss Merlin FESEM under SE2 detection at 2.0-4.0 kV.

Example 2

In order to assess the ability of the peptoid oligomers described herein to act as antimalarial agents, fluorescence-based in vitro antimalarial assays were performed. The protocol used to perform these assays was adapted from that described by Smilkstein et al. (2004, Antimicrobial Agents and Chemotherapy 48:1803-1806; the entire content of which is incorporated herein by reference) and is set forth below.

Determining Drug Toxicity on *P. falciparum* Parasites Using SYBR Green Method

Reagents Required:

*Plasmodium falciparum* 3D7 erythrocytic asexual culture, at 5% hematocrit maintained in the atmospheric conditions of 1% oxygen, 5% carbon dioxide and 94% nitrogen; complete media (RPMI 1640, 25 mM HEPES, 10 ug/ml gentamycin, 0.5 mM hypoxanthine, pH 6.75), supplemented with 25 mM sodium bicarbonate and 0.5% Albumax II; SYBR Green I nucleic acid staining dye (Molecular Probes), 10000× stock, stored at −20° C.; and Lysis Buffer.

Lysis Buffer:

20 mM Tris, pH 7.5; 5 mM EDTA; 0.008% saponin; and 0.08% Triton X-100.

Cultures are maintained by changing the medium daily and keeping parasitemia below 6%. When performed, parasite cultures are synchronized using a MACS cell separation column (Miltenyi Biotec). To determine parasitemia, the number of parasitized erythrocytes from 500 cells in a Giemsa stained blood smear are counted.

Drug Treatment:

1. Add 100 μL of warm (37° C.) complete media containing drug to each well of a 96 multi-well clear, sterile plate.
2. Add 100 μL of *Plasmodium falciparum* 3D7 culture to each well containing drug at 0.25% parasitemia (synchronous ring stage can be used) and 10% hematocrit (final hematocrit will be 5%).
3. Maintain treated cultures under the atmospheric conditions of 1% oxygen, 5% carbon dioxide and 94% nitrogen for 96 hours.
4. After 96 hours of growth*, freeze at −80° C. overnight.
   *Note: Growth can be examined by pipetting 5 from desired wells onto slides and creating blood smears. Do not mix wells prior to pipetting and pipette from bottom of well where blood has settled.
5. After freezing, thaw at 37° C. for 4 hours.
6. Transfer 100 μL, pipetting wells up and down to mix, to a black, sterile 96 well plate.
7. Create working solution of 0.2 μL of SYBR Green per 1 mL of lysis buffer, and add 100 μL of this solution to each well, pipetting up and down to mix/lyse erythrocytes. *Note: mixture should be a translucent red color.
8. Incubate at room temperature, protected from light, on a shaker for 1 hour.

Measure the fluorescence using excitation and emission wavelengths of 485 and 530 nm, respectively. The above method is provided courtesy of the Rodriguez laboratory of New York University.

Figure 12A:
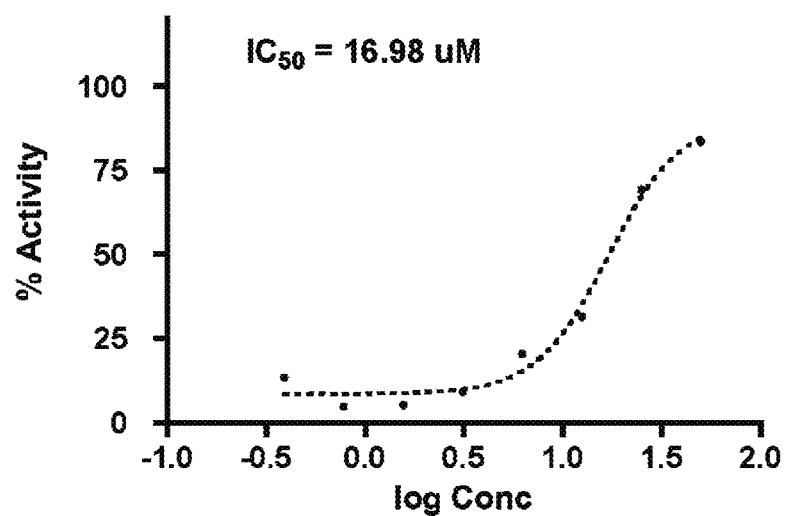
FIGS. 12a and b show graphs depicting the $IC_{50}$ results for Peptoid 3-15 (C124) and Peptoid 5-1 relative to those determined for chloroquine. Each of these compounds displays significant activity with respect to the ability to inhibit growth of *P. falciparum*.
Figure 12B:
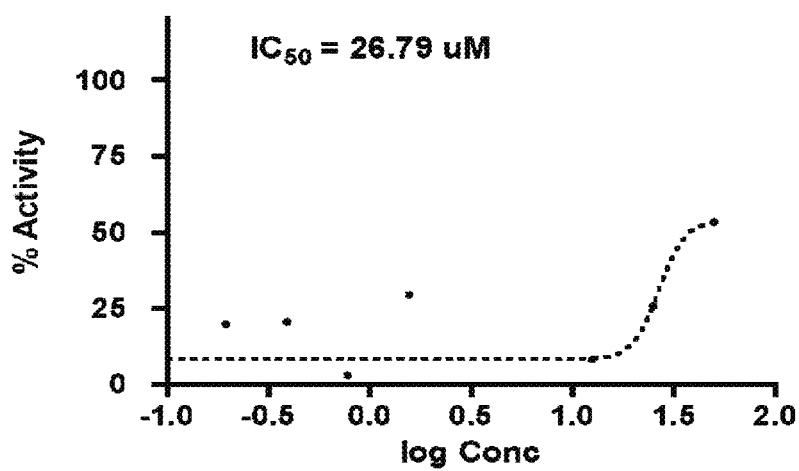

In accordance with standard practice, the peptoid oligomers are compared to a known antimalarial agent, namely chloroquine, so as to assess the ability of these compounds to inhibit the growth of *P. falciparum*. The IC$_{50}$ values for C(3-15), which is also referred to herein as C124, and C(5-1) are 16.98 μM. and 26.79 μM, respectively (FIGS. 12A and B). These results demonstrate that C124 and C(5-1) possess significant activity with respect to inhibiting *P. falciparum* growth and therefore, show promise in applications wherein they are used as antimalarial therapeutics.

Example 3

Antimicrobial Activity.

Antimicrobial susceptibility assays were conducted in 96-well plates using the broth microdilution procedure outlined herein. Screening against *Staphylococcus aureus* LAC was performed in LB (Luria-Bertani) medium. Experiments were conducted in three independent replicates of three trials.

Time-to-Kill Assay.

The kinetics of antimicrobial activity were evaluated while incubating the bacteria with MIC levels of each peptoid. At specified time points, aliquots were removed and diluted in LB media in 10-fold increments. A 20 µL sample of each diluted aliquot was plated on LB agar plates and incubated overnight at 37° C. Bacterial colonies were manually counted and the colony forming units per mL (CFU/mL) were determined. Results are the averages of three trials.

Scanning Electron Microscopy.

Samples for imaging were prepared and analyzed as described herein. Briefly, treated cells were collected by centrifugation at 21,000 G and washed with phosphate buffer (0.1 M. $Na_2HPO_4$, pH 7.4). The samples were resuspended in phosphate buffer and dried at room temperature on a 1 $cm^2$ membrane filter (Millipore, 0.45 µm). The samples were fixed with glutaraldehyde (2% w/v in sterile $H_2O$; Alfa Aesar) for 1 h at room temperature, washed with phosphate buffer, and then fixed with $OsO_4$ (0.5% w/v in sterile $H_2O$; Electron Microscopy Sciences) at 4° C. overnight. The samples were washed with phosphate buffer, and then treated twice with ethanol (30% aq.) for 10 min, with uranyl acetate (3% w/v in 30% ethanol; Electron Microscopy Sciences) for 2 h, with ethanol (50% aq.) for 10 min, and then with ethanol (70% aq.) overnight at 4° C. The samples were removed and dried at room temperature, then attached to an aluminum pin stub with a carbon conductive adhesive (PELCO), sputter-coated with a 5 nm layer of gold (Electron Microscopy Sciences coater EMS1505ES), and imaged with a Zeiss Merlin FESEM under SE2 detection at 2.0-4.0 kV.

Osmoprotection Assay.

The protocol for the antimicrobial susceptibility assay was used for the osmoprotection studies as well (Institute CaLS. 2006. Methods for Dilution Antimicrobial Susceptibility Tests for Bacteria That Grow Aerobically-Seventh Edition; Approved Standard CLSI document M07-A7. CLSI, Wayne, USA). The sole difference was that prior to overnight incubation at 37° C. and 200 rpm, 50 µL of 46.5 mM aqueous osmoprotectant was added to specified wells bringing the final osmoprotectant concentration to 15 mM. Each well contained a final volume of 155 µL. The osmoprotectants utilized were PEG 400, PEG 1000, PEG 3350, PEG 6000, and PEG 8000. Poly(ethylene glycol) polymers were purchased from Sigma-Aldrich with corresponding molecular weight ranges of 380-420, 950-1050, 3000-3700, 5000-7000, and 7000-9000. Each osmoprotection assay also included antimicrobial control wells with no additive.

Antimicrobial Activity.

Four representative cyclic peptoids, C(1-3), C(1-4), C(1-11), and C(1-14), were synthesized in order to probe the mechanism of action. The compounds studied varied by the incorporation of different hydrophobic side chains while the cationic side chain, ethylamine, was consistently utilized for all oligomers. Peptoid hydrophobicity was varied to investigate how different degrees of amphiphilicity affect mechanistic details. The minimum inhibitory concentration (MIC) of each compound against methicillin-resistant *Staphylococcus aureus* (MRSA) was determined by microdilution assays. Retention times used to indicate hydrophobicity arise from RP-HPLC running 5-95% ACN/$H_2O$ with 0.1% TFA in 10 min on a C18 column. Optical density was determined at 600 nm. Each compound exhibited low µg/ml MIC values with the exception of C(1-14), which had a MIC of 128.0 µg/mL, representing a structure with moderate activity. The antimicrobial activity of each peptoid was also investigated under conditions of increased initial bacterial density. The lethal concentration of each compound was determined at a cell density 20 times greater than the cell density utilized for MIC determination. Despite this large increase in the amount of bacteria treated, each compound retained potency, even at low concentrations. Peptoids C(1-3) and C(1-4) both showed a two-fold increase in MIC from 8.0 µg/mL to 16.0 µg/mL and 4.0 µg/mL to 8.0 µg/mL, respectively, the MIC of C(1-11) increased from 3.0 µg/mL to 4.0 µg/mL, and the MIC of C(1-14) remained at 128.0 µg/mL.

The bactericidal activity was examined by determining the antimicrobial kinetics. Kinetics of peptoid killing against MRSA was performed as follows: cells were treated with 3.0 µg/mL of C(1-11), 4.0 µg/mL of C(1-4), 8.0 µg/mL of C(1-3), or 128.0 µg/mL of C(1-14). Each cyclic peptoid demonstrated rapid bacterial cell killing, greatly reducing the number of colony forming units over a period of 120 min when treated at the MIC. Peptoid C(1-11) exhibited the fastest killing kinetics by achieving 90% cell death within 10 min and 99% cell death within 60 min. Compounds C(1-3), C(1-4), and C(1-14), in addition to possessing MIC values greater than C(1-11), had slower killing kinetics, the slowest of which, C(1-3) and C(1-14), both induced 90% cell death in 120 min.

Scanning Electron Microscopy.

Scanning electron microscopy (SEM) was utilized in order to visualize the damaging effects that antimicrobial cyclic peptoids have on the cell membrane of MRSA. Here, MRSA was treated with peptoids C(1-3) and C(1-4) at a concentration of 0.5×MIC for 24 h before preparation for evaluation by SEM. This sub-MIC was chosen so as to prevent complete cell death after 24 h treatment and allow growth to a cell density large enough to prepare samples. Untreated MRSA cells appeared spherical with smooth outer surfaces after 24 h growth. These cells were abundant throughout the sample and were arranged in clusters, as is typical for *S. aureus*. MRSA treated with either peptoid differed greatly from control cells. Peptoid-treated cells no longer possessed smooth outer surfaces, but rather were rough and exhibited a cracked surface morphology. Additionally, many treated cells were observed with large depressions in the surface. These features are likely to indicate the presence of transmembrane pores (Huang M. L., et. al. European Journal of Organic Chemistry 2013, 3560-3566). The formation of pores was extensive among the treated cells, even at a sub-MIC level of antimicrobial agent. The approximate pore sizes were measured from the SEM images, with most pores exceeding 200 nm in diameter after 24 h peptoid treatment.

Osmoprotection.

It has been proposed that antimicrobial oligomers act by creating pores in bacterial cell membranes. Thus, cell lysis is thought to result from osmotic shock due to the leakage of intracellular contents and the large influx of water into damaged cells. To probe this possible mechanism for cyclic peptoids, osmoprotectants were added to suspensions of MRSA prior to treatment with the antimicrobial agents. The presence of osmoprotectants among antimicrobial-treated bacteria can reveal the occurrence of pore formation.

Smaller osmoprotectants are capable of passing through pores, providing no protection from a loss in osmotic balance. However, if osmoprotectants are large enough, they are able to prevent the influx of water that causes cells to burst, thus protecting against the harmful effects of pore-forming antimicrobials. Manifestation of osmoprotection is observed as a decrease in antimicrobial activity due to the increased persistence of viable cells. Polyethylene glycol (PEG) polymers with hydrodynamic radii ranging from 1.36 nm (PEG 400) to 6.40 nm (PEG 8000) were utilized in order to determine the osmoprotectant size needed for protection to occur (Scherrer R., et. al. Journal of Bacteriology 1971, 107, 718-735). The ability of PEG polymers to protect from bacterial lysis due to a loss of osmotic balance was tested by treating MRSA with cyclic peptoids [C(1-3) and C(1-4)] at varying concentrations in the presence of 15 mM osmoprotectant solutions and determining the change in MIC after overnight incubation.

For osmoprotection to occur, the size and concentration of the osmoprotectant are both critical parameters. Generally, the osmoprotectant concentration should be near isotonic with respect to intracellular solute concentration, which for erythrocytes is approximately 30 mM (Lobo A. L. et al. In Virginia L. Clark PMB (ed.), Methods in Enzymology (Academic Press), 1994, vol. 235, 667-678). The present inventors observed that 30 mM PEG solutions exhibited excessive viscosity that hindered bacterial growth. Thus, the inventors used 15 mM osmoprotectant solutions in the assays. Similar observations of viscosity have been reported previously for osmoprotection of bacterial cells, and 15 mM osmoprotectant solutions proved to be effective (Sato H. et. al., Biochemistry 2006, 45, 9997-10007). Since the extent of protection is dependent upon both the diameter and concentration of the osmoprotectant, the concentration was kept constant while varying the diameter. This allowed observation of size dependence for protection, enabling estimation of the size of the pores formed.

Osmoprotection was absent in suspensions incubated with compounds C(1-3) and C(1-4) in the presence of 15 mM PEG 400 or PEG 1000, which have hydrodynamic diameters of 1.36 nm and 2.0 nm, respectively. In contrast, addition of PEG 3350 (3.8 nm) to MRSA suspensions resulted in protection against both compounds. This protection was observed as increases in MIC, 8.0 μg/mL to 12.0 μg/mL for C(1-3) and 4.0 μg/mL to 8.0 μg/mL for C(1-4), indicating diminished antimicrobial activity. For peptoid C(1-3), antimicrobial activity continued to decrease in the presence of larger osmoprotectants with only 40% activity in 15 mM PEG 8000 compared to no osmoprotectant. The activity of peptoid C(1-4) did not continue to decrease as for C(1-3), but rather remained at 50% activity in the presence of PEG 3350, 6000, and 8000. The efficiency of osmoprotection from the antimicrobial peptoids strongly supports a bacteriocidal mechanism involving transmembrane pore formation.

As described above, cyclic peptoids are capable of exhibiting high potency against MRSA. It was also demonstrated using SEM that cyclic peptoids disrupt the cell membrane of MRSA, suggesting the importance of peptoid-membrane interactions. The mechanism of action of cyclic peptoids was further investigated here using four compounds, C(1-3), C(1-4), C(1-11), and C(1-14), and results indicate that the bacterial cell membrane is a primary target of antimicrobial cyclic peptoids, which act as pore-formers Thus far, antimicrobial cyclic peptoids have proven to be potent, selective, and rapid antimicrobials that act primarily at the bacterial membrane of MRSA. These features indicate the ability of cyclic peptoids of the present invention to become effective therapeutics against bacterial pathogens that present difficulties for conventional antibiotics.

From the foregoing description, various modifications and changes in the compositions and methods described will occur to skilled artisans. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A peptoid oligomer according to formula VIIa, VIIb, VIIc, VIIIa, VIIIb or VIIIc:

VIIa

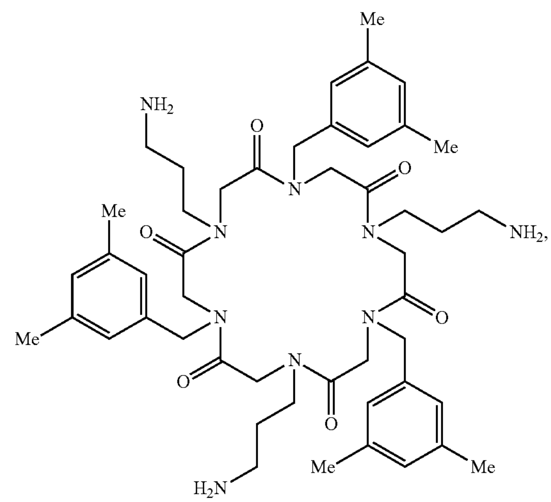

VIIb

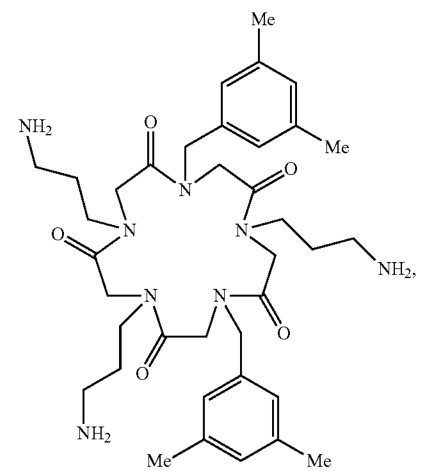

VIIc
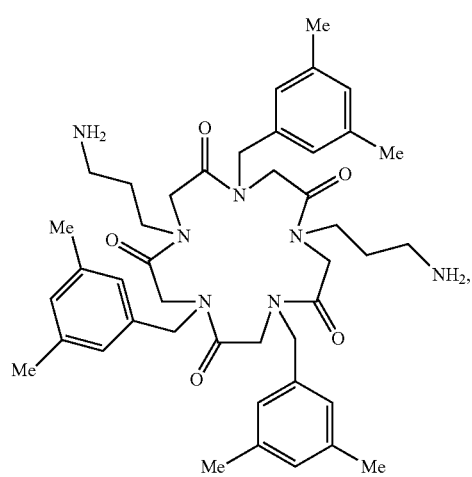
VIIIa
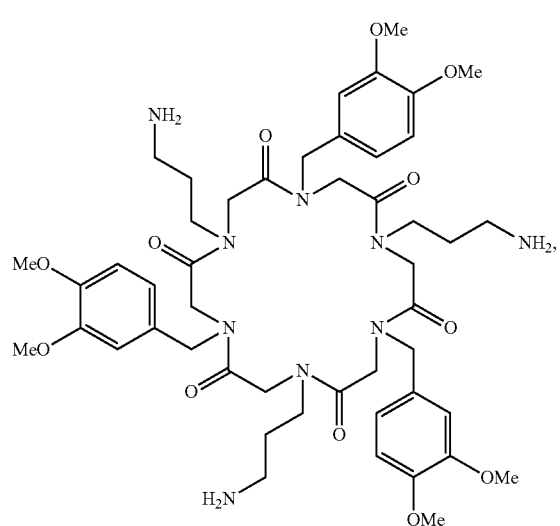
VIIIb
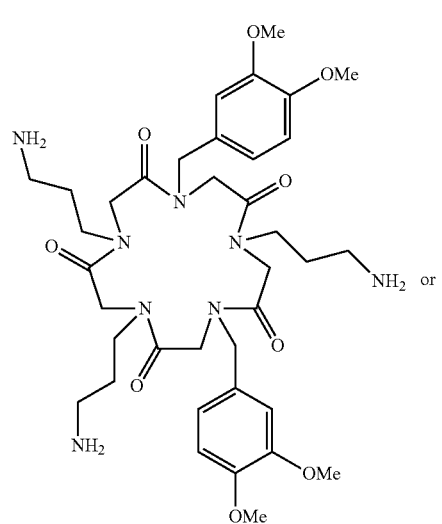
VIIIc
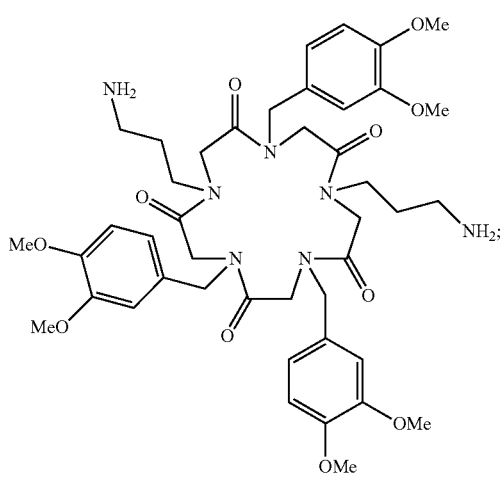
or a peptoid oligomer according to formula VIIa, VIIb, VIIc, VIIIa, VIIIb or VIIIc, and wherein the —NH$_2$ of each —CH$_2$—CH$_2$—CH$_2$—NH$_2$ is replaced with —NMe$_2$, —NHMe, or —NEt$_2$;
or a pharmaceutically acceptable salt, or solvate thereof or a stereoisomer, isotopic variant or tautomer thereof.
2. A peptoid oligomer C103, C105, C106, C121, C122, C123, C124, or C125:
C103
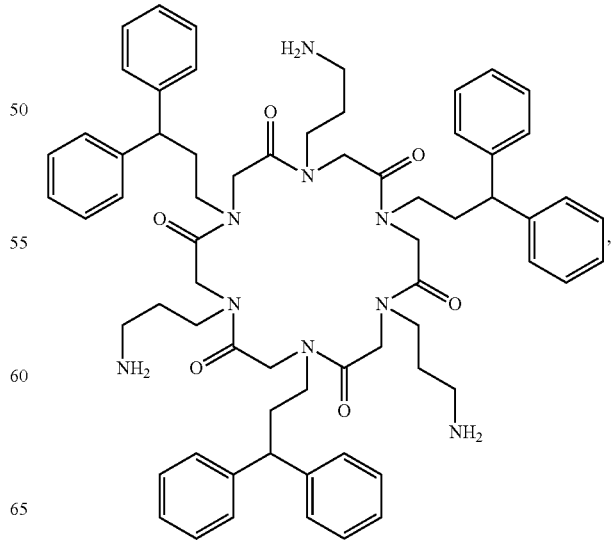

C105
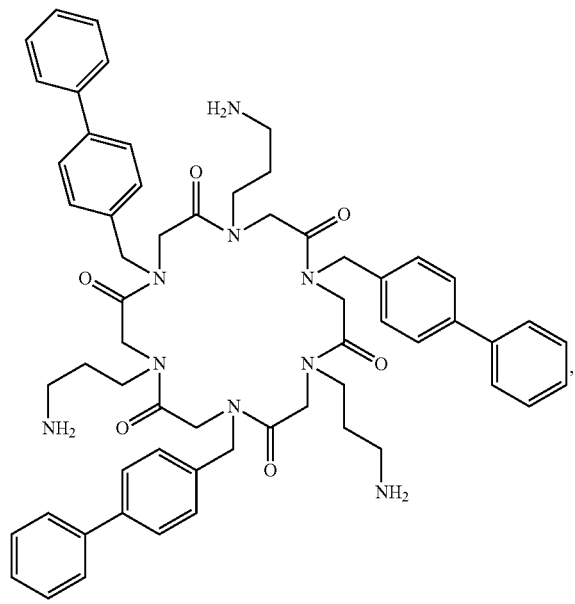
C106
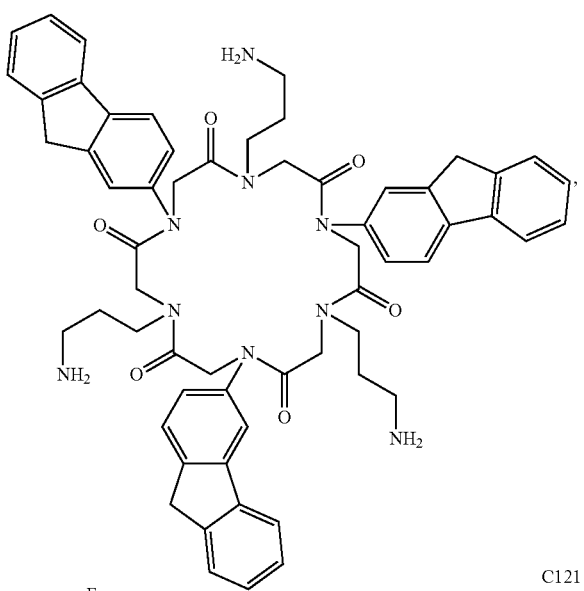
C121
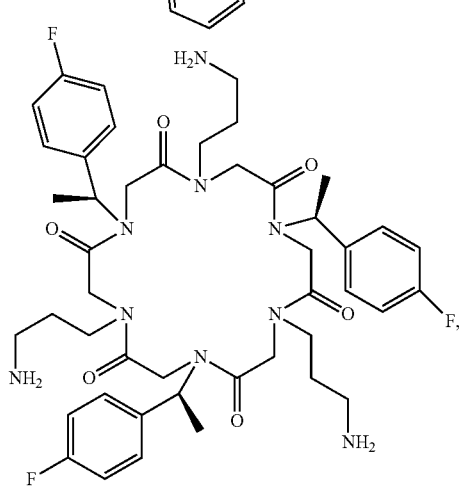
C122
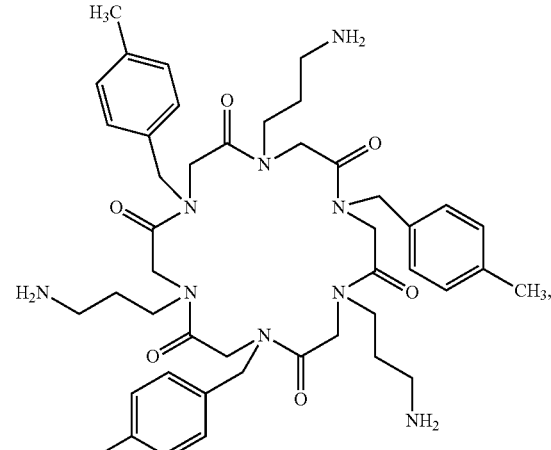
C123
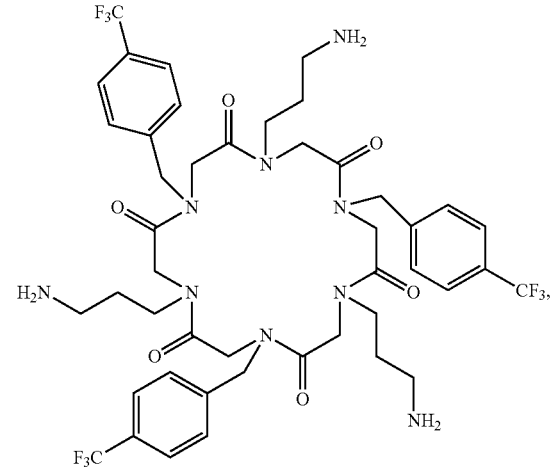
C124
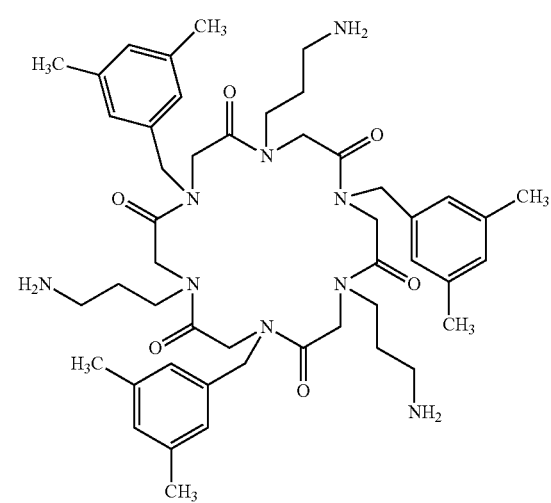
or -continued

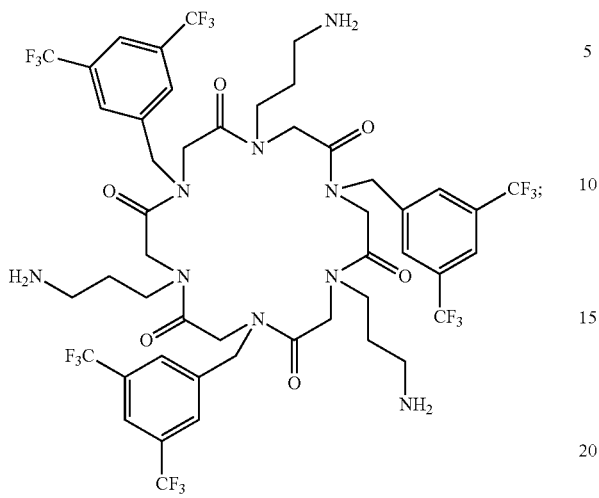

C125 or a peptoid oligomer according to C103, C105, C106, C121, C122, C123, C124, or C125, and wherein the —NH$_2$ of each —CH$_2$—CH$_2$—CH$_2$—NH$_2$ is replaced with —NMe$_2$, —NHMe, or —NEt$_2$;

or a pharmaceutically acceptable salt, or solvate thereof or a stereoisomer, isotopic variant or tautomer thereof.

3. A peptoid oligomer according to formula IIIa:

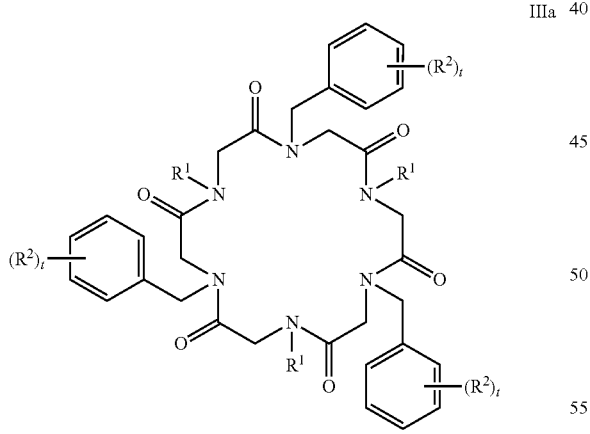

IIIa wherein t is 2; one R$^2$ is 3-Me and the other R$^2$ is 5-Me; and R$^1$ is 2-aminoethyl, 3-aminopropyl, 2-(dimethylamino)ethyl, 2-(diethylamino)ethyl, 2-(methylamino)ethyl, 3-(dimethylamino)propyl, 3-(diethylamino)propyl, or 3-(methylamino)propyl;

or a pharmaceutically acceptable salt, or solvate thereof; or a stereoisomer, isotopic variant or tautomer thereof.

4. A peptoid oligomer according to formula IIIb, or IIIc:

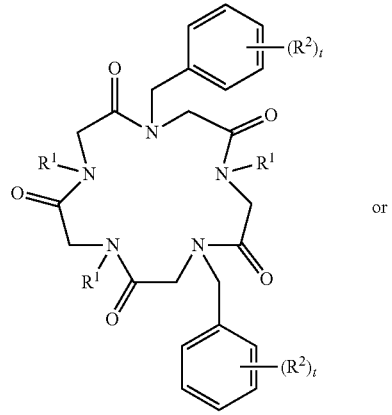

IIIb or

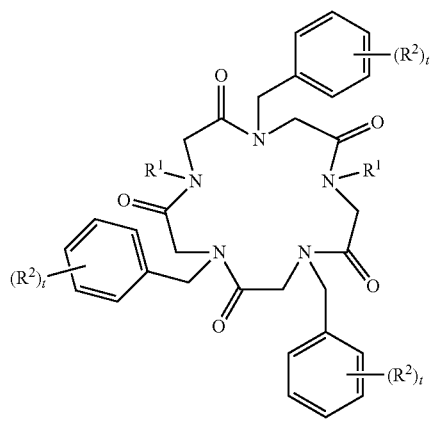

IIIc wherein R$^1$ is 2-aminoethyl, 3-aminopropyl, 2-(dimethylamino)ethyl, 2-(diethylamino)ethyl, 2-(methylamino)ethyl, 3-(dimethylamino)propyl, 3-(diethylamino)propyl, or 3-(methylamino)propyl; t is 2; and one R$^2$ is 3-Me and the other R$^2$ is 5-Me;

or a pharmaceutically acceptable salt, or solvate thereof; or a stereoisomer, isotopic variant or tautomer thereof.

5. A peptoid oligomer:

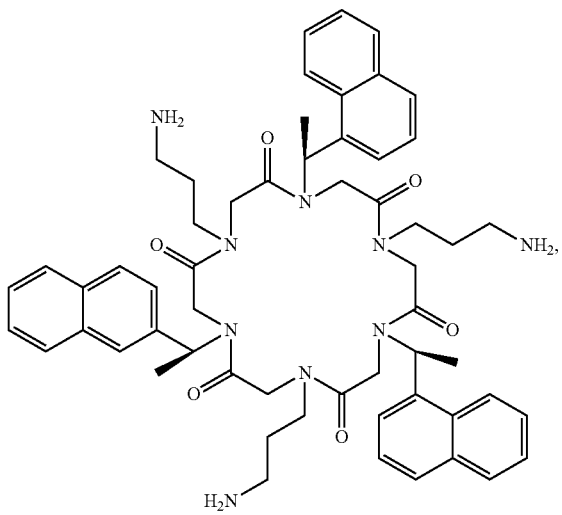

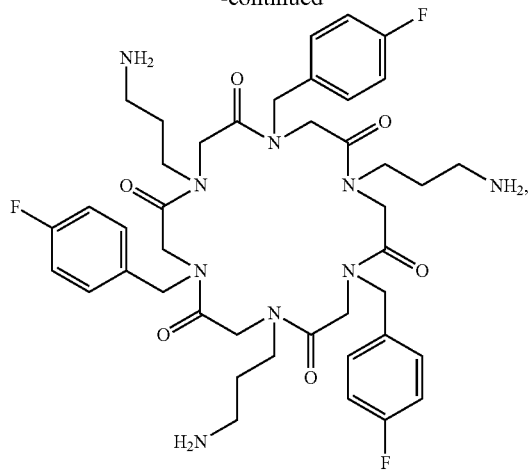

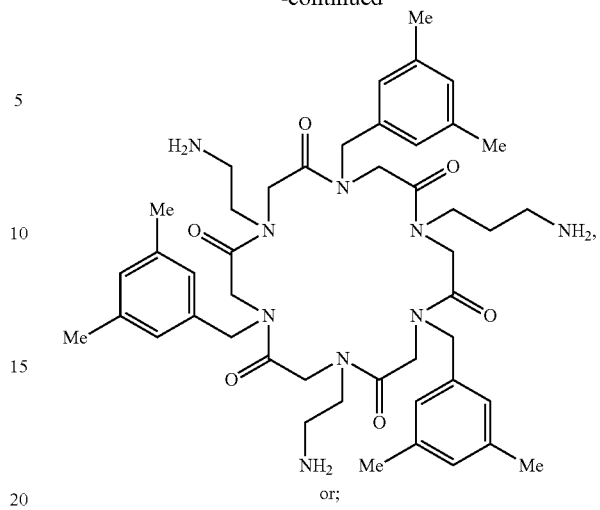

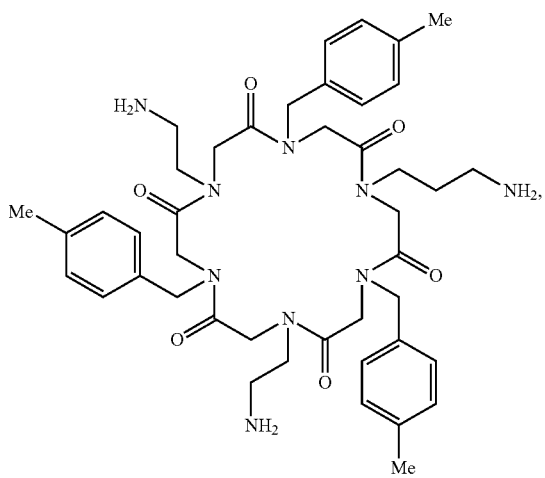

or the peptoid oligomer wherein the —NH₂ of each —CH₂—CH₂—CH₂—NH₂ or the —NH₂ of each —CH₂—CH₂—NH₂ is replaced with —NMe₂, —NHMe, or —NEt₂;

or a pharmaceutically acceptable salt, or solvate thereof; or a stereoisomer, isotopic variant or tautomer thereof.

6. The peptoid oligomer according to
i) any one of claim 3 or 4, wherein R¹ is
2-(dimethylamino)ethyl, 2-(diethylamino)ethyl, 2-(methylamino)ethyl, 3-(dimethylamino)propyl, 3-(diethylamino)propyl, or 3-(methylamino)propyl.

7. A pharmaceutical composition comprising a pharmaceutically acceptable carrier and a pharmaceutically effective amount of the peptoid oligomer of any one of claim 1, 2, or 3.

8. A pharmaceutical composition comprising a pharmaceutically acceptable carrier and a pharmaceutically effective amount of the peptoid oligomer of any one of claim 4 or 5.

9. A method for treating, ameliorating or managing a disease or condition that is or results from a bacterial infection, wherein the method comprises administering to a patient in need of such treatment, amelioration or management, a therapeutically effective amount of a peptoid oligomer of any one of claim 1, 2, 3, 4, or 5, or a pharmaceutical composition thereof.

10. The method of claim 9, wherein the disease or condition is or results from infection with gram positive or gram negative bacterial strains.

11. The method of claim 10, wherein the disease or condition is or results from infection with *Staphylococcus aureus*.

12. The method of claim 10, wherein the disease or condition is or results from infection with Methicillin-resistant *Staphylococcus aureus* (MRSA).

* * * * *